US012612444B2

(12) United States Patent
Kammula et al.

(10) Patent No.: US 12,612,444 B2
(45) Date of Patent: Apr. 28, 2026

(54) T CELL RECEPTORS TARGETING MUTATIONS IN RNA SPLICING FACTORS

(71) Applicant: University of Pittsburgh—Of the Commonwealth System of Higher Education, Pittsburgh, PA (US)

(72) Inventors: Udai Shankar Kammula, Pittsburgh, PA (US); Ghanshyam Singh Yadav, Pittsburgh, PA (US); Chetana Bhaskarla, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1008 days.

(21) Appl. No.: 17/779,711

(22) PCT Filed: Nov. 25, 2020

(86) PCT No.: PCT/US2020/062164
§ 371 (c)(1),
(2) Date: May 25, 2022

(87) PCT Pub. No.: WO2021/108500
PCT Pub. Date: Jun. 3, 2021

(65) Prior Publication Data
US 2023/0031784 A1 Feb. 2, 2023

Related U.S. Application Data

(60) Provisional application No. 62/940,725, filed on Nov. 26, 2019.

(51) Int. Cl.
| | |
|---|---|
| *A61P 35/00* | (2006.01) |
| *A61K 40/11* | (2025.01) |
| *A61K 40/32* | (2025.01) |
| *A61K 40/42* | (2025.01) |
| *C07K 14/725* | (2006.01) |
| *C12N 15/86* | (2006.01) |

(52) U.S. Cl.
CPC .......... *C07K 14/7051* (2013.01); *A61K 40/11* (2025.01); *A61K 40/32* (2025.01); *A61K 40/42* (2025.01); *A61P 35/00* (2018.01); *C12N 15/86* (2013.01); *C07K 2319/50* (2013.01); *C12N 2740/15043* (2013.01)

(58) Field of Classification Search
None
See application file for complete search history.

(56) References Cited

U.S. PATENT DOCUMENTS

| | | | | | |
|---|---|---|---|---|---|
| 2008/0219956 A1* | 9/2008 | Russell | ................ | C12N 15/907 | 435/320.1 |
| 2013/0164746 A1* | 6/2013 | Rossi | ................... | C12Q 1/6886 | 435/6.11 |

| | | | |
|---|---|---|---|
| 2015/0307585 A1 | 10/2015 | Blankenstein et al. | |
| 2019/0233498 A1 | 8/2019 | Loomis et al. | |
| 2019/0233522 A1 | 8/2019 | Forssmann et al. | |
| 2019/0241667 A1 | 8/2019 | Papadopoulos et al. | |
| 2023/0348557 A1 | 11/2023 | Kammula et al. | |

FOREIGN PATENT DOCUMENTS

| | | |
|---|---|---|
| WO | WO 1998/022143 | 5/1998 |
| WO | WO 1998/046778 | 10/1998 |
| WO | WO 2000/017376 | 3/2000 |
| WO | WO 2016/156478 | 10/2016 |
| WO | WO 2017/193104 | 11/2017 |
| WO | WO 2019/099689 | 5/2019 |
| WO | WO 2019/195576 | 10/2019 |
| WO | WO 2019/196088 | 10/2019 |
| WO | WO 2019/199945 | 10/2019 |

OTHER PUBLICATIONS

Popovic et al. (Blood. 2011; 118(4):946-954). (Year: 2011).*
Bossi et al. (OncoImmunology, 2013, 2:11, e26840). (Year: 2013).*
Nakatsugawa et al., International Journal of Oncology 39: 1041-1049, 2011. (Year: 2011).*
Janeway et al., Immunobiology, 5th Ed., Garland Science, pp. 106-108, 117-118 and 260-263, (2001). (Year: 2001).*
Goyarts et al., Mol Immunol. Jul. 1998;35(10):593-607. (Year: 1998).*
Garcia et al., Cell, vol. 122, 333-336, Aug. 12, 2005. (Year: 2005).*
Maguire et al. (J Pathol 2015; 235: 571-580). (Year: 2015).*
Pereira et al. (Nat Commun. May 10, 2016;7:11479). (Year: 2016).*
Rose et al., BMC Cancer (2018) 18:1262. (Year: 2018).*
Hintzsche et al., Melanoma Research 2017, 27:189-199. (Year: 2017).*
Fisher et al., "A novel adenovirus-adeno-associated virus hybrid vector that displays efficient rescue and delivery of the AAV genome," Hum. Gene Therapy, Nov. 10, 1996, 7(17):2079-2087.
Gervasi et al., "Parenteral protein formulations: An overview of approved products within the European Union," Eur. J Pharm. Biopharmaceutics, Oct. 2018, 131:8-24.
International Preliminary Report on Patentability in International Appln. No. PCT/US2020/062164, mailed on Jun. 9, 2022, 9 pages.
International Search Report and Written Opinion in International Appln. No. PCT/US2020/062164, mailed on Apr. 30, 2021, 12 pages.

(Continued)

*Primary Examiner* — Zachary S Skelding
(74) *Attorney, Agent, or Firm* — Fish & Richardson P.C.

(57) ABSTRACT

This document provides isolated immune cells that include an exogenous T cell receptor (TCR) having affinity for a splicing factor 3B subunit 1A (SF3B1) peptide as well as methods and materials for making such immune cells. For example, isolated immune cells that included an exogenous TCR having affinity for a mutant SF3B1 peptide, methods and materials for making such immune cells, and methods and materials for using such immune cells to treat mammals (e.g., a human having cancer) are provided.

22 Claims, 37 Drawing Sheets

Specification includes a Sequence Listing.

(56) References Cited

OTHER PUBLICATIONS

Kammula, "TIL Therapy for Cholangiocarcinoma and Pancreatic Carcinoma", Presented at Proceedings of the Pancreatic Cancer Minisymposium, Hillman Cancer Center, UPMC, Pittsburgh, PA, May 7, 2019, 1 page (Minisymposium Schedule).

Kuball et al., "Facilitating matched pairing and expression of TCR chains introduced into human T cells," Blood, Mar. 15, 2007, 109(6):2331-2338.

Liberante et al., "Altered splicing and cytoplasmic levels of tRNA synthetases in SF3B1-mutant myelodysplastic syndromes as a therapeutic vulnerability," Sci. Reports, Feb. 25, 2019, 9(1):2678, 13 pages.

Neumann et al., "Gene transfer into mouse lyoma cells by electroporation in high electric fields," EMBO Journal, 1982, 1(7):841-845.

UniProt Accession No. O75533, "Splicing factor 3B subunit 1," Nov. 7, 2018, 15 pages.

Wang et al., "Clinical manufacturing of CAR T cells: foundation of a promising therapy," Mol. Ther. Oncolytics, Jun. 15, 2016, 3:16015, 7 pages.

Zhang et al., "Cancer-Linked SF3B1 Mutations Cause Faulty Splicing and SUGP1 Binding," Cancer Discovery, Oct. 1, 2019, 9(10):1336.

Zheng et al., "Genomic integration and gene expression by a modified adenoviral vector," Nat. Biotechnology, Feb. 2000, 18(2):176-180.

Zoller, "New recombinant DNA methodology for protein engineering," Curr. Opin. Biotechnology, Aug. 1992, 3(4):348-354.

Bitler et al., "ARIDIA-mutated ovarian cancers depend on HDAC6 activity," Nat. Cell Biol., Aug. 2019, 19(8):962-973, 30 pages.

Choi et al., "ATM Mutations in Cancer: Therapeutic Implications," Mol. Cancer Ther., Aug. 2016, 15(8):1781-1791.

Extended European Search Report in European Appln. No. 20894301.9, dated Nov. 30, 2023, 7 pages.

Extended European Search Report in European Appln. No. 21751111.2, dated Nov. 8, 2023, 11 pages.

International Preliminary Report on Patentability in International Appln. No. PCT/US2021/016883, mailed on Aug. 18, 2022, 5 pages.

International Search Report and Written Opinion in International Appln. No. PCT/US2021/016883, mailed on Jun. 24, 2021, 5 pages.

Partial Supplementary European Search Report in European Appln No. 21751111.2, dated Aug. 7, 2023, 15 pages.

Takahashi et al., "Adult classical glioblastoma with a BRAF V600E mutation," World J. Surg. Oncol., Mar. 2015, 13:100, 5 pages.

Yadav et al., Abstract #: P228: "Tumor infiltrating lymphocyte recognition of shared neoantigens from mutated DNA repair/remodeling proteins in a patient with metastatic pancreatic adenocarcinoma," Presented at the Proceedings of the 34th Annual Meeting & Pre-Conference Programs of the Society for Immunotherapy of Cancer (SITC 2019): part 1; National Harbor, MD, USA. Nov. 6-10, 2019, J. Immunother. Cancer, Nov. 2019, 7(Suppl 1):282, p. 122.

U.S. Appl. No. 17/795,573, filed Jul. 27, 2022, Udai Shankar Kammula, Published as U.S. Patent Application No. 2023/0348557.

* cited by examiner

Figure 1A

Wild type:   MRPDIDNMDEYVRNTTARAFAVVAS

Mutant:     MRPDIDNMDEYVHNTTARAFAVVAS

Figure 1B

TRBV2-01+TRAV12-02 Chimeric TCR

Variable: Native Human
Constant: Mouse (Codon Optimized)

Order of sequence
Human Beta Variable (with CDR1b, CDR2b, CDR3b underlined)-Mouse Beta Constant (italics)- P2A Cleavage site (in bold)-Human Alpha Variable (CDR1a, CDR2a, CDR3a underlined)- Mouse Alpha Constant (italics).

Nucleotide sequence
ATGGATACCTGGCTCGTATGCTGGGCAATTTTTAGTCTCTTGAAAGC
AGGACTCACAGAACCTGAAGTCACCCAGACTCCCAGCCATCAGGTCA
CACAGATGGGACAGGAAGTGATCTTGCGCTGTGTCCCCATC<u>TCTAAT
CACTTATACTTCTATTGG</u>TACAGACAAATCTTGGGGCAGAAAGTCGA
GTTTCTGGTTTCC<u>TTTTATAATAATGAAATCTCAGAGAAGTCTGAAA</u>
TATTCGATGATCAATTCTCAGTTGAAAGGCCTGATGGATCAAATTTC
ACTCTGAAGATCCGGTCCACAAAGCTGGAGGACTCAGCCATGTACTT
CTGTGCCAGCAG<u>TAAAGACTACCGGGGAGGTGAAAAACTGTTTTTG</u>
GCAGTGGAACCCAGCTCTCTGTCTT*GGAGGACCTGAGAACGTGACACCC
CCTAAGGTGAGCCTGTTCGAGCCCTCCAAGGCCGAGATCGCCAATAAGCAGAAG
GCCACCCTGGTGTGCCTGGCAAGGGGCTTCTTTCCTGATCACGTGGAGCTGTCT
TGGTGGGTGAACGGCAAGGAGGTGCACAGCGGCGTGTGCACCGACCCACAGGCC
TATAAGGAGAGCAATTATTCCTACTGTCTGTCTAGCCGGCTGAGAGTGAGCGCC
ACATTTTGGCACAACCCTCGGAATCACTTCAGATGCCAGGTGCAGTTTCACGGC
CTGTCTGAGGAGGATAAGTGGCCAGAGGGCAGCCCAAAGCCAGTGACCCAGAAC
ATCTCCGCCGAGGCATGGGAAGAGCAGACTGTGGCATCACCAGCGCCTCCTAC
CAGCAGGGCGTGCTGTCCGCCACAATCCTGTATGAGATCCTGCTGGGCAAGGCC
ACCCTGTACGCCGTGCTGGTGAGCACACTGGTGGTCATGGCTATGGTGAAGAGG*
AAGAACTCC**AGGGCAAAGCGGAGCGGAAGCGGAGCCACAAATTTCTCTCTGCTG
AAGCAGGCAGGCGATGTGGAGGAGAACCCTGGACCA**ATGATGAAATCCTTGA

Figure 1B (Cont.)

GAGTTTTACTAGTGATCCTGTGGCTTCAGTTGAGCTGGGTTTGGAGC
CAACAGAAGGAGGTGGAGCAGAATTCTGGACCCCTCAGTGTTCCAGA
GGGAGCCATTGCCTCTCTCAACTGCACTTACAGTGACCGAGGTTCCC
AGTCCTTCTTCTGGTACAGACAATATTCTGGGAAAAGCCCTGAGTTG
ATAATGTCCATATACTCCAATGGTGACAAAGAAGATGGAAGGTTTAC
AGCACAGCTCAATAAAGCCAGCCAGTATGTTTCTCTGCTCATCAGAG
ACTCCCAGCCCAGTGATTCAGCCACCTACCTCTGTGCCGCCCTGAGG
CCTGGTGGCTACAATAAGCTGATTTTTGGAGCAGGGACCAGGCTGGC
*TGTACACCCAAACATCCAGAATCCAGAGCCCGCCGTGTATCAGCTGAAGGACC*
*CAAGATCCCAGGATTCTACCCTGTGCCTGTTCACAGACTTTGATTCTCAGATCA*
*ATGTGCCCAAGACAATGGAGAGCGGCACCTTCATCACAGACAAGTGCGTGCTGG*
*ATATGAAGGCTATGGACTCCAAGTCTAACGGCGCCATCGCCTGGAGCAATCAGA*
*CCTCCTTCACATGCCAGGATATCTTTAAGGAGACAAACGCCACATACCCTTCTA*
*GCGACGTGCCATGTGATGCCACCCTGACAGAGAAGAGCTTCGAGACAGACATGA*
*ACCTGAATTTTCAGAATCTGCTGGTCATCGTGCTGCGGATCCTGCTGCTGAAGG*
*TGGCTGGGTTTAATCTGCTGATGACACTGCGACTGTGGAGTAGCTGATGA*

Amino Acid sequence
MDTWLVCWAIFSLLKAGLTEPEVTQTPSHQVTQMGQEVILRCVPISN
HLYFYWYRQILGQKVEFLVSFYNNEISEKSEIFDDQFSVERPDGSNF
TLKIRSTKLEDSAMYFCASSKDYRGGEKLFFGSGTQLSVL*EDLRNVTP*
*PKVSLFEPSKAEIANKQKATLVCLARGFFPDHVELSWWVNGKEVHSGVCTDPQA*
*YKESNYSYCLSSRLRVSATFWHNPRNHFRCQVQFHGLSEEDKWPEGSPKPVTQN*
*ISAEAWGRADCGITSASYQQGVLSATILYEILLGKATLYAVLVSTLVVMAMVKR*
*KNS*RAKRSGSGATNFSLLKQAGDVEENPGPMMKSLRVLLVILWLQLSWVWS
QQKEVEQNSGPLSVPEGAIASLNCTYSDRGSQSFFWYRQYSGKSPEL
IMSIYSNGDKEDGRFTAQLNKASQYVSLLIRDSQPSDSATYLCAALR
PGGYNKLIFGAGTRLAVHP*NIQNPEPAVYQLKDPRSQDSTLCLFTDFDSQI*
*NVPKTMESGTFITDKCVLDMKAMDSKSNGAIAWSNQTSFTCQDTFKETNATYPS*
*SDVPCDATLTEKSFETDMNLNFQNLLVTVLRILLLKVAGFNLLMTLRLWSS*

Figure 2

TRBV2-01+TRAV12-02 Chimeric TCR (Codon Optimized)

Variable: Native Human (Codon Optimized)
Constant: Mouse (Codon Optimized)
Order of sequence
Human Beta Variable (CDR1b, CDR2b, CDR3b
underlined)-Mouse Beta Constant (italics)- **P2A cleavage
site (in bold)**- Human Alpha Variable (including
CDR1a, CDR2a, CDR3a underlined)- Mouse Alpha Constant
(italics).

Nucleotide sequence
ATGGACACCTGGCTGGTGTGCTGGGCCATCTTCTCTCTGCTGAAGGC
AGGACTGACCGAGCCAGAGGTGACCCAGACACCTTCCCACCAGGTGA
CACAGATGGGCCAGGAAGTGATCCTGAGATGCGTGCCAATCAGCAAC
CACCTGTACTTTTATTGGTACCGCCAGATCCTGGGCCAGAAGGTGGA
GTTCCTGGTGTCCTTTTATAACAATGAGATCAGCGAGAAGTCCGAGA
TCTTCGACGATCAGTTTTCTGTGGAGCGGCCCGATGGCAGCAATTTC
ACCCTGAAGATCAGATCCACAAAGCTGGAGGATTCTGCCATGTATTT
TTGCGCAAGCTCCAAGGACTACAGGGGAGGAGAGAAGCTGTTCTTTG
GAAGCGGAACCCAGCTGTCCGTGCTG*GAGGACCTGCGCAACGTGACACCC*
*CCTAAGGTGTCTCTGTTCGAGCCAAGCAAGGCCGAGATCGCCAATAAGCAGAAG*
*GCCACCCTGGTGTGCCTGGCAAGGGGCTTCTTTCCGATCACGTGGAGCTGTCC*
*TGGTGGGTGAACGGCAAGGAGGTGCACTCTGGCGTGTGCACCGACCCTCAGGCC*
*TATAAGGAGTCTAATTATAGCTACTGTCTGTCTAGCCGGCTGAGAGTGAGCGCC*
*ACATTTTGGCACAACCCCCGGAATCACTTCAGATGCCAGGTGCAGTTTCACGGC*
*CTGTCCGAGGAGGATAAGTGGCCTGAGGGCTCTCCAAAGCCCGTGACCCAGAAC*
*ATCAGCGCCGAGGCATGGGGAAGGGCAGACTGTGGAATCACCTCTGCCAGCTAC*
*CAGCAGGGCGTGCTGTCCGCCACAATCCTGTATGAGATCCTGCTGGGCAAGGCC*
*ACCCTGTACGCCGTGCTGGTGTCTACACTGGTGGTCATGGCTATGGTGAAGCGG*
*AAGAACAGC*AGGGCAAAGCGGAGCGGATCTGGAGCCACAAATTTCTCCCTGCTG
AAGCAGGCCGGCGATGTGGAGGAGAATCCTGGCCCAATGATGAAGAGCCTGA
GAGTGCTGCTGGTCATCCTGTGGCTGCAGCTGTCCTGGGTGTGGTCT
CAGCAGAAGGAGGTGGAGCAGAACAGCGGACCACTGTCCGTGCCAGA
GGGAGCCATCGCCAGCCTGAATTGCACCTACTCC<u>GACAGGGGCAGCC</u>
<u>AGTCCTTCTTTTGGTATCGCCAGTACTCCGGCAAGTCTCCTGAGCTG</u>
ATCATGAGC<u>ATCTATTCCAACGGCGACAAG</u>GAGGATGGCCGGTTCAC
AGCCCAGCTGAATAAGGCCTCTCAGTACGTGAGCCTGCTGATCAGAG
ATTCCCAGCCATCTGATAGCGCCACCTACCTG<u>TGCGCCGCCCTGAGG</u>

Figure 2 (Cont.)

CCAGGAGGCTACAACAAGCTGATCTTTGGAGCAGGAACAAGACTGGC
AGTGCACCCTAACATCCAGAATCCCGAGCCTGCCGTGTATCAGCTGAAGGACC
CACGGTCTCAGGATAGCACCCTGTGCCTGTTCACAGACTTTGATAGCCAGATCA
ATGTGCCCAAGACAATGGAGTCCGGCACCTTCATCACAGACAAGTGCGTGCTGG
ATATGAAGGCTATGGACTCCAAGTCTAACGGCGCCATCGCCTGGTCCAATCAGA
CCTCTTTCACATGCCAGGATATCTTTAAGGAGACCAACGCCACATACCCTTCCT
CTGACGTGCCATGTGATGCCACCCTGACAGAGAAGAGCTTCGAGACCGACATGA
ACCTGAATTTTCAGAACCTGCTGGTCATCGTGCTGAGGATCCTGCTGCTGAAGG
TGGCCGGCTTTAATCTGCTGATGACACTGCGCCTGTGGAGCTCCTGATGA

Amino Acid sequence
MDTWLVCWAIFSLLKAGLTEPEVTQTPSHQVTQMGQEVILRCVPISN
HLYFYWYRQILGQKVEFLVSFYNNEISEKSEIFDDQFSVERPDGSNF
TLKIRSTKLEDSAMYFCASSKDYRGGEKLFFGSGTQLSVLEDLRNVTP
PKVSLFEPSKAEIANKQKATLVCLARGFFPDHVELSWWVNGKEVHSGVCTDPQA
YKESNYSYCLSSRLRVSATFWHNPRNHFRCQVQFHGLSEEDKWPEGSPKPVTQN
ISAEAWGRADCGITSASYQQGVLSATILYEILLGKATLYAVLVSTLVVMAMVKR
KNSRAKRSGSGATNFSLLKQAGDVEENPGPMMKSLRVLLVILWLQLSWVWS
QQKEVEQNSGPLSVPEGAIASLNCTYSDRGSQSFFWYRQYSGKSPEL
IMSIYSNGDKEDGRFTAQLNKASQYVSLLIRDSQPSDSATYLCAALR
PGGYNKLIFGAGTRLAVHPNIQNPEPAVYQLKDPRSQDSTLCLFTDFDSQI
NVPKTMESGTFITDKCVLDMKAMDSKSNGAIAWSNQTSFTCQDIFKETNATYPS
SDVPCDATLTEKSFETDMNLNFQNLLVIVLRILLLKVAGFNLLMTLRLWSS

Figure 3

TRBV2-01+TRAV12-02 Human TCR

Variable: Native Human
Constant: Native Human

Order of sequence

Human Beta Variable (including CDR1b, CDR2b, CDR3b
underlined)-Human Beta Constant (italics)- **P2A Cleavage
site (in bold)**-Human Alpha Variable (including CDR1a,
CDR2a, CDR3a underlined) — Human Alpha Constant
(italics.

Nucleotide sequence

ATGGATACCTGGCTCGTATGCTGGGCAATTTTTAGTCTCTTGAAAGC
AGGACTCACAGAACCTGAAGTCACCCAGACTCCCAGCCATCAGGTCA
CACAGATGGGACAGGAAGTGATCTTGCGCTGTGTCCCCATCTCTAAT
CACTTATACTTCTATTGGTACAGACAAATCTTGGGGCAGAAAGTCGA
GTTTCTGGTTTCCTTTTATAATAATGAAATCTCAGAGAAGTCTGAAA
TATTCGATGATCAATTCTCAGTTGAAAGGCCTGATGGATCAAATTTC
ACTCTGAAGATCCGGTCCACAAAGCTGGAGGACTCAGCCATGTACTT
CTGTGCCAGCAGTAAAGACTACCGGGGAGGTGAAAAACTGTTTTTTG
GCAGTGGAACCCAGCTCTCTGTCTTG*GAGGACCTGAACAAGGTGTTCCCA*
*CCCGAGGTCGCTGTGTTTGAGCCATCAGAAGCAGAGATCTCCCACACCCAAAAG*
*GCCACACTGGTGTGCCTGGCCACAGGCTTCTTCCCCGACCACGTGGAGCTGAGC*
*TGGTGGGTGAATGGGAAGGAGGTGCACAGTGGGGTCAGCACGGACCCGCAGCCC*
*CTCAAGGAGCAGCCCGCCCTCAATGACTCCAGATACTGCCTGAGCAGCCGCCTG*
*AGGGTCTCGGCCACCTTCTGGCAGAACCCCGCAACCACTTCCGCTGTCAAGTC*
*CAGTTCTACGGGCTCTCGGAGAATGACGAGTGGACCCAGGATAGGGCCAAACCC*
*GTCACCCAGATCGTCAGCGCCGAGGCCTGGGGTAGAGCAGACTGTGGCTTTACC*
*TCGGTGTCCTACCAGCAAGGGGTCCTGTCTGCCACCATCCTCTATGAGATCCTG*
*CTAGGGAAGGCCACCCTGTATGCTGTGCTGGTCAGCGCCCTTGTGTTGATGGCC*
*ATGGTCAAGAGAAAGGATTTC*AGGGCAAAGCGGAGCGGAAGCGGAGCCACAAAT
TTCTCTCTGCTGAAGCAGGCAGGCGATGTGGAGGAGAACCCTGGACCAATGAT
GAAATCCTTGAGAGTTTTACTAGTGATCCTGTGGCTTCAGTTGAGCT
GGGTTTGGAGCCAACAGAAGGAGGTGGAGCAGAATTCTGGACCCCTC
AGTGTTCCAGAGGGAGCCATTGCCTCTCTCAACTGCACTTACAGTGA
CCGAGGTTCCCAGTCCTTCTTCTGGTACAGACAATATTCTGGGAAAA
GCCCTGAGTTGATAATGTCCATATACTCCAATGGTGACAAAGAAGAT
GGAAGGTTTACAGCACAGCTCAATAAAGCCAGCCAGTATGTTTCTCT

Figure 3 (Cont.)

```
GCTCATCAGAGACTCCCAGCCCAGTGATTCAGCCACCTACCTCTGTG
CCGCCCTGAGGCCTGGTGGCTACAATAAGCTGATTTTTGGAGCAGGG
ACCAGGCTGGCTGTACACCCAAATATCCAGAACCCTGACCCTGCCGTGTAC
CAGCTGAGAGACTCTAAATCCAGTGACAAGTCTGTCTGCCTATTCACCGATTTT
GATTCTCAAACAAATGTGTCACAAAGTAAGGATTCTGATGTGTATATCACAGAC
AAAACTGTGCTAGACATGAGGTCTATGGACTTCAAGAGCAACAGTGCTGTGGCC
TGGAGCAACAAATCTGACTTTGCATGTGCAAACGCCTTCAACAACAGCATTATT
CCAGAAGACACCTTCTTCCCCAGCCCAGAAAGTTCCTGTGATGTCAAGCTGGTC
GAGAAAAGCTTTGAAACAGATACGAACCTAAACTTTCAAAACCTGTCAGTGATT
GGGTTCCGAATCCTCCTCCTGAAAGTGGCCGGGTTTAATCTGCTCATGACGCTG
CGGCTGTGGTCCAGCTGATGA
```

Amino Acid Sequence
```
MDTWLVCWAIFSLLKAGLTEPEVTQTPSHQVTQMGQEVILRCVPISN
HLYFYWYRQILGQKVEFLVSFYNNEISEKSEIFDDQFSVERPDGSNF
TLKIRSTKLEDSAMYFCASSKDYRGGEKLFFGSGTQLSVLEDLNKVFP
PEVAVFEPSEAEISHTQKATLVCLATGFFPDHVELSWWVNGKEVHSGVSTDPQP
LKEQPALNDSRYCLSSRLRVSATFWQNPRNHFRCQVQFYGLSENDEWTQDRAKP
VTQIVSAEAWGRADCGFTSVSYQQGVLSATILYEILLGKATLYAVLVSALVLMA
MVKRKDFRAKRSGSGATNFSLLKQAGDVEENPGPMMKSLRVLLVILWLQLS
WVWSQQKEVEQNSGPLSVPEGAIASLNCTYSDRGSQSFFWYRQYSGK
SPELIMSIYSNGDKEDGRFTAQLNKASQYVSLLIRDSQPSDSATYLC
AALRPGGYNKLIFGAGTRLAVHPNIQNPDPAVYQLRDSKSSDKSVCLFTDF
DSQTNVSQSKDSDVYITDKTVLDMRSMDFKSNSAVAWSNKSDFACANAFNNSII
PEDTFFPSPESSCDVKLVEKSFETDTNLNFQNLSVIGFRILLLKVAGFNLLMTL
RLWSS
```

Figure 4

TRBV2-01+TRAV12-02 Human TCR (codon optimized)

Variable: Native Human (codon optimized)
Constant: Native Human (codon optimized)

Order of sequence
Human Beta Variable (CDR1b, CDR2b, CDR3b
underlined)-Human Beta Constant (italics)- **P2A Cleavage
site (bold)**-Human Alpha Variable (CDR1a, CDR2a, CDR3a
underlined) – Human Alpha Constant (italics.

Nucleotide sequence
ATGGACACCTGGCTGGTGTGCTGGGCCATCTTTTCCCTGCTGAAGGC
AGGACTGACCGAGCCAGAGGTGACCCAGACACCTTCTCACCAGGTGA
CACAGATGGGCCAGGAAGTGATCCTGAGATGCGTGCCAATCAGCAAC
CACCTGTACTTCTATTGGTACCGCCAGATCCTGGGCCAGAAGGTGGA
GTTCCTGGTGTCCTTTTACAACAATGAGATCTCCGAGAAGTCTGAGA
TCTTCGACGATCAGTTTAGCGTGGAGCGGCCCGATGGCTCCAACTTT
ACCCTGAAGATCAGAAGCACAAAGCTGGAGGATTCCGCCATGTATTT
CTGCGCAAGCTCCAAGGACTACAGGGGAGGAGAGAAGCTGTTCTTTG
GCTCTGGCACCCAGCTGAGCGTGCTG*GAGGACCTGAATAAGGTGTTCCCC*
*CCTGAGGTGGCCGTGTTTGAGCCTTCCGAGGCCGAGATCTCTCACACCCAGAAG*
*GCCACCCTGGTGTGCCTGGCAACCGGCTTCTTTCCAGATCACGTGGAGCTGAGC*
*TGGTGGGTGAACGGCAAGGAGGTGCACAGCGGCGTGTCCACCGACCCACAGCCC*
*CTGAAGGAGCAGCCCGCCCTGAATGATAGCAGATATTGCCTGTCTAGCCGGCTG*
*AGAGTGTCCGCCACCTTTTGGCAGAACCCTCGGAATCACTTCAGATGTCAGGTG*
*CAGTTTTACGGCCTGAGCGAGAATGACGAGTGGACCCAGGATAGGGCCAAGCCC*
*GTGACACAGATCGTGTCCGCCGAGGCATGGGGAAGGGCAGACTGCGGCTTCACA*
*TCCGTGTCTTATCAGCAGGGCGTGCTGAGCGCCACCATCCTGTATGAGATCCTG*
*CTGGGCAAGGCCACACTGTACGCCGTGCTGGTGTCCGCCCTGGTGCTGATGGCT*
*ATGGTGAAGCGGAAGGAC*TTT**AGGGCAAAGCGCAGCGGATCCGGAGCAACCAAC
TTCTCTCTGCTGAAGCAGGCCGGCGATGTGGAGGAGAATCCTGGCCCA**ATGAT
GAAGTCCCTGAGAGTGCTGCTGGTCATCCTGTGGCTGCAGCTGTCTT
GGGTGTGGAGCCAGCAGAAGGAGGTGGAGCAGAACTCCGGACCTCTG
TCTGTGCCAGAGGGAGCCATCGCCTCTCTGAATTGTACCTACAGCGA
CAGGGGCTCTCAGAGCTTCTTTTGGTATCGCCAGTACTCTGGCAAGA
GCCCTGAGCTGATCATGTCCATCTATTCTAACGGCGACAAGGAGGAT
GGCAGGTTTACAGCCCAGCTGAATAAGGCCAGCCAGTACGTGTCCCT
GCTGATCCGCGACAGCCAGCCATCCGATTCTGCCACCTATCTGTGCG
CCGCCCTGAGGCCAGGAGGATACAACAAGCTGATCTTCGGAGCAGGA

Figure 4 (Cont.)

ACAAGACTGGCAGTGCACCCAAACATCCAGAATCCCGACCCTGCCGTGTAT
CAGCTGAGGGACTCCAAGTCCTCTGATAAGAGCGTGTGCCTGTTCACCGACTTT
GATTCTCAGACAAACGTGAGCCAGTCCAAGGACAGCGACGTGTACATCACCGAC
AAGACAGTGCTGGATATGCGGAGCATGGACTTCAAGTCTAACAGCGCCGTGGCC
TGGAGCAATAAGTCCGATTTCGCCTGCGCCAATGCCTTTAACAATTCCATCATC
CCTGAGGATACCTTCTTTCCATCTCCCGAGAGCTCCTGTGACGTGAAGCTGGTG
GAGAAGTCTTTCGAGACCGATACAAACCTGAATTTTCAGAACCTGAGCGTGATC
GGCTTCCGGATCCTGCTGCTGAAGGTGGCCGGCTTCAATCTGCTGATGACACTG
AGACTGTGGTCTAGCTGATGA

Amino Acid Sequence

MDTWLVCWAIFSLLKAGLTEPEVTQTPSHQVTQMGQEVILRCVPISNHLYF
YWYRQILGQKVEFLVSFYNNEISEKSEIFDDQFSVERPDGSNFTLKIRSTK
LEDSAMYFCASSKDYRGGEKLFFGSGTQLSV*LEDLNKVFPPEVAVFEPSEAEIS*
*HTQKATLVCLATGFFPDHVELSWWVNGKEVHSGVSTDPQPLKEQPALNDSRYCLSSRLR*
*VSATFWQNPRNHFRCQVQFYGLSENDEWTQDRAKPVTQIVSAEAWGRADCGFTSVSYQQ*
*GVLSATILYEILLGKATLYAVLVSALVLMAMVKRKDF*RAKRSGSGATNFSLLKQAGDVE
ENPGPMMKSLRVLLVILWLQLSWVWSQQKEVEQNSGPLSVPEGAIASLNCTY
SDRGSQSFFWYRQYSGKSPELIMSIYSNGDKEDGRFTAQLNKASQYVSLLI
RDSQPSDSATYLCAALRPGGYNKLIFGAGTRLAVHP*NIQNPDPAVYQLRDSKS*
*SDKSVCLFTDFDSQTNVSQSKDSDVYITDKTVLDMRSMDFKSNSAVAWSNKSDFACANA*
*FNNSIIPEDTFFPSPESSCDVKLVEKSFETDTNLNFQNLSVIGFRILLLKVAGFNLLMT*
*LRLWSS*

Figure 5

TRBV27-01+TRAV13-01 Chimeric TCR

Variable: Native Human
Constant: Mouse (codon optimized)

Order of sequence
Human Beta Variable (CDR1b, CDR2b, CDR3b underlined)-Mouse Beta Constant (italics)- P2A Cleavage site (in bold)- Human Alpha Variable (CDR1a, CDR2a, CDR3a underlined)- Mouse Alpha Constant (italics)

Nucleotide sequence
ATGGGCCCCAGCTCCTTGGCTATGTGGTCCTTTGCCTTCTAGGAGC
AGGCCCCTGGAAGCCCAAGTGACCCAGAACCCAAGATACCTCATCA
CAGTGACTGGAAAGAAGTTAACAGTGACTTGTTCTCAGAATATGAAC
CATGAGTATATGTCCTGGTATCGACAAGACCCAGGGCTGGGCTTAAG
GCAGATCTACTATTCAATGAATGTTGAGGTGACTGATAAGGGAGATG
TTCCTGAAGGGTACAAAGTCTCTCGAAAGAGAAGAGGAATTTCCCC
CTGATCCTGGAGTCGCCCAGCCCCAACCAGACCTCTCTGTACTTCTG
TGCCAGCAGGGGGTTAGCAACTAATGAAAACTGTTTTTTGGCAGTG
*GAACCCAGCTCTCTGTCTTGGAGGACCTGAGGAACGTGACCCCACCTAAGG*
*TGTCCCTGTTCGAGCCTTCTAAGGCCGAGATCGCCAATAAGCAGAAGGCCACCC*
*TGGTGTGCCTGGCAAGGGGCTTCTTTCCAGATCACGTGGAGCTGAGCTGGTGGG*
*TGAACGGCAAGGAGGTGCACTCCGGCGTGTGCACCGACCCACAGGCCTACAAGG*
*AGAGCAATTACTCCTATTGTCTGAGCTCCCGGCTGAGAGTGTCCGCCACATTTT*
*GGCACAACCCCAGGAATCACTTCCGCTGCCAGGTGCAGTTTCACGGCCTGAGCG*
*AGGAGGATAAGTGGCCTGAGGGCTCCCCTAAGCCAGTGACCCAGAACATCTCTG*
*CCGAGGCATGGGGAAGGGCAGACTGTGGAATCACCAGCGCCTCCTATCAGCAGG*
*GCGTGCTGAGCGCCACAATCCTGTACGAGATCCTGCTGGGCAAGGCCACCCTGT*
*ATGCCGTGCTGGTGTCCACACTGGTGGTCATGGCTATGGTGAAGCGGAAGAACT*
CTAGGGCAAAGCGGAGCGGAAGCGGAGCCACAAATTTCTCTCTGCTGAAGCAGG
CAGGCGATGTGGAGGAGAACCCTGGACCAATGACATCCATTCGAGCTGTAT
TTATATTCCTGTGGCTGCAGCTGGACTTGGTGAATGGAGAGAATGTG
GAGCAGCATCCTTCAACCCTGAGTGTCCAGGAGGGAGACAGCGCTGT
TATCAAGTGTACTTATTCAGACAGTGCCTCAAACTACTTCCCTTGGT
ATAAGCAAGAACTTGGAAAAGGACCTCAGCTTATTATAGACATTCGT
TCAAATGTGGGCGAAAGAAAGACCAACGAATTGCTGTTACATTGAA
CAAGACAGCCAAACATTTCTCCCTGCACATCACAGAGACCCAACCTG
AAGACTCGGCTGTCTACTTCTGTGCAGCAAGTAAAGGAAACACACCT
CTTGTCTTTGGAAAGGGCACAAGACTTTCTGTGATTGCA*AACATCCAG*

Figure 5 (Cont.)

AATCCAGAGCCCGCCGTGTATCAGCTGAAGGACCCAAGATCCCAGGATTCTACC
CTGTGCCTGTTCACAGACTTTGATTCTCAGATCAATGTGCCCAAGACAATGGAG
AGCGGCACCTTCATCACAGACAAGTGCGTGCTGGATATGAAGGCTATGGACTCC
AAGTCTAACGGCGCCATCGCCTGGAGCAATCAGACCTCCTTCACATGCCAGGAT
ATCTTTAAGGAGACAAACGCCACATACCCTTCTAGCGACGTGCCATGTGATGCC
ACCCTGACAGAGAAGAGCTTCGAGACAGACATGAACCTGAATTTTCAGAATCTG
CTGGTCATCGTGCTGCGGATCCTGCTGCTGAAGGTGGCTGGGTTTAATCTGCTG
ATGACACTGCGACTGTGGAGTAGCTGATGA

Amino Acid Sequence

MGPQLLGYVVLCLLGAGPLEAQVTQNPRYLITVTGKKLTVTCSQNMN
HEYMSWYRQDPGLGLRQIYYSMNVEVTDKGDVPEGYKVSRKEKRNFP
LILESPSPNQTSLYFCASRGLATNEKLFFGSGTQLSVLEDLRNVTPPK
VSLFEPSKAEIANKQKATLVCLARGFFPDHVELSWWVNGKEVHSGVCTDPQAYK
ESNYSYCLSSRLRVSATFWHNPRNHFRCQVQFHGLSEEDKWPEGSPKPVTQNIS
AEAWGRADCGITSASYQQGVLSATILYEILLGKATLYAVLVSTLVVMAMVKRKN
SRAKRSGSGATNFSLLKQAGDVEENPGPMTSIRAVFIFLWLQLDLVNGENV
EQHPSTLSVQEGDSAVIKCTYSDSASNYFPWYKQELGKGPQLIIDIR
SNVGEKKDQRIAVTLNKTAKHFSLHITETQPEDSAVYFCAASKGNTP
LVFGKGTRLSVIANIQNPEPAVYQLKDPRSQDSTLCLFTDFDSQINVPKTME
SGTFITDKCVLDMKAMDSKSNGAIAWSNQTSFTCQDIFKETNATYPSSDVPCDA
TLTEKSFETDMNLNFQNLLVIVLRILLLKVAGFNLLMTLRLWSS

Figure 6

<u>TRBV27-01+TRAV13-01 Chimeric TCR (codon optimized)</u>

Variable: <u>Human Codon optimized</u>
Constant: <u>Mouse (codon optimized)</u>

<u>Order of sequence</u>
Human Beta Variable (CDR1b, CDR2b, CDR3b
underlined)-Mouse Beta Constant (italics)- **P2A cleavage
site (in bold)**-Human Alpha Variable (CDR1a, CDR2a,
CDR3a underlined)- Mouse Alpha Constant (italics).

<u>Nucleotide sequence</u>
ATGGGACCACAGCTGCTGGGATACGTGGTGCTGTGCCTGCTGGGAGC
AGGACCACTGGAGGCACAGGTGACCCAGAACCCTAGATATCTGATCA
CCGTGACAGGCAAGAAGCTGACCGTGACATGTAGCCAGAAC<u>ATGAAT
CACGAGTACATG</u>TCCTGGTATCGGCAGGATCCTGGCCTGGGCCTGAG
ACAGATCTACTAT<u>AGCATGAATGTGGAGGTGACCGACAAGGGCGATG
TGCCTGAGGGCTACAAGGTGTCCCGG</u>AAGGAGAAGAGAAACTTCCCA
CTGATCCTGGAGAGCCCATCCCCAATCAGACCTCTCTGTATTTT<u>TG
CGCAAGCAGGGGACTGGCAACCAATGAGAAGCTGTTCTTTGGCTCCG
GCACACAGCTGTCTGTGCTG</u>*GAGGACCTGAGAAACGTGACCCCCCTAAGG*
*TGAGCCTGTTCGAGCCCTCCAAGGCCGAGATCGCCAATAAGCAGAAGGCCACCC*
*TGGTGTGCCTGGCAAGGGGCTTCTTTCCTGATCACGTGGAGCTGTCTTGGTGGG*
*TGAACGGCAAGGAGGTGCACAGCGGCGTGTGCACCGACCCACAGGCCTACAAGG*
*AGTCTAATTACAGCTATTGTCTGAGCTCCCGGCTGAGAGTGTCCGCCACATTTT*
*GGCACAACCCAAGGAATCACTTCCGCTGCCAGGTGCAGTTTCACGGCCTGTCTG*
*AGGAGGATAAGTGGCCAGAGGGAAGCCCTAAGCCAGTGACCCAGAACATCTCCG*
*CCGAGGCATGGGGAAGGGCAGACTGTGGAATCACCTCTGCCAGCTATCAGCAGG*
*GCGTGCTGAGCGCCACAATCCTGTACGAGATCCTGCTGGGCAAGGCCACCCTGT*
*ATGCCGTGCTGGTGAGCACACTGGTGGTCATGGCTATGGTGAAGAGGAAGAACT*
*CC***AGGGCAAAGCGGAGCGGATCTGGAGCCACCAATTTCTCTCTGCTGAAGCAGG
CAGGCGATGTGGAGGAGAATCCAGGACCT**ATGACATCCATCCGCGCCGTGT
TCATCTTTCTGTGGCTGCAGCTGGACCTGGTGAACGGCGAGAATGTG
GAGCAGCACCCTCCACCCTGTCTGTGCAGGAGGGCGATAGCGCCGT
GATCAAGTGCACATACAGCGACTCCGCCTCTAAC<u>TACTTCCCCTGGT
ATAAGCAGGAGCTGGGCAAGGGCCCCAGCTGATCATCGATATCAGG</u>
<u>TCTAACGTGGGCGAGAAGAAGGACCAGCGCATCGCCGTGACCCTGAA</u>
TAAGACAGCCAAGCACTTTAGCCTGCACATCACCGAGACACAGCCCG
AGGATTCCGCCGTGTACTTCTGT<u>GCCGCCTCTAAGGGCAACACCCT</u>

Figure 6 (Cont.)

CTGGTGTTTGGCAAGGGCACAAGGCTGTCCGTGATCGCCAACATCCAG
AATCCAGAGCCCGCCGTGTATCAGCTGAAGGACCCTCGCAGCCAGGATTCCACC
CTGTGCCTGTTCACAGACTTTGATTCCCAGATCAATGTGCCAAAGACAATGGAG
TCTGGCACCTTCATCACAGACAAGTGCGTGCTGGATATGAAGGCTATGGACAGC
AAGTCCAACGGCGCCATCGCCTGGTCTAATCAGACCAGCTTCACATGCCAGGAT
ATCTTTAAGGAGACCAACGCCACATACCCTTCTAGCGACGTGCCATGTGATGCC
ACCCTGACAGAGAAGAGCTTCGAGACCGACATGAACCTGAATTTTCAGAACCTG
CTGGTCATCGTGCTGCGGATCCTGCTGCTGAAGGTGGCCGGCTTTAATCTGCTG
ATGACACTGAGACTGTGGTCCTCTTGATGA

Amino Acid Sequence
MGPQLLGYVVLCLLGAGPLEAQVTQNPRYLITVTGKKLTVTCSQNMN
HEYMSWYRQDPGLGLRQIYYSMNVEVTDKGDVPEGYKVSRKEKRNFP
LILESPSPNQTSLYFCASRGLATNEKLFFGSGTQLSVLEDLRNVTPPK
VSLFEPSKAEIANKQKATLVCLARGFFPDHVELSWWVNGKEVHSGVCTDPQAYK
ESNYSYCLSSRLRVSATFWHNPRNHFRCQVQFHGLSEEDKWPEGSPKPVTQNIS
AEAWGRADCGITSASYQQGVLSATILYEILLGKATLYAVLVSTLVVMAMVKRKN
SRAKRSGSGATNFSLLKQAGDVEENPGPMTSIRAVFIFLWLQLDLVNGENV
EQHPSTLSVQEGDSAVIKCTYSDSASNYFPWYKQELGKGPQLIIDIR
SNVGEKKDQRIAVTLNKTAKHFSLHITETQPEDSAVYFCAASKGNTP
LVFGKGTRLSVIANIQNPEPAVYQLKDPRSQDSTLCLFTDFDSQINVPKTME
SGTFITDKCVLDMKAMDSKSNGAIAWSNQTSFTCQDIFKETNATYPSSDVPCDA
TLTEKSFETDMNLNFQNLLVIVLRILLLKVAGFNLLMTLRLWSS

Figure 7

TRBV27-01+TRAV13-01 Human TCR

Variable: Native Human
Constant: Native Human

Order of sequence
Human Beta Variable (CDR1b, CDR2b, CDR3b underlined)-Human Beta Constant (italics)- P2A Cleavage site (in bold)-Human Alpha Variable (CDR1a, CDR2a, CDR3a underlined)- Human Alpha Constant (italics).

Nucleotide sequence
ATGGGCCCCAGCTCCTTGGCTATGTGGTCCTTTGCCTTCTAGGAGC
AGGCCCCCTGGAAGCCCAAGTGACCCAGAACCCAAGATACCTCATCA
CAGTGACTGGAAAGAAGTTAACAGTGACTTGTTCTCAGAATATGAAC
CATGAGTATATGTCCTGGTATCGACAAGACCCAGGGCTGGGCTTAAG
GCAGATCTACTATTCAATGAATGTTGAGGTGACTGATAAGGGAGATG
TTCCTGAAGGGTACAAAGTCTCTCGAAAAGAGAAGAGGAATTTCCCC
CTGATCCTGGAGTCGCCCAGCCCCAACCAGACCTCTCTGTACTTCTG
TGCCAGCAGGGGGTTAGCAACTAATGAAAACTGTTTTTTGGCAGTG
*GAACCCAGCTCTCTGTCTTGGAGGACCTGAACAAGGTGTTCCCACCCGAGG*
*TCGCTGTGTTTGAGCCATCAGAAGCAGAGATCTCCCACACCCAAAAGCCACAC*
*TGGTGTGCCTGGCCACAGGCTTCTTCCCCGACCACGTGGAGCTGAGCTGGTGGG*
*TGAATGGGAAGGAGGTGCACAGTGGGGTCAGCACGGACCCGCAGCCCCTCAAGG*
*AGCAGCCCGCCCTCAATGACTCCAGATACTGCCTGAGCAGCCGCCTGAGGGTCT*
*CGGCCACCTTCTGGCAGAACCCCCGCAACCACTTCCGCTGTCAAGTCCAGTTCT*
*ACGGGCTCTCGGAGAATGACGAGTGGACCCAGGATAGGGCCAAACCCGTCACCC*
*AGATCGTCAGCGCCGAGGCCTGGGGTAGAGCAGACTGTGGCTTTACCTCGGTGT*
*CCTACCAGCAAGGGGTCCTGTCTGCCACCATCCTCTATGAGATCCTGCTAGGGA*
*AGGCCACCCTGTATGCTGTGCTGGTCAGCGCCCTTGTGTTGATGGCCATGGTCA*
*AGAGAAAGGATTTC*AGGGCAAAGCGGAGCGGAAGCGGAGCCACAAATTTCTCTC
TGCTGAAGCAGGCAGGCGATGTGGAGGAGAACCCTGGACCAATGACATCCAT
TCGAGCTGTATTTATATTCCTGTGGCTGCAGCTGGACTTGGTGAATG
GAGAGAATGTGGAGCAGCATCCTTCAACCCTGAGTGTCCAGGAGGGA
GACAGCGCTGTTATCAAGTGTACTTATTCAGACAGTGCCTCAAACTA
CTTCCCTTGGTATAAGCAAGAACTTGGAAAAGGACCTCAGCTTATTA
TAGACATTCGTTCAAATGTGGGCGAAAGAAGACCAACGAATTGCT
GTTACATTGAACAAGACAGCCAAACATTTCTCCCTGCACATCACAGA
GACCCAACCTGAAGACTCGGCTGTCTACTTCTGTGCAGCAAGTAAAG
GAAACACACCTCTTGTCTTTGGAAAGGGCACAAGACTTTCTGTGATT

Figure 7 (Cont.)

GCAAATATCCAGAACCCTGACCCTGCCGTGTACCAGCTGAGAGACTCTAAATCC
AGTGACAAGTCTGTCTGCCTATTCACCGATTTTGATTCTCAAACAAATGTGTCA
CAAAGTAAGGATTCTGATGTGTATATCACAGACAAAACTGTGCTAGACATGAGG
TCTATGGACTTCAAGAGCAACAGTGCTGTGGCCTGGAGCAACAAATCTGACTTT
GCATGTGCAAACGCCTTCAACAACAGCATTATTCCAGAAGACACCTTCTTCCCC
AGCCCAGAAAGTTCCTGTGATGTCAAGCTGGTCGAGAAAGCTTTGAAACAGAT
ACGAACCTAAACTTTCAAAACCTGTCAGTGATTGGGTTCCGAATCCTCCTCCTG
AAAGTGGCCGGGTTTAATCTGCTCATGACGCTGCGGCTGTGGTCCAGCTGATGA

Amino Acid Sequence

MGPQLLGYVVLCLLGAGPLEAQVTQNPRYLITVTGKKLTVTCSQNMNHEYM
SWYRQDPGLGLRQIYYSMNVEVTDKGDVPEGYKVSRKEKRNFPLILESPSP
NQTSLYFCASRGLATNEKLFFGSGTQLSVLEDLNKVFPPEVAVFEPSEAEISHT
QKATLVCLATGFFPDHVELSWWVNGKEVHSGVSTDPQPLKEQPALNDSRYCLSSRLRVS
ATFWQNPRNHFRCQVQFYGLSENDEWTQDRAKPVTQIVSAEAWGRADCGFTSVSYQQGV
LSATILYEILLGKATLYAVLVSALVLMAMVKRKDF**RAKRSGSGATNFSLLKQAGDVEEN
PGP**MTSIRAVFIFLWLQLDLVNGENVEQHPSTLSVQEGDSAVIKCTYSDSA
SNYFPWYKQELGKGPQLIIDIRSNVGEKKDQRIAVTLNKTAKHFSLHITET
QPEDSAVYFCAASKGNTPLVFGKGTRLSVIANIQNPDPAVYQLRDSKSSDKSVC
LFTDFDSQTNVSQSKDSDVYITDKTVLDMRSMDFKSNSAVAWSNKSDFACANAFNNSII
PEDTFFPSPESSCDVKLVEKSFETDTNLNFQNLSVIGFRILLLKVAGFNLLMTLRLWSS

Figure 8

TRBV27-01+TRAV13-01 Human TCR (Codon Optimized)

Variable: Native Human Codon optimized
Constant: Native Human Codon optimized

Order of sequence
Human Beta Variable (CDR1b, CDR2b, CDR3b underlined)-Human Beta Constant (italics)- P2A cleavage site (in bold)-Human Alpha Variable (CDR1a, CDR2a, CDR3a underlined)- Human Alpha Constant(italics).

Nucleotide sequence
ATGGGACCACAGCTGCTGGGATACGTGGTGCTGTGCCTGCTGGGAGC
AGGACCACTGGAGGCACAGGTGACCCAGAACCCTCGGTATCTGATCA
CCGTGACAGGCAAGAAGCTGACCGTGACATGTTCCCAGAAC<u>ATGAAT
CACGAGTACATG</u>TCTTGGTATAGGCAGGACCCTGGACTGGGACTGAG
ACAGATCTACTAT<u>TCCATGAATGTGGAG</u>GTGACCGACAAGGGCGATG
TGCCTGAGGGCTACAAGGTGTCTCGGAAGGAGAAGAGAAACTTTCCA
CTGATCCTGGAGTCTCCAAGCCCCAATCAGACATCCCTGTATTTC<u>TG
CGCCTCTAGAGGCCTGGCCACCAACGAGAAGCTGTTCTTTGGCAGCG</u>
GCACAGCTGTCCGTGCTG*GAGGACCTGAATAAGGTGTTCCCCCCTGAGG*
*TGGCCGTGTTTGAGCCATCTGAGGCCGAGATCAGCCACACCCAGAAGGCCACCC*
*TGGTGTGCCTGGCAACCGGCTTCTTTCCCGATCACGTGGAGCTGTCCTGGTGGG*
*TGAACGGCAAGGAGGTGCACAGCGGCGTGTCCACAGACCCTCAGCCACTGAAGG*
*AGCAGCCTGCCCTGAATGATTCCAGGTACTGCCTGAGCTCCCGGCTGAGAGTGT*
*CTGCCACCTTTTGGCAGAACCCAAGGAATCACTTCCGCTGTCAGGTGCAGTTTT*
*ATGGCCTGAGCGAGAACGACGAGTGGACCCAGGATCGGGCCAAGCCAGTGACAC*
*AGATCGTGTCCGCCGAGGCATGGGGAAGAGCAGACTGCGGCTTCACATCCGTGT*
*CTTATCAGCAGGGCGTGCTGTCTGCCACCATCCTGTACGAGATCCTGCTGGGCA*
*AGGCCACACTGTATGCCGTGCTGGTGAGCGCCCTGGTGCTGATGGCTATGGTGA*
*AGAGGAAGGACTTT*AGGGCAAAGCGCAGCGGATCCGGAGCAACCAACTTCTCTC
TGCTGAAGCAGGCAGGCGATGTGGAGGAGAATCCAGGACCTATGACAAGCAT
CCGCGCCGTGTTCATCTTTCTGTGGCTGCAGCTGGATCTGGTGAACG
GCGAGAATGTGGAGCAGCACCCTTCTACCCTGAGCGTGCAGGAGGGC
GATAGCGCCGTGATCAAGTGTACATACTCT<u>GACAGCGCCTCCAACTA
CTTTCCTGGTATAAGCAGGAGCTGGGCAAGGGCCCCCAGCTGATCA
TCGATATCAGGTCCAACGTGGGC</u>GAGAAGAAGGACCAGCGCATCGCC
GTGACCCTGAATAAGACAGCCAAGCACTTCAGCCTGCACATCACCGA
GACACAGCCCGAGGACTCTGCCGTGTACTTT<u>TGCGCCGCCAGCAAGG</u>

Figure 8 (Cont.)

GCAATACCCCTCTGGTGTTCGGCAAGGGCACACGGCTGTCCGTGATC
GCCAACATCCAGAATCCAGATCCCGCCGTGTATCAGCTGAGAGACAGCAAGTCT
AGCGATAAGAGCGTGTGCCTGTTCACCGACTTTGATAGCCAGACAAACGTGTCT
CAGAGCAAGGACTCCGACGTGTACATCACCGACAAGACAGTGCTGGATATGCGG
AGCATGGACTTTAAGTCCAACTCTGCCGTGGCCTGGTCCAATAAGTCTGACTTC
GCCTGCGCCAATGCCTTTAACAATTCTATCATCCCCGAGGATACCTTCTTTCCT
AGCCCAGAGTCCTCTTGTGACGTGAAGCTGGTGGAGAAGAGCTTCGAGACCGAT
ACAAACCTGAATTTTCAGAACCTGTCCGTGATCGGCTTCAGGATCCTGCTGCTG
AAGGTGGCCGGCTTCAATCTGCTGATGACCCTGCGCCTGTGGAGCTCCTGATGA

Amino Acid Sequence
MGPQLLGYVVLCLLGAGPLEAQVTQNPRYLITVTGKKLTVTCSQNMN
HEYMSWYRQDPGLGLRQIYYSMNVEVTDKGDVPEGYKVSRKEKRNFP
LILESPSPNQTSLYFCASRGLATNEKLFFGSGTQLSVL*EDLNKVFPPE*
*VAVFEPSEAEISHTQKATLVCLATGFFPDHVELSWWVNGKEVHSGVSTDPQPLK*
*EQPALNDSRYCLSSRLRVSATFWQNPRNHFRCQVQFYGLSENDEWTQDRAKPVT*
*QIVSAEAWGRADCGFTSVSYQQGVLSATILYEILLGKATLYAVLVSALVLMAMV*
*KRKDF*RAKRSGSGATNFSLLKQAGDVEENPGPMTSIRAVFIFLWLQLDLVN
GENVEQHPSTLSVQEGDSAVIKCTYSDSASNYFPWYKQELGKGPQLI
IDIRSNVGEKKDQRIAVTLNKTAKHFSLHITETQPEDSAVYFCAASK
GNTPLVFGKGTRLSVI*ANIQNPDPAVYQLRDSKSSDKSVCLFTDFDSQTNVS*
*QSKDSDVYITDKTVLDMRSMDFKSNSAVAWSNKSDFACANAFNNSIIPEDTFFP*
*SPESSCDVKLVEKSFETDTNLNFQNLSVIGFRILLLKVAGFNLLMTLRLWSS*

FIGURE 10

| Sequence | Sequence Identifier |
|---|---|
| SNHLY | 1 |
| FYNNEI | 2 |
| CASSKDYRGGEKLFF | 3 |
| MDTWLVCWAIFSLLKAGLTEPEVTQTPSHQVTQMGQEVILRCVPI | 4 |
| FYWYRQILGQKVEFLVS | 5 |
| SEKSEIFDDQFSVERPDGSNFTLKIRSTKLEDSAMYF | 6 |
| GSGTQLSVL | 7 |
| EDLRNVTPPKVSLFEPSKAEIANKQKATLVCLARGFFPDHVELSWWVNGKEVHSGVCTDP QAYKESNYSYCLSSRLRVSATFWHNPRNHFRCQVQFHGLSEEDKWPEGSPKPVTQNISAE AWGRADCGITSASYQQGVLSATILYEILLGKATLYAVLVSTLVVMAVKRKNS | 8 |
| MDTWLVCWAIFSLLKAGLTEPEVTQTPSHQVTQMGQEVILRCVPISNHLYFYWYRQILGQ KVEFLVSFYNNEISEKSEIFDDQFSVERPDGSNFTLKIRSTKLEDSAMYFCASSKDYRGGEK LFFGSGTQLSVL | 47 |
| MDTWLVCWAIFSLLKAGLTEPEVTQTPSHQVTQMGQEVILRCVPISNHLYFYWYRQILGQ KVEFLVSFYNNEISEKSEIFDDQFSVERPDGSNFTLKIRSTKLEDSAMYFCASSKDYRGGEK LFFGSGTQLSVLEDLRNVTPPKVSLFEPSKAEIANKQKATLVCLARGFFPDHVELSWWVN GKEVHSGVCTDPQAYKESNYSYCLSSRLRVSATFWHNPRNHFRCQVQFHGLSEEDKWPE GSPKPVTQNISAEAWGRADCGITSASYQQGVLSATILYEILLGKATLYAVLVSTLVVMAM VKRKNS | 9 |
| DRGSQS | 10 |
| IYSNGD | 11 |
| CAALRPGGYNKLIF | 12 |
| MMKSLRVLLVILWLQLSWVWSQQKEVEQNSGPLSVPEGAIASLNCTYS | 13 |
| FFWYRQYSGKSPELIMS | 14 |
| KEDGRFTAQLNKASQYVSLLIRDSQPSDSATYL | 15 |
| GAGTRLAVHP | 16 |
| NIQNPEPAVYQLKDPRSQDSTLCLFTDFDSQINVPKTMESGTFITDKCVLDMKAMDSKSNG | 17 |

FIGURE 10 (Cont.)

| Sequence | No. |
|---|---|
| AIAWSNQTSFTCQDIFKETNATYPSSDVPCDATLTEKSFETDMNLNFQNLLVIVLRILLLKVA GFNLLMTLRLWSS | |
| MMKSLRVLLVILWLQLSWVWSQQKEVEQNSGPLSVPEGAIASLNCTYSDRGSQSFFWYRQ YSGKSPELIMSIYSNGDKEDGRFTAQLNKASQYVSLLIRDSQPSDSATYLCAALRPGGYNKLI FGAGTRLAVHP | 45 |
| MMKSLRVLLVILWLQLSWVWSQQKEVEQNSGPLSVPEGAIASLNCTYSDRGSQSFFWYRQ YSGKSPELIMSIYSNGDKEDGRFTAQLNKASQYVSLLIRDSQPSDSATYLCAALRPGGYNKLI FGAGTRLAVHPNIQNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETDMNLNFQNLLVIV LRILLLKVAGFNLLMTLRLWSS | 18 |
| EDLNKVFPPEVAVFEPSEAEISHTQKATLVCLATGFFPDHVELSWWVNGKEVHSGVSTDPQP LKEQPALNDSRYCLSSRLRVSATFWQNPRNHFRCQVQFYGLSENDEWTQDRAKPVTQIVSAE AWGRADCGFTSVSYQQGVLSATILYEILLGKATLYAVLVSALVLMAMVKRKDF | 19 |
| MDTWLVCWAIFSLLKAGLTEPEVTQTPSHQVIQMGQEVILRCVPISNHLYFYWYRQILGQKV EFLVSFYNNEISEKSEIFDDQFSVERPDGSNFTLKIRSTKLEDSAMYFCASSKDYRGGEKLFFGS GTQLSVLEDLNKVFPPEVAVFEPSEAEISHTQKATLVCLATGFFPDHVELSWWVNGKEVHSGV STDPQPLKEQPALNDSRYCLSSRLRVSATFWQNPRNHFRCQVQFYGLSENDEWTQDRAKPVT QIVSAEAWGRADCGFTSVSYQQGVLSATILYEILLGKATLYAVLVSALVLMAMVKRKDF | 20 |
| NIQNPDPAVYQLRDSKSSDKSVCLFTDFDSQINVSQSKDSDVYITDKTVLDMRSMDFKSNSAVA WSNKSDFACANAFNNSIIPEDTFFPSPESSCDVKLVEKSFETDTNLNFQNLSVIGFRILLKVAGFN LLMTLRLWSS | 21 |
| MMKSLRVLLVILWLQLSWVWSQQKEVEQNSGPLSVPEGAIASLNCTYSDRGSQSFFWYRQYSG KSPELIMSIYSNGDKEDGRFTAQLNKASQYVSLLIRDSQPSDSATYLCAALRPGGYNKLIFGAGT RLAVHPNIQNPDPAVYQLRDSKSSDKSVCLFTDFDSQINVSQSKDSDVYITDKTVLDMRSMDFK SNSAVAWSNKSDFACANAFNNSIIPEDTFFPSPESSCDVKLVEKSFETDTNLNFQNLSVIGFRILLL KVAGFNLLMTLRLWSS | 22 |
| MNHEY | 23 |
| SMNVEV | 24 |
| CASRGLATNEKLFF | 25 |
| MGPQLLGYVVLCLLGAGPLEAQVTQNPRYLITVTGKKLTVTCSQN | 26 |

FIGURE 10 (Cont.)

| Sequence | SEQ ID NO |
|---|---|
| MSWYRQDPGLGLRQIYY | 27 |
| TDKGDVPEGYKVSRKEKRNFPLILESPSPNQTSLYF | 28 |
| GSGTQLSVL | 29 |
| EDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS | 30 |
| MGPQLLGYVLCLLGAGPLEAQVTQNPRYLITVGKKLTVTCSQNMNHEYMSWYRQDPGLGLRQIYYSMNVEVTDKGDVPEGYKVSRKEKRNFPLILESPSPNQTSLYFCASRGLATNEKLFFGSGTQLSVL | 48 |
| MGPQLLGYVLCLLGAGPLEAQVTQNPRYLITVGKKLTVTCSQNMNHEYMSWYRQDPGLGLRQIYYSMNVEVTDKGDVPEGYKVSRKEKRNFPLILESPSPNQTSLYFCASRGLATNEKLFFGSGTQLSVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS | 31 |
| DSASNY | 32 |
| IRSNVGE | 33 |
| CAASKGNTPLVF | 34 |
| MTSIRAVFIFLWLQLDLVNGENVEQHPSTLSVQEGDSAVIKCTYS | 35 |
| FPWYKQELGKGPQLIID | 36 |
| KKDQRIAVTLNKTAKHFSLHITETQPEDSAVYF | 37 |
| GKGTRLSVIA | 38 |
| NIQNPEPAVYQLKDPRSQDSTLCLFTDFDSQINVPKTMESGTFITDKCVLDMKAMDSKSNGAIAWSNQTSFTCQDIFKETNATYPSSDVPCDAILTEKSFETDMNLNFQNLLVIVLRILLLKVAGFNLLMTLRLWSS | 39 |
| MTSIRAVFIFLWLQLDLVNGENVEQHPSTLSVQEGDSAVIKCTYSDSASNYFPWYKQELGKGPQLIIDIRSNVGEKKDQRIAVTLNKTAKHFSLHITETQPEDSAVYFCAASKGNTPLVFGKGTRLSVIA | 46 |
| MTSIRAVFIFLWLQLDLVNGENVEQHPSTLSVQEGDSAVIKCTYSDSASNYFPWYKQELGKGPQLIIDIRSNVGEKKDQRIAVTLNKTAKHFSLHITETQPEDSAVYFCAASKGNTPLVFGKGTRLSVIANIQNPEPAVYQLKDPRSQDSTLCLFTDFDSQINVPKTMESGTFITDKCVLDMKA | 40 |

FIGURE 10 (Cont.)

| Sequence | No. |
|---|---|
| MDSKSNGALAWSNQTSFTCQDIFKETNATYPSSDVPCDATLTEKSFETDMNLNFQNLLVIV LRILLLKVAGFNLLMTLRLWSS | |
| EDLNKVFPPEVAVFEPSEAEISHTQKATLVCLATGFFPDHVELSWWVNGKEVHSGVSTDPQ PLKEQPALNDSRYCLSSRLRVSATFWQNPRNHFRCQVQFYGLSENDEWTQDRAKPVTQIVS AEAWGRADCGFTSVSYQQGVLSATILYEILLGKATLYAVLVSALVLMAMVKRKDF | 41 |
| MGPQLLGYVLCLLGAGPLEAQVTQNPRYLITVTGKKLTVTCSQNMNHEYMSWYRQDPG LGLRQIYYSMNVEVTDKGDVPEGYKVSRKEKRNFPLILESPSPNQTSLYFCASRGLATNEKL FFGSGTQLSVLEDLNKVFPPEVAVFEPSEAEISHTQKATLVCLATGFFPDHVELSWWVNGKE VHSGVSTDPQPLKEQPALNDSRYCLSSRLRVSATFWQNPRNHFRCQVQFYGLSENDEWTQD RAKPVTQIVSAEAWGRADCGFTSVSYQQGVLSATILYEILLGKATLYAVLVSALVLMAMVKRKDF | 42 |
| NIQNPDPAVYQLRDSKSSDKSVCLFTDFDSQTNVSQSKDSDVYITDKTVLDMRSMDFKSNSA VAWSNKSDFACANAFNNSIIPEDTFFPSPESSCDVKLVEKSFETDTNLNFQNLSVIGFRILLLK VAGFNLLMTLRLWSS | 43 |
| MTSIRAVFIFLWLQLDLVNGENVEQHPSTLSVQEGDSAVIKCTYSDSASNYFPWYKQELGK GPQLIIDIRSNVGEKKDQRIAVTLNKTAKHFSLHITETQPEDSAVYFCAASKGNTPLVFGKGT RLSVIANIQNPDPAVYQLRDSKSSDKSVCLFTDFDSQTNVSQSKDSDVYITDKTVLDMRSMD FKSNSAVAWSNKSDFACANAFNNSIIPEDTFFPSPESSCDVKLVEKSFETDTNLNFQNLSVIG FRILLLKVAGFNLLMTLRLWSS | 44 |

FIGURE 11A

Nucleotide sequence encoding beta chain of TRBV2-01 + TRAV12-02 chimeric TCR, with human beta variable region in larger font. CDR1, CDR2, CDR3 underlined, and mouse beta constant in italics Nucleotide sequence ATGGATACCTGGCTCGTCGTATGCTGGGCAATTTTTAGTCTCTTGAAAGCAGGACTCACAGAACCTGAAGTCACC
CAGACTCCCAGCCATCAGGTCACACAGATGGGACAGGAAGTGATCTTGCGCTGTGTCCCCATCTCTAATCAC
TTATACTTCTATTGGTACAGACAAATCTTGGGGCAGAAAGTCGAGTTTCTCGGTTTCCTTTTATAATAATGAA
ATCTCAGAGAAGTCGAAATATTCGATGATCAATTCTCAGTTGAAAGGCCTGATGGATCAAATTTCACTCTG
AAGATCCGGTCCACAAAGCTGGAGGACTCAGCCATGTACTTCTGTGCCAGCAGTAAAGACTACCGGGGAGGT
GAAAAACTGTTTTTTGGCAGTGGAACCCAGCTCTCTTGGAGGACCTGAGAAACGTGACCACCCCTAAGGTGAG
*CCTGTTCGAGCCCCTCCAAGGCCGAGATCGGCCAATAAGCAGGAGGCCACCCTGGTGTGCCTGGCAAGGGGGTTCTTTCCTGATCA*
*CGTGGAGCTGTCTTGGTGGGTGAACGGCAAGGAGGTGCACAGCGGCGTGTCCACCGACCCCCAGCCCCTATAAGGAGAGCAATTA*
*TTCCTACTGTGTCTCTGTCTAGCCCGGTTGAGAGTGAGCGGCCCACATTTTGGCACAACCCTCGGAATCACTTCAGATGCCAGTGCCAGTT*
*TCACGGCCCTGTCTGAGGAGGATAAGTGGCCAGAGGGCAGCCCCAAAGCCAGTGACCCGCCAGAACATCTCCGCGAGGCATGGGAAG*
*AGCCAGACTGTGTGGCATCACCAGCGCCTCCTACCAGCAGGGCGTGCTGTCCGCCACAATCCTGTATGGCCTATGGCTCATGGCCTATGGGTCGTGGTCAG*
*CACCCTGTACCGCCGTGCTCGGTCGGTGAGCAACGTGGTCGGTCATGGCCTATGGGTCGTGGTGAGCAACGTGGTGAGCAACTCC*

FIGURE 11B

Nucleotide sequence encoding alpha chain of TRBV2-01 + TRAV12-02 chimeric TCR including human alpha variable region in larger font, CDR1, CDR2, CDR3 underlined, and mouse alpha constant in italics

ATGGATGAAATCCTTGAGAGTTTTACTAGTGAGTGATCCTGTGGCTTCAGTTGAGCTTGGGAGCCAACAGAAAG

GAGGTGGAGCAGAATTCTGGACCCCTCAGTGTTCCAGAGGGAGCCATTGCCTCTCAACTGCACTTACAGT

GACCGAGGTTCCCAGTCCTTCTGGTACAGACAATATTCTGGAAAAGCCCTGAGTGGTGATAAGTCCATA

TACTCCAATGGTGACAAAGAAGATGGAAGGTTTACAGCACAGCTCAATAAAGCCAGCCAGTATGTTTCTCTG

CTCATCAGAGACTCCCAGCCCAGTGATTCAGCCAGGCTGGCTGTGCTGGCTGTACACCCAGAATCCAGAGCCCGGTATCAGCT

AAGCTGATTTTTGGGAGGCAGGAGGCAGGATTCTACCCTGTGCCGTTCCAGATGAATGGAAGGCCATGGGAGCCCTGGGGCCCATCGGCCTCGAGCAATCA

GAAGGACCCAGAGATCCCAGAGATTCTACCCTGTGCCGTTCACAGATCCCTGGGGCCCATCGGCCTCGAGCAATCA

CGGCACCTTCATCACAGACAAGTGCGTGCTGGATATGAAGGCCATGGACTCCAAGTCTAACGGCGCCGTGGGCCCATCGGCCTCGAGCAATCA

GACCTCCTTCACATGCCAGGATATCTTTAAGGAGACAAACGCCACATACCCTTCTAGCGACGTGCCATGTGATGCCACCCTGAC

AGAGGAAGAGCTTCGAGACAGAACATGAACCTGAATTTTCAGAATCCTGCTGGTCATCGTGGTCATCGTGCTGCTGGGATCCTGCTGCTGGGATCCTGCTGCTGGGATGGAAGGTGGC

TGGGTTTAATCTGCTGATGACACTGCGACTGGGAGTAGCTGATGA

FIGURE 12A

Codon optimized nucleotide sequence encoding beta chain of TRBV2-01+TRAV12-02 Chimeric TCR, with human variable region in larger font, CDR1, CDR2, CDR3 underlined, and mouse beta constant in italics ATGGACACCCTGGCTGGCTGTGTGCTGGGCCATCTTCTCTCTGCTGAAGGCCAGGACTGACCGAGCCAGAGGTGACC
CAGACACCTTCCCACCAGGTGACACAGATGGGCCAGGAAGTGATCCTGAGATGCCAATCAGCAACCAC
CTGTACTTTTATTGGTACCGCCAGATCCTGGGCCAGAAGGTGGAGTTCCTGGTGTCCTTTTATAACAATGAG
ATCAGCGAGAAGTCCGAGATCTTCGACGATCAGTTTTCTGTGGAGCGGCCCGATGGCAGCAATTTCACCCTG
AAGATCAGATCCACAAAGCTGGAGGATTCTGCCATGTATTTTTGCGCAGCTGTCCGTCCGGAACCCAGCTGTCCG
GAGAAGCTGTTCTTTGGAGCCGGAACCAAGCTGGAGGATTCTGCCATGTATTTTTGCGCAGCCACCCCTAAGGTGTC
TCTGTTCGAGCCCAGCAAGGCCGAGATCGCCAATAAGCAGAAGGCCACCCTGGTGTGCCTGGCCAGGGGCTTCTTCCCGATCA
CGTGGAGCTGGTCCTGGTGAACGGCAAGGAGGTGCACTCTGGCGTGTCCACCGACCCTCAGCCCTATAAGGAGTCTAATTA
TAGCTACTGTCTGTCTAGCCGGCTGAGAGTGAGCGCCACCTTTTGGCACAACCCCCGGAATCACTTCAGATGCCAGGTGCAGTT
TCACGGCCGTGTCGAGGAGGATAAGTGGCCTGAGGGCCTGAGAATCACCCTGTCCCGCCAATCCTGTATGAGATCCTGCTGGGCAAGGAAG
GGCAGACTGTGGAATCCTCTGCCAGCTACCAGCAGGGCGTGCTGTCCGCCACCATCCTGTATGAGATCCTGCTGGGCAAGGC
CACCCTGTACGCCGTGCTCGTGTCTACACTGGTGGTGATGGCTATGGTGAAGCGGAAGAACAGC

FIGURE 12B

Codon optimized nucleotide sequence encoding alpha chain of TRBV2-01+TRAV12-02 Chimeric TCR, with human variable region in larger font, CDR1, CDR2, CDR3 underlined, and mouse beta constant in italics

ATGATGAAGAGAGCCTGAGAGTGCTGCTGGTCATCCTGTGGTGGTCTCCTGGGTGGTGTCTCAGCAGAAG

GAGGTGGAGCAGAACAGCGGACCACTGTCCGTGCCCAGAGGAGCCATCGCCAGCCTGAATTGCACCTACTCC

GACAGGGGGCAGGCCAGTCCTTCTTTTGGTATCGGCCAGTACTCCCGGCAAGTCTCCTGAGCTGATCATGAGCATC

TATTCCAACGGCGACAAGGAGGATGGCCGGTTCACAGCGCCGGTTCACAGCGCCACCTACCTGTGCGCCGCCTACC

CTGATCAGAGATTCCCAGCCATCTGATAGCGCCACCTACCTGTGCGCCGCCTACCTGTGCGCCGCCTACCGGAGGCTACAAC

AAGCTGATCTTTGGAGCAGGAACAAGACCTGCAGTGCAGTCAACCTAACATCCAGAATCCCGAGCCCGTGTATCAGCT

GAAGGACCCACGGTCTCAGGATAGCAGCACCCTGTCCCTGTTCACAGACTTTGATAGCCAGACTTTGATAGCCAGATCAATGTGCCCAGAAGACAATGGAGTC

CGGCACCTTCATCACAGACACAAGTGCGTGCTGGATATGAAGGCTATGGACTCCAAGTCTAACGGCGCCAGCTAACGGCGCCAGCGCCTGGTCCAATCCA

GACCTCTTTCACATGCCAGGATATCTTTAAGGAGGACCAACGCCACATACCCTTCCTCTGACGTGCCATGTGATGCCATGTGATGCCACCCTGAC

AGAGAAGAGCTTCGAGACGACATGAAGGCTTCGAGACGACATGAAGTTTCAGAACCTGAATTTCAGAACCTGCTGGTCATCGTGCTGGTCATCGTGGAGGATCCTGGAAGGTGGC

CGGCTTTAATCTGCTGATGACACTGGAGCTCCTGATGA

FIGURE 13A

Nucleotide sequence encoding human beta chain of TRBV2-01 + TRAV12-02 human TCR, with human variable region in larger font, CDR1, CDR2, CDR3 underlined, and human beta constant in italics

```
ATGGATACCTGGCTCGTATGCTGGGCAATTTTTTAGTCTCTCTTGAAAGCAGGACTCACAGAACCTGAAGTCACC
CAGACTCCCAGCCATCAGGTCACACAGATGGACAGGAAGTGATCTTGCGCTGTCCCATCTCTAATCAC
TTATACTTCTATTGGTACAGACAAATCTTGGGCCAGAAAGTCCAGTTTCTCGGTTCCTTTTATAATAATGAA
ATCTCAGAGAAGTCTGAAATATTCGATGATGATCAATTCTCAGTTGAAAGGCCTGATGGGATCAAATTTCACTCTG
AAGATCCGGTCCACAAAGCTGGAGGACTCAGCCATGTACTTCTGTGCCAGCAGTAAAGACTACCGGGGAGGT
GAAAAACTGTTTTTTGGCAGTGGAACCCAGCTCTCTTGGAGGACCTGAACAGGTGTTCCCACCCGAGGTGC
CGTGGGAGCTGAGCTGTGGGGTGAATGGGAAGGAGAGGTGCACAGTGGGGTCAGCACCCGCCGGACCA
CCTCAATGACTCCAGATACTGCCTGAGCCAGCCGCGCTCTCGGGGTCTCCGAGCTCCTTCGGGAGGAGCAGCCGGC
TCAAGTCCAGTTCTCACGGGCTCTCCGGAGAATGACGAGTGGACCCAGGATAGGGCCAAACCCGTCACCCAGATCGTCAGCGCCGGA
GGCCTGGGGGTAGAGCAGGGTAGAGCAGACTGTGGCTTTACCTCGGCTGTGCCTTACCAGAGCAGGGGTCCTTATGAGATCCT
GCTAGGGAAGGCCACCCTGTATCCGTGTGCTGGTCAGCGCGCCCTTGTGTTGTTGATGGCCATGGTCAAGAGAAAGGCATTTC
```

FIGURE 13B

Nucleotide sequence encoding human alpha chain of TRBV2-01 + TRAV12-02 human TCR, with human variable region in larger font, CDR1, CDR2, CDR3 underlined, and human beta constant in italics

ATGATGAAATCCTTGAGAGTTTTACTAGTGATGATCCTGTGGCTTCAGTTGAGCTGGGTTTGGAGCCAACAGAAG

GAGGTGGAGCAGAATTCTGGACCCCCTCAGTGTTCCAGAGGGAGCCATTGCCTCCTCTCAACTGCACTTACAGT

GACCGAGGTTCCCAGTCCTTCTTCTGGTACAGACAATATTCTGGGAAAAGCCCTGAGTTGATAATGTCCATA

TACTCCAATGGTGTGACAAAGAAGATGGAAGGTTTACAGCACAGCCAGTCAATAAAGCCAGCCAGTATGTTTCTCTG

CTCATCAGAGACTCCCAGCCCAGTGATTCAGCAGCCACCTACCTCTGTGCCGCCCTGAGCCCTGAGGCCTGGCTACAAT

AAGCTGATTTTTGGGAGCAGGCAGGACCCAGGCTGGCTGTGTACACCCAAATATCCAGAACCTGACCCTGCCCTGTACCAGCT

GAGAGACTCTAAATCCAGTGACAAAGTCTGTCTGCCTATTCACCGGATTTGAGTTCAAACAAATGTGTCACAAAGTAGGATTC

TGATGTGTATATCACAGACAAAAACTGGCTAGACATGAGGTCTAGACTTCAAGAGCAACAGTGCTGTGCCCTGGAGCAACAA

ATCTGACTTGCATGTGCAAACGCCTCAAACAAGCCCTTCAAACAACAGCCATTATTCCAGAAGACAACCTCTTCCCAGCCCAGAAAGTTCTGTGA

TGTCAAGCTGGTGACAGAAAAGTTTGAAAACAGATTTGAAAACCTTAAACTTTCAAAACCTGTCAGTGATTGGGTTCAGTGAATCCTCCT

CCTGAAAGTGGCCCGGGTTTAATCTGCTCAATGACGCTGCCGGCTGTGTGGCTGTGTCCAGCTGATGA

FIGURE 14A

Codon optimized nucleotide sequence encoding beta chain of TRBV2-01 + TRAV12-02 human TCR, with human variable region in larger font, CDR1, CDR2, CDR3 underlined, and human beta constant in italics ATGGACACCTGGCTGGTGTGCTGGGCCATCTTTTCCCTGCTGAAGGCCAGGACTGACCGAGCCAGAGGTGACC
CAGACACCTTCTCACCAGGTGACACAGATGGCCAGGAAGTGATCCTGAGATGCGTGCCAATCAGCAACCAC
CTGTACTTCTATTGGTACCGCCAGATCCTCGGGCCAGAAGGTGGAGTTCCTGCCTTTTACAACAATGAG
ATCTCCGAGAAGTCTGAGATCTTCGACGATCAGTTTAGCGTGGAGCGGCCCGATGGCTCCAACTTTACCCTG
AAGATCAGAAGCACAAAGCTGGAGGATTCCGCCGTGTATTTCTGCGCCATGTACCAAGGACTACAGGGAGGA
GAGAAGCTGTGTCTTTGGCTTCTCGGCACCCCAGCTGAGCGTGCTGGAGGACCTGAATAAGGTGTTCCCCCCTGAGGTGGC
CGTGTTTGAGCCTTCCGAGGCCGAGATCTCTCACACCCAGAAGGCCACCCTGGTGTGCCTGGCAACCGGCTTCTTTCCAGATCA
CGTGGAGCTGAGCTGGTGGGTGAACGGCAAGGAGGTGCACAGCGGCGTGTCCACGGACCCACAGCCCCTGAAGGAGCAGCCCGC
CCTGAATGATAGCAGATATTGCCTGTCCAGCCGCCTGAGAGTGTCCGCCACCTTTTGGCAGAACCCTCGGAATCACTTCAGATG
TCAGGTGCAGTTTTACGGGCCTGAGCGAGGAATGACGAGTGGACCCAGGATAGGGACCAGGGGCTGCTGAGCGCCACCATCCTGTATGAGATCCT
GGCATGGGGAGGGAAGGCCGACTGGTACGCCGGCTTCACATCCGTGTCCTACCCCTGGTGCTGGTGTCCTGTGGTGTCCGGCGGA
GCTGGGCAAGGCCACTGTACGCCGGCTTATGGCTAGGGTGCTGATGGCTATGGCTGAAGCGGAAGGACTTT

FIGURE 14B

Codon optimized nucleotide sequence encoding alpha chain of TRBV2-01 + TRAV12-02 human TCR, with human variable region in larger font. CDR1, CDR2, CDR3 underlined, and human beta constant in italics ATGATGAAGTCCCTGAGAGTGCTGCTGGTCATCCTGTGGCTGCAGCTGTCTTGGGTGTGGAGCCAGCAGAAG
GAGGTGGAGCAGAACTCCGGACCTGTCTGTGCCAGAGGGAGCCATCCCGCCCTCTGAATTGTACCTACAGC
GACAGGGGCTCTCAGAGCTTCTTTTGGTATCGCCAGTACTCTGGCAAGAGCCCTGAGCTGATCATGTCCATC
TATTCTAACGGCGACAAGGAGGATGGCCAGGTTTACAGCCCTGAATAAGGCCAGCCAGTACGTGTCCCTG
CTGATCCGGCGACAGCCAGCCATCCGATTCTGCCACCTATCTGTGCGCCCTATCTGTGCGCGAGGAGGATACAAC
AAGCTGATCTTCGGAGCAGGAACAAGACTGGCAGTGCACCCAGAATCCCAGACCCTGCCGTGTATCAGCT
GAGGGACTCCAGGTCCTCTGATAAGAGCGTGTGCCTGTTCACCGACTTGATTCTCAGAGAACGTGAGCCAGTCCAAGGACAG
CGAGGTGTACATCACGACAAGACAGCAACTGCTGGAATATGGGAGCCATGGAATCTCAACTCTAACGGGGCCGTGGCCTGGAGCAATAA
GTCCGGATTTCGCGCTGCGCCAATGCCTTAACAATTCCATCAACAATTCAACATCCCTGAGGATACCTTCTTTCCATCTCCCGAGAGCTCCTGTGTGA
CGTGAAGCTGGTGGTGGGAGAAGTCTTTGGAGAAGTTCTTTCAGAGACCGGATACAAACCTGAATTTTCAGAGAACCTGAAGCGTGATCGGCGTTCCGGATCCTGTGA
GCTGAAGGTTGGCCGGGCTTCAATCTGCTCGATGACGATGACTGAGACTGAGCTGATGA

FIGURE 15A

Nucleotide sequence encoding beta chain of TRBV27-01+TRAV13-01 Chimeric TCR, with human variable region in larger font, CDR1, CDR2, CDR3 underlined, and mouse beta constant (codon optimized) in italics

ATGGGCCCCCAGCTCCTTGGCTATGTGGTCCTTTGCCTTCTAGGAGCAGGCCCCTGGAAGCCCAAGTGACC

CAGAACCCAAGATACCTCATCACAGATCTGACTGGAAGAAGTTAACAGTGACTTGTTCTCAGAATATGAACCAT

GAGTATATGTCCTGGTATCGACAAGACACCAGGCTGGGCTTAAGGCAGATCTACTATTCAATGAATGTTGAG

GTGACTGATAAGGGAGATGTTCCTGAAGGGGTACAAAGTCTCTGAAAAGAGAGAAGAGAGGAATTTCCCCCTGATC

CTGGAGTCGCGCCCAACCAGACCTCTCTGTACTTCTGTGCCAGCAGCCAGGGGTTAGCAACTAATGAAAAA

CTGTTTTTTGGCAGTGGAACCCAGCTCTCTGTCTTGGAGGACCTGAGAACGTGAGTGACCCCACCTAAGGTGTCCCTGTTC

GAGCCGTCTTCTAAGGCCGAGATCGCCAATAAGCAGAAAGGCACCCTGGTGTGCCTGGCCCGGGGCTTCTTTCCAGATCACGTGGAG

CTGAGCTGGTGGGTGAACGGCAAGGAGGTGCACTCCGGCGTGTCCACCGACCCACAGCCTACAAGGAGCAATTACTCCTAT

TGTCTCGAGCTCCGCCGTGTCCGGGCCACATTTGGCACAACCCAGGAATCACTTCCCGCTGCCAGTTTCACGGGC

CTGAGCGAGGAGGATAAGTGGCCTGAGCGGCTCCCCTAAGGCCGTGCTGAGCGCGTGCTGAGCGGCCAGAC

TGTGGAATCACCAGCGCCTCCTATCAGCAGGGCGTCCTGAGCGCTGCTGAGATCCTGTACCGAGATCCGGGAAGCGGAGAACTCT

TATGCCGTGCGTGGTGTCCACCACTGGTGGTCATGGCTATGGGGTCAAGCGGGAAGAGAACTCT

FIGURE 15B

Nucleotide sequence encoding alpha chain of TRBV27-01+TRAV13-01 Chimeric TCR, with human variable region in larger font, CDR1, CDR2, CDR3 underlined, and mouse beta constant (codon optimized) in italics ATGACATCCATTCGAGCTGTATTTATATTCCTGTGGCTGCAGCTGGACTGGTGAATGGAGAGAATGTGGAG
CAGCATCCTTCAACCCTGAGTGTCCAGGAGGGAGCAGCGCTGTTATCAAGTGTACTTATTCAGACAGTGCC
TCAAACTACTTCCCTTGGTATAAGCAAGAAGAACTTGGAAAAGAGCCTCAGCTTATTATAGACATTCGTTCAAAT
GTGGGGCGAAAAGAAGAAGACCAAGGAATTGCTGTTACATTGAACAAGAGCCAAACATTTCTCCCTGCACATC
ACAGAGACCCAACCTGAAGACTCGGCTGTCTACTTCTGCAGCAAGTAAAGGAAAACACACTCTTGTCTTT
GGAAAGGGCACAAGACTTTCTGTGATTGCAAACATCCAGAACCCAGAGCCCGGCCGTGTATCAGCTGGACCCAAGAT
CCCAGGATTCTACCCTGTGTCCTGTTCACAGACTTTGATTCCAGACTTCCAGATCCAGATTCCATCA
CAGAGCAAGTGCGTGCTGGATATGAAGGCTATGGACTCCAAGTCTAACGGCCCATGCCTGGAGCAATCAGACCTCCTTCACAT
GCCAGGATATCTTTAAGGAGACAAAGGCCACATACCCTTCTAGGAAGTGCATGTAGTGATGCCACCTGACGTGGATCTCG
AGACAGAGACATGAACCTGAATTTCAGAAATTTCGAGAATCTGCTGGTCATGTCGTGGATCCTGCCTGCTGCTGGATTCCTGCGTTAATCTGC
TGATGACACTGCTGCGACTGTGGGAGCTAGCTGAATGA

FIGURE 16A

Codon optimized nucleotide sequence encoding beta chain of TRBV27-01+TRAV13-01 Chimeric TCR, with human variable region larger font, CDR1, CDR2, CDR3 underlined, and mouse beta constant in italics

ATGGGACCACCAGCTGCTGCGGATACGTGGTGGTGCTGCTGCTCGGAGCAGGACCACTGGAGGCACAGGTGACC

CAGAACCCTAGATATCTGATCACCAGAGCCGTGACGAGGCAAGAAGCTGACCGTGACGAGCTAGCCAGAACATGAATCAC

GAGTACATGTCCCTGGTATCGGCAGGATCCCTGGCCTGGGCCTCAGACACAGATCTACTACTAGCATGAATGTGGAG

GTGACCGACAAGGGCGATGTGCCTGAGGGCTACAAGGTGTCCCGGAAGGAAGAGAAACTTCCCACTGATC

CTGGAGAGCCCATCCCCAATCAGACCTCTCTGTATTTTTGGCAAGCAGGGACTGGCAACCAATGAGAAG

CTGTTCTTTGGCTCCGGCACACAGCTGTCTGTTCTGGAGGACCTGAGAAACGTGACCCCCTAAGGTGAGCCTGTTC

GAGCCCTCCAAGGCAGAGATCGCCAATAAGCAGAAGGCCACCCTGGTGTGCCTGGCCAGGGGCTTCTTCCCTGATCACGTGGAG

CTGTCTTGGTGGGTGAACGGCAAGGAGGTGCACAGCGGCGTGTCGACCGACCCACAGGCCTACAAGGAGTCTAATTACAGCTAT

TGTCTGAGCTCCCGGCTGAGAGTGTCCGCCACCATTTTGGCACAACCAAGGAATCACTTCGCGTGCCAGTTTCACGGC

CTGTCTGAGGAGGATAAGTGGCCAGAGGGAAGCCTAAGCCCAGTGACCCGTGCTGAGCGCCACAATCCTGTACGAGATCCCTGCTGGGCTGGGCCAGGGCAGAC

TGTGGAATCACCCTGCTGGCCAGCTATCAGCAGGGCGTGCTGAGCGCCACAATCCTGTACGAGATCCCTGCTGGGCTATGGTGAAGGGCCAGGGCCACCCTG

TATGCCGTGCGTGGTGAGCACACTGGGTGGTCATGGCTATGGTGAAGAGGAAGAACTCC

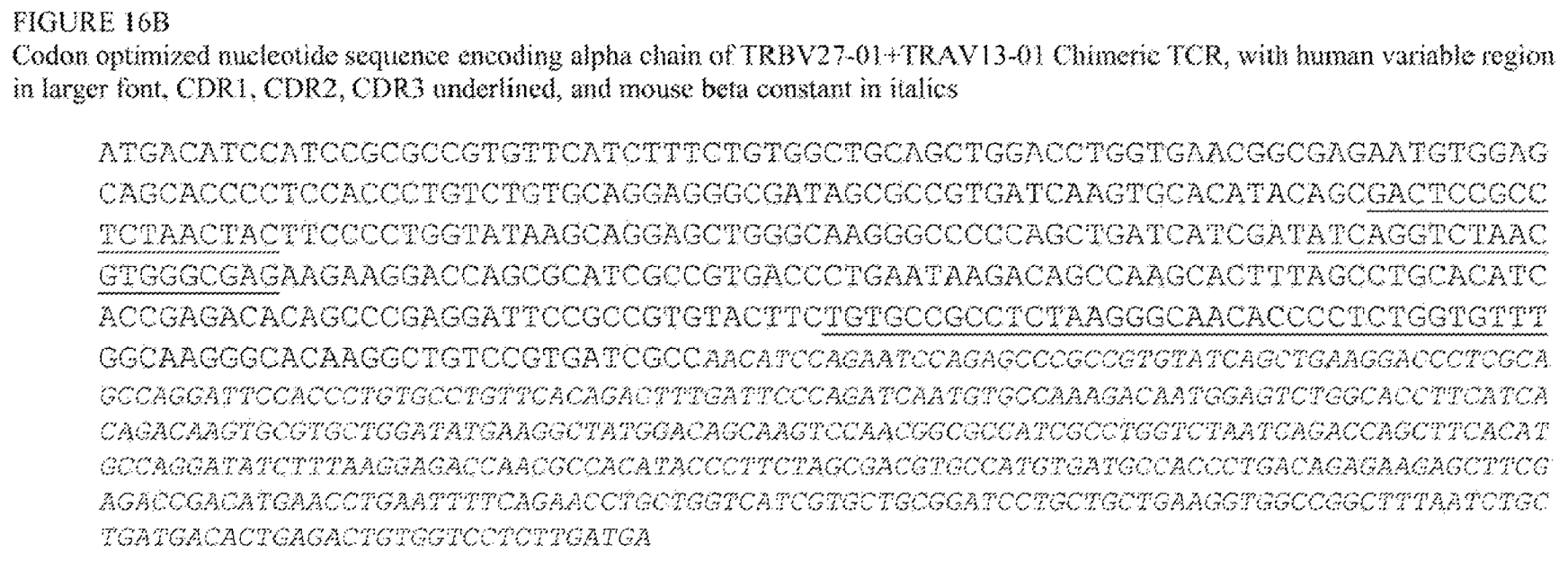

FIGURE 16B
Codon optimized nucleotide sequence encoding alpha chain of TRBV27-01+TRAV13-01 Chimeric TCR, with human variable region in larger font, CDR1, CDR2, CDR3 underlined, and mouse beta constant in italics

FIGURE 17A

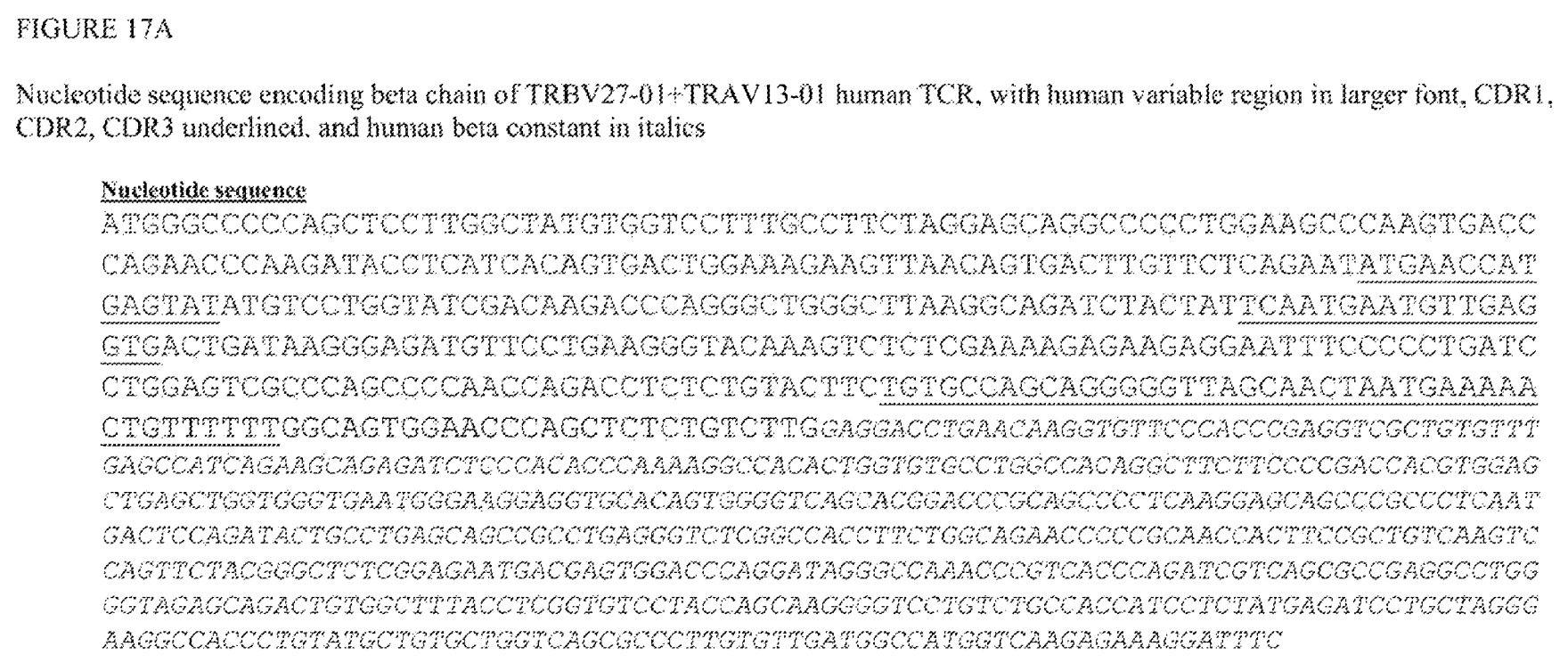

Nucleotide sequence encoding beta chain of TRBV27-01+TRAV13-01 human TCR, with human variable region in larger font, CDR1, CDR2, CDR3 underlined, and human beta constant in italics Nucleotide sequence

ATGGGCCCCCAGCTCCTTGGCTATGTGGCTAGTGGTCCTTTGCCTTTCTAGGAGCAGGCCCCCTGGAAGCCCAAGTGACC

CAGAACCCAAGATACCTCATCACAGTGACTCACTCGGAAAGAAGAAGTTAACAGTGACTTGTTCTCAGAATATGAACCAT

GAGTATATGTCCTGGTATCGACAAGACCCAGGGCTTAAGGCAGATCTACTATTCAATGAATGTTGAG

GTGACTGATAAGGGAGATGTTCCTGAAGGGTACAAAGTCTCTCGAAAAGAGAAGAGGAATTCCCCCTGATC

CTGGAGTCGCCCAACCAGACCTCTCTGCTCTTCTGTGTCACTTGCTGCAGGGGTTAGCAACTAATGAAAAA

CTGTTTTTTGGCAGTGGAACCCAGCTCTCTGTCTTGGAGGACCTGAACAAGGTGTTCCCACCCGAGGTGCCTGTGTTT

*GAGGCCATCAGAGGAAGCAGAGATCTCCCACACCCAAAAGGCCACACTGGTGTGCCTGGCCACAGGCTTCTTCCCCGACCACGTGGAG*

*CTGAGCTGGTGGGTGAATGGGAAGGAGGTGCACAGTGGGGTCAGCAGTGCCCTTCAAGGAGCAGCCGCCCGCCCTCAAT*

*GACTCCAGATACTGCCTGAGCAGCCGCCTGAGGGTCCGGCCACCTTCTGGGAGCACCCGCAGAACCCGCCAACCACTTCGGCTGTCAAGTC*

*CAGTTCTACGGGCTCTCGGGAGAATGAGGAGTGGACCCAGGATAGGGGCCAAACCCGTCACCCAGATCCTGTCTGCCACCATCCTCTATGAGATCCTGCTAGGG*

*GGTAGAGCAGACTGTGGCTTTACCTCGGGTGTCCTACCAGCAAGGGGTCCTGTCTGCCACCATCCTCTATGAGATCCTGCTAGGG*

*GGTAGAGCAGACTGTGGCTTTACCTCGGGTGTCCTACCAGCAAGGGGTCCTGTGTGTTGATGGCCATGGTTGATGGCCATGGTTGATGGCCTGGTCAGCGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGTGTCAGCGTCAGCGTCAGCGGT*

*AAGGCCACCCTGTATGCTGTGCTGGTCAGCGCCCTGGTCCTGATGGCCATGGTCAAGAGAAAGGATTTC*

FIGURE 17B

Nucleotide sequence encoding alpha chain of TRBV27-01+TRAV13-01 human TCR, with human variable region in larger font, CDR1, CDR2, CDR3 underlined, and human alpha constant in italics

ATGACATCCATTCGAGCTGTATTTATATTCCTGTGGCTGCAGCTGGACTGGTGAATGGAGAGAGAATGTGGAG

CAGCATCCTTCAACCCTGAGTGTCCAGGAGGGAGGACAGCGCCTGTTATCAAGTGTACTTATTCAGACAGTGCC

TCAAACTACTTCCCTTGGTATAAGCAAGGACCTCAGCTTATTATAGACATTCGTTCAAAT

GTGGGCGAAAAGAAAGAAGACCAACGAATTGCTGTTACATTGCTGTGTTACTTCTCCCTGCACATC

ACAGAGACCCAACCTGAAGACTCGGCTGTCTACTTCTGTGCCAGCAAGTAAAGGAAAACACCCTCTTGTCTTT

GGAAAGGGCACAAGACTTTCTGTGATTGCAAATATCCAGAACCTGACCTGCCGGTACCTGCAGCTGAGAGACTCTAAAT

CCAGTGACAAGTCTGTCTGCCTATTCACCGATTTTGATTCTCAAACAAATGTGTCACAAAGTAAGGATTCTGATGTGTATATCA

CAGACAAAACTGTGCTAGACATGAGGTCTATGAGGTCTTCAAGAGCTTCAAGAGCAACAATCTGACTTTGCAT

GTGCAAACGCCTCAACAACAGACCATTATTCCAGAAGACACCTTCTTCCCAGCCCAGAAGTTCCTGTGATGTCAAGCTGGTCG

AGAAAGCTTTGAAACAGATACGAACCTAAACTTTCAAAACTTGTCAGTGATTGGTTCCGAATCCTCCTGGAAGTGGGCCG

GGTTTAATCTGCTTCATGACGCTGCGGCTGTGGTGGTCCAGCTGATGA

FIGURE 18A

Codon-optimized nucleotide sequence encoding beta chain of TRBV27-01+TRAV13-01 human TCR, with human variable region in larger font, CDR1, CDR2, CDR3 underlined, and human beta constant in italics ATGGGACCACCAGCTGCTGGGATACGTGGTGGTGCTGCTGTGCCTGCTGGGAGCCAGGACCACTGGGAGGCCACAGGTGACC
CAGAACCCTCGGTATCTGATCTGACCGTGACAGGCAGAAGCTGACCGTTCCCAGAACATGAATCAC
GAGTACATGTCTTGGTATAGGCAGGACCCTGGACTGGGACTGAGACTGATCTATTCCATGAATGTGGAG
GTGACCGACAAGGGCGATGTGCCTGAGGGCTACAAGGTGTCTCGGAAGGAGAAGAAACTTTCCACTGATC
CTGGAGTCTCCAAGCCCCAATCAGACATCCCTGTATTTCTGCGCCCTCTAGAGGCCTGGCCAACGAGAAG
CTGTTCTTTGGCAGCGGCACAAGCTGTCCGTCCGTGCTGCTGGAGGACCTGAATAAGGTGTTCCCCCTGAGGTGGCCGTGTTT
GAGCCATCTGAGGCCGAGATCAGCCACACCCAGAAGGCCACCCTGGTGTGCCTGGCAACGGCTTCTTCCCCGATCACGTGGAG
CTGTCCTGGTGGGTGAACGGCAAGGAGGTGCACAGCGGCGTGTCCACCGACCCTCAGCCCCTCAAGGAGCAGCCTGCCCTGAAT
GATTCCAGGTACTGCCTGAGCTCCCGGCTGAGAGTGTCTGCCACCTTTTGGCAGAACCCAAGGAATCACTTCCGGTGTCAGGTG
CAGTTTTATGGCCTGAGCGAGAACGACGAGTGGACCCAGGATCGGGCCAAGCCCGTGACGCAGATCGTGTCCGCGGAGGCATGG
CGAAGAGCAGACTGGCGGCTTCAGCAGCGAGTCCTATCAGCAGGGCGTGCTGTCTGCCACCATCCTGTACGAGATCCTGCTGGGC
AAGGCCACACTGTATGCCGTGCTGGTGAGCGCCCTGGTGCTGATGGCTATGGTGAAGAGGAAGGACTTT FIGURE 18B
Codon-optimized Nucleotide sequence encoding alpha chain of TRBV27-01+TRAV13-01 human TCR, with human variable region in larger font, CDR1, CDR2, CDR3 underlined, and human alpha constant in italics

ATGACAAGCATCCGGCGCCGTGTTCATCTTTCTGTGGCTGCCAGCTGGATCTGGTGAACGGGCGAGAAGTGGAG

CAGCACCCTTCTACCCTGAGCGTGCAGGAGGGCGATAGCGCCGTGATCAAGTTACATACTCTGACAGCGCC

TCCAACTACTTTCCCTGGTATAAGCAGGAGCCCCCCAGGGCCAAGGGCAAGCTGGGCAACTGAGCTGATCATCGATATCAGGTCCAAC

GTGGGCGGAGAAGGACCAGCGCATCGCCGTGACCCGTGAATAAGACAGCCAACTTCAGCCTGCACATC

ACGGAGACACAGCCCGAGGACTCTGCCGTGTACTTTTGGCCGCCAGCAAGGCAATACCCCTCTGTGTTC

GGCAAGGGCACACGGCCTGTCCGTGATCCGCCAACATCCAGAATCCCGCCGTGTATCAGCTGAGAGACAGCAAGT

CTAGCCGATAAGAGCGTGTGCCCGTTCACCGACTTTGATAGCCAGACAAACGTGTCTCAGAGCAAGGACTGTACATCA

CGGACAABACAGTGCTGGATATGCGAGCAATGGACTTAAGTCCAACTCTGCCGTGGCCGTGGCCTGGACTTCGGCCT

GCGCCAATGCCTTTAACAATTCTATCATCCCCGAGGATACCTTCTTCCCTAGCCAGAGTCCCTTCGTTGTGAAGCTGGTGG

AGAAGAGCTTCGAGACACCGATACAAACCTGAATTTTCAGAAACCTGTCCGTGATCGGCCTGATGTGTCTGACCGATGA

GCTTCAATCTGCTGATGACCCTGCGCCCTGTGGAGCTCCTGATGA

SEQUENCE LISTING

```
<160> NUMBER OF SEQ ID NOS: 108

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Asn His Leu Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Tyr Asn Asn Glu Ile
1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ala Ser Ser Lys Asp Tyr Arg Gly Gly Glu Lys Leu Phe Phe
1               5                   10                  15

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Thr Trp Leu Val Cys Trp Ala Ile Phe Ser Leu Leu Lys Ala
```

-continued

```
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile
        35                  40                  45

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Tyr Trp Tyr Arg Gln Ile Leu Gly Gln Lys Val Glu Phe Leu Val
1               5                   10                  15

Ser

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Glu Lys Ser Glu Ile Phe Asp Asp Gln Phe Ser Val Glu Arg Pro
1               5                   10                  15

Asp Gly Ser Asn Phe Thr Leu Lys Ile Arg Ser Thr Lys Leu Glu Asp
            20                  25                  30

Ser Ala Met Tyr Phe
        35

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Gly Thr Gln Leu Ser Val Leu
1               5

<210> SEQ ID NO 8
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
```

-continued

```
        50              55              60

Glu Ser Asn Tyr Ser Tyr Cys Leu Ser Ser Arg Leu Arg Val Ser Ala
65              70              75              80

Thr Phe Trp His Asn Pro Arg Asn His Phe Arg Cys Gln Val Gln Phe
            85              90              95

His Gly Leu Ser Glu Glu Asp Lys Trp Pro Glu Gly Ser Pro Lys Pro
                100             105             110

Val Thr Gln Asn Ile Ser Ala Glu Ala Trp Gly Arg Ala Asp Cys Gly
            115             120             125

Ile Thr Ser Ala Ser Tyr Gln Gln Gly Val Leu Ser Ala Thr Ile Leu
            130             135             140

Tyr Glu Ile Leu Leu Gly Lys Ala Thr Leu Tyr Ala Val Leu Val Ser
145             150             155             160

Thr Leu Val Val Met Ala Met Val Lys Arg Lys Asn Ser
                165             170
```

```
<210> SEQ ID NO 9
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Thr Trp Leu Val Cys Trp Ala Ile Phe Ser Leu Leu Lys Ala
1               5               10              15

Gly Leu Thr Glu Pro Glu Val Thr Gln Thr Pro Ser His Gln Val Thr
                20              25              30

Gln Met Gly Gln Glu Val Ile Leu Arg Cys Val Pro Ile Ser Asn His
            35              40              45

Leu Tyr Phe Tyr Trp Tyr Arg Gln Ile Leu Gly Gln Lys Val Glu Phe
            50              55              60

Leu Val Ser Phe Tyr Asn Asn Glu Ile Ser Glu Lys Ser Glu Ile Phe
65              70              75              80

Asp Asp Gln Phe Ser Val Glu Arg Pro Asp Gly Ser Asn Phe Thr Leu
                85              90              95

Lys Ile Arg Ser Thr Lys Leu Glu Asp Ser Ala Met Tyr Phe Cys Ala
                100             105             110

Ser Ser Lys Asp Tyr Arg Gly Gly Glu Lys Leu Phe Phe Gly Ser Gly
            115             120             125

Thr Gln Leu Ser Val Leu Glu Asp Leu Arg Asn Val Thr Pro Pro Lys
            130             135             140

Val Ser Leu Phe Glu Pro Ser Lys Ala Glu Ile Ala Asn Lys Gln Lys
145             150             155             160

Ala Thr Leu Val Cys Leu Ala Arg Gly Phe Phe Pro Asp His Val Glu
                165             170             175

Leu Ser Trp Trp Val Asn Gly Lys Glu Val His Ser Gly Val Cys Thr
                180             185             190

Asp Pro Gln Ala Tyr Lys Glu Ser Asn Tyr Ser Tyr Cys Leu Ser Ser
            195             200             205

Arg Leu Arg Val Ser Ala Thr Phe Trp His Asn Pro Arg Asn His Phe
    210             215             220

Arg Cys Gln Val Gln Phe His Gly Leu Ser Glu Glu Asp Lys Trp Pro
225             230             235             240
```

-continued

```
Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Arg Gly Ser Gln Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Ser Asn Gly Asp
1               5

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ala Ala Leu Arg Pro Gly Gly Tyr Asn Lys Leu Ile Phe
1               5                   10

<210> SEQ ID NO 13
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
                20                  25                  30

Leu Ser Val Pro Glu Gly Ala Ile Ala Ser Leu Asn Cys Thr Tyr Ser
        35                  40                  45

<210> SEQ ID NO 14
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Phe Trp Tyr Arg Gln Tyr Ser Gly Lys Ser Pro Glu Leu Ile Met
1               5                   10                  15

Ser

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Glu Asp Gly Arg Phe Thr Ala Gln Leu Asn Lys Ala Ser Gln Tyr
1               5                   10                  15

Val Ser Leu Leu Ile Arg Asp Ser Gln Pro Ser Asp Ser Ala Thr Tyr
            20                  25                  30

Leu

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Gly Thr Arg Leu Ala Val His Pro
1               5                   10

<210> SEQ ID NO 17
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110
```

Val Ile Val Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 18
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Leu Arg Pro Gly Gly Tyr Asn Lys Leu Ile Phe Gly Ala Gly Thr
        115                 120                 125

Arg Leu Ala Val His Pro Asn Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Cys Val Leu Asp Met Lys Ala Met Asp Ser Lys
            180                 185                 190

Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Leu Val Ile Val Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 19
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

-continued

```
Glu Asp Leu Asn Lys Val Phe Pro Pro Glu Val Ala Val Phe Glu Pro
1               5               10              15

Ser Glu Ala Glu Ile Ser His Thr Gln Lys Ala Thr Leu Val Cys Leu
            20              25              30

Ala Thr Gly Phe Phe Pro Asp His Val Glu Leu Ser Trp Trp Val Asn
            35              40              45

Gly Lys Glu Val His Ser Gly Val Ser Thr Asp Pro Gln Pro Leu Lys
        50              55              60

Glu Gln Pro Ala Leu Asn Asp Ser Arg Tyr Cys Leu Ser Ser Arg Leu
65              70              75              80

Arg Val Ser Ala Thr Phe Trp Gln Asn Pro Arg Asn His Phe Arg Cys
                85              90              95

Gln Val Gln Phe Tyr Gly Leu Ser Glu Asn Asp Glu Trp Thr Gln Asp
            100             105             110

Arg Ala Lys Pro Val Thr Gln Ile Val Ser Ala Glu Ala Trp Gly Arg
            115             120             125

Ala Asp Cys Gly Phe Thr Ser Val Ser Tyr Gln Gln Gly Val Leu Ser
            130             135             140

Ala Thr Ile Leu Tyr Glu Ile Leu Leu Gly Lys Ala Thr Leu Tyr Ala
145             150             155             160

Val Leu Val Ser Ala Leu Val Leu Met Ala Met Val Lys Arg Lys Asp
                165             170             175

Phe
```

```
<210> SEQ ID NO 20
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Thr Trp Leu Val Cys Trp Ala Ile Phe Ser Leu Leu Lys Ala
1               5               10              15

Gly Leu Thr Glu Pro Glu Val Thr Gln Thr Pro Ser His Gln Val Thr
            20              25              30

Gln Met Gly Gln Glu Val Ile Leu Arg Cys Val Pro Ile Ser Asn His
            35              40              45

Leu Tyr Phe Tyr Trp Tyr Arg Gln Ile Leu Gly Gln Lys Val Glu Phe
        50              55              60

Leu Val Ser Phe Tyr Asn Asn Glu Ile Ser Glu Lys Ser Glu Ile Phe
65              70              75              80

Asp Asp Gln Phe Ser Val Glu Arg Pro Asp Gly Ser Asn Phe Thr Leu
                85              90              95

Lys Ile Arg Ser Thr Lys Leu Glu Asp Ser Ala Met Tyr Phe Cys Ala
            100             105             110

Ser Ser Lys Asp Tyr Arg Gly Gly Glu Lys Leu Phe Phe Gly Ser Gly
            115             120             125

Thr Gln Leu Ser Val Leu Glu Asp Leu Asn Lys Val Phe Pro Pro Glu
            130             135             140

Val Ala Val Phe Glu Pro Ser Glu Ala Glu Ile Ser His Thr Gln Lys
145             150             155             160

Ala Thr Leu Val Cys Leu Ala Thr Gly Phe Phe Pro Asp His Val Glu
                165             170             175
```

-continued

```
Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
            210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe
305                 310
```

```
<210> SEQ ID NO 21
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Asn Ile Gln Asn Pro Asp Pro Ala Val Tyr Gln Leu Arg Asp Ser Lys
1                   5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
            50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                    85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140
```

```
<210> SEQ ID NO 22
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

```
Met Met Lys Ser Leu Arg Val Leu Leu Val Ile Leu Trp Leu Gln Leu
1                   5                   10                  15
```

-continued

```
Ser Trp Val Trp Ser Gln Gln Lys Glu Val Glu Gln Asn Ser Gly Pro
        20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
        50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Leu Arg Pro Gly Gly Tyr Asn Lys Leu Ile Phe Gly Ala Gly Thr
            115                 120                 125

Arg Leu Ala Val His Pro Asn Ile Gln Asn Pro Asp Pro Ala Val Tyr
        130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
            165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
        210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
            245                 250                 255

Leu Leu Leu Lys Val Ala Gly Phe Asn Leu Leu Met Thr Leu Arg Leu
        260                 265                 270

Trp Ser Ser
        275
```

```
<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Asn His Glu Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Met Asn Val Glu Val
1               5
```

-continued

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Ala Ser Arg Gly Leu Ala Thr Asn Glu Lys Leu Phe Phe
1               5                   10

<210> SEQ ID NO 26
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn
        35                  40                  45

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Ser Trp Tyr Arg Gln Asp Pro Gly Leu Gly Leu Arg Gln Ile Tyr
1               5                   10                  15

Tyr

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr Asp Lys Gly Asp Val Pro Glu Gly Tyr Lys Val Ser Arg Lys Glu
1               5                   10                  15

Lys Arg Asn Phe Pro Leu Ile Leu Glu Ser Pro Ser Pro Asn Gln Thr
            20                  25                  30

Ser Leu Tyr Phe
        35

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 29

Gly Ser Gly Thr Gln Leu Ser Val Leu
1               5

<210> SEQ ID NO 30
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Cys Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 31
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
```

-continued

```
            100             105             110
Arg Gly Leu Ala Thr Asn Glu Lys Leu Phe Phe Gly Ser Gly Thr Gln
        115             120             125

Leu Ser Val Leu Glu Asp Leu Arg Asn Val Thr Pro Pro Lys Val Ser
    130             135             140

Leu Phe Glu Pro Ser Lys Ala Glu Ile Ala Asn Lys Gln Lys Ala Thr
145             150             155             160

Leu Val Cys Leu Ala Arg Gly Phe Phe Pro Asp His Val Glu Leu Ser
                165             170             175

Trp Trp Val Asn Gly Lys Glu Val His Ser Gly Val Cys Thr Asp Pro
                180             185             190

Gln Ala Tyr Lys Glu Ser Asn Tyr Ser Tyr Cys Leu Ser Ser Arg Leu
            195             200             205

Arg Val Ser Ala Thr Phe Trp His Asn Pro Arg Asn His Phe Arg Cys
        210             215             220

Gln Val Gln Phe His Gly Leu Ser Glu Glu Asp Lys Trp Pro Glu Gly
225             230             235             240

Ser Pro Lys Pro Val Thr Gln Asn Ile Ser Ala Glu Ala Trp Gly Arg
                245             250             255

Ala Asp Cys Gly Ile Thr Ser Ala Ser Tyr Gln Gln Gly Val Leu Ser
                260             265             270

Ala Thr Ile Leu Tyr Glu Ile Leu Leu Gly Lys Ala Thr Leu Tyr Ala
            275             280             285

Val Leu Val Ser Thr Leu Val Val Met Ala Met Val Lys Arg Lys Asn
        290             295             300

Ser
305

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ser Ala Ser Asn Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Arg Ser Asn Val Gly Glu
1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

```
Cys Ala Ala Ser Lys Gly Asn Thr Pro Leu Val Phe
1               5                   10
```

```
<210> SEQ ID NO 35
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser
        35                  40                  45
```

```
<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Pro Trp Tyr Lys Gln Glu Leu Gly Lys Gly Pro Gln Leu Ile Ile
1               5                   10                  15

Asp
```

```
<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Lys Lys Asp Gln Arg Ile Ala Val Thr Leu Asn Lys Thr Ala Lys His
1               5                   10                  15

Phe Ser Leu His Ile Thr Glu Thr Gln Pro Glu Asp Ser Ala Val Tyr
                20                  25                  30

Phe
```

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Lys Gly Thr Arg Leu Ser Val Ile Ala
1               5                   10
```

```
<210> SEQ ID NO 39
<211> LENGTH: 137
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 39

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Cys
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
        130                 135

<210> SEQ ID NO 40
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Lys Gly Asn Thr Pro Leu Val Phe Gly Lys Gly Thr Arg Leu Ser Val
        115                 120                 125

Ile Ala Asn Ile Gln Asn Pro Glu Pro Ala Val Tyr Gln Leu Lys Asp
        130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
            180                 185                 190

```
Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
                260                 265

<210> SEQ ID NO 41
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 42
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
```

-continued

```
                35                      40                      45

Glu Tyr Met Ser Trp Tyr Arg Gln Asp Pro Gly Leu Gly Leu Arg Gln
    50                      55                      60

Ile Tyr Tyr Ser Met Asn Val Glu Val Thr Asp Lys Gly Asp Val Pro
65                      70                      75                      80

Glu Gly Tyr Lys Val Ser Arg Lys Glu Lys Arg Asn Phe Pro Leu Ile
                85                      90                      95

Leu Glu Ser Pro Ser Pro Asn Gln Thr Ser Leu Tyr Phe Cys Ala Ser
                100                     105                     110

Arg Gly Leu Ala Thr Asn Glu Lys Leu Phe Phe Gly Ser Gly Thr Gln
                115                     120                     125

Leu Ser Val Leu Glu Asp Leu Asn Lys Val Phe Pro Pro Glu Val Ala
    130                     135                     140

Val Phe Glu Pro Ser Glu Ala Glu Ile Ser His Thr Gln Lys Ala Thr
145                     150                     155                     160

Leu Val Cys Leu Ala Thr Gly Phe Phe Pro Asp His Val Glu Leu Ser
                165                     170                     175

Trp Trp Val Asn Gly Lys Glu Val His Ser Gly Val Ser Thr Asp Pro
                180                     185                     190

Gln Pro Leu Lys Glu Gln Pro Ala Leu Asn Asp Ser Arg Tyr Cys Leu
                195                     200                     205

Ser Ser Arg Leu Arg Val Ser Ala Thr Phe Trp Gln Asn Pro Arg Asn
    210                     215                     220

His Phe Arg Cys Gln Val Gln Phe Tyr Gly Leu Ser Glu Asn Asp Glu
225                     230                     235                     240

Trp Thr Gln Asp Arg Ala Lys Pro Val Thr Gln Ile Val Ser Ala Glu
                245                     250                     255

Ala Trp Gly Arg Ala Asp Cys Gly Phe Thr Ser Val Ser Tyr Gln Gln
                260                     265                     270

Gly Val Leu Ser Ala Thr Ile Leu Tyr Glu Ile Leu Leu Gly Lys Ala
                275                     280                     285

Thr Leu Tyr Ala Val Leu Val Ser Ala Leu Val Leu Met Ala Met Val
    290                     295                     300

Lys Arg Lys Asp Phe
305
```

<210> SEQ ID NO 43
<211> LENGTH: 141
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 43

```
Asn Ile Gln Asn Pro Asp Pro Ala Val Tyr Gln Leu Arg Asp Ser Lys
1               5                       10                      15

Ser Ser Asp Lys Ser Val Cys Leu Phe Thr Asp Phe Asp Ser Gln Thr
                20                      25                      30

Asn Val Ser Gln Ser Lys Asp Ser Asp Val Tyr Ile Thr Asp Lys Thr
                35                      40                      45

Val Leu Asp Met Arg Ser Met Asp Phe Lys Ser Asn Ser Ala Val Ala
    50                      55                      60

Trp Ser Asn Lys Ser Asp Phe Ala Cys Ala Asn Ala Phe Asn Asn Ser
65                      70                      75                      80
```

-continued

```
Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 44
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
            85                  90                  95

Thr Glu Thr Gln Pro Glu Asp Ser Ala Val Tyr Phe Cys Ala Ala Ser
            100                 105                 110

Lys Gly Asn Thr Pro Leu Val Phe Gly Lys Gly Thr Arg Leu Ser Val
        115                 120                 125

Ile Ala Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
            165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser
            260                 265                 270

<210> SEQ ID NO 45
<211> LENGTH: 134
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 45

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
                20                  25                  30

Leu Ser Val Pro Glu Gly Ala Ile Ala Ser Leu Asn Cys Thr Tyr Ser
            35                  40                  45

Asp Arg Gly Ser Gln Ser Phe Phe Trp Tyr Arg Gln Tyr Ser Gly Lys
        50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Leu Arg Pro Gly Gly Tyr Asn Lys Leu Ile Phe Gly Ala Gly Thr
            115                 120                 125

Arg Leu Ala Val His Pro
    130

<210> SEQ ID NO 46
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Lys Gly Asn Thr Pro Leu Val Phe Gly Lys Gly Thr Arg Leu Ser Val
            115                 120                 125

Ile Ala
    130

<210> SEQ ID NO 47
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
        50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Lys Asp Tyr Arg Gly Gly Glu Lys Leu Phe Phe Gly Ser Gly
            115                 120                 125

Thr Gln Leu Ser Val Leu
        130
```

<210> SEQ ID NO 48
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Arg Gly Leu Ala Thr Asn Glu Lys Leu Phe Phe Gly Ser Gly Thr Gln
            115                 120                 125

Leu Ser Val Leu
        130
```

<210> SEQ ID NO 49
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

-continued

```
atggatacct ggctcgtatg ctgggcaatt tttagtctct tgaaagcagg actcacagaa          60
cctgaagtca cccagactcc cagccatcag gtcacacaga tgggacagga agtgatcttg         120
cgctgtgtcc ccatctctaa tcacttatac ttctattggt acagacaaat cttggggcag         180
aaagtcgagt ttctggtttc cttttataat aatgaaatct cagagaagtc tgaaatattc         240
gatgatcaat tctcagttga aaggcctgat ggatcaaatt tcactctgaa gatccggtcc         300
acaaagctgg aggactcagc catgtacttc tgtgccagca gtaaagacta ccggggaggt         360
gaaaaactgt tttttggcag tggaacccag ctctctgtct tggaggacct gagaaacgtg         420
acacccccta aggtgagcct gttcgagccc tccaaggccg agatcgccaa taagcagaag         480
gccaccctgg tgtgcctggc aaggggcttc tttcctgatc acgtggagct gtcttggtgg         540
gtgaacggca aggaggtgca cagcggcgtg tgcaccgacc cacaggccta taaggagagc         600
aattattcct actgtctgtc tagccggctg agagtgagcg ccacattttg cacaaccct          660 cggaatcact tcagatgcca ggtgcagttt cacggcctgt ctgaggagga taagtggcca         720
gagggcagcc caaagccagt gacccagaac atctccgccg aggcatgggg aagagcagac         780
tgtggcatca ccagcgcctc ctaccagcag ggcgtgctgt ccgccacaat cctgtatgag         840
atcctgctgg gcaaggccac cctgtacgcc gtgctggtga gcacactggt ggtcatggct         900
atggtgaaga ggaagaactc agggcaaag cggagcggaa gcggagccac aaatttctct          960
ctgctgaagc aggcaggcga tgtggaggag aaccctggac caatgatgaa tccttgaga         1020 gtttttactag tgatcctgtg gcttcagttg agctgggttt ggagccaaca gaaggaggtg        1080
gagcagaatt ctggaccct cagtgttcca gagggagcca ttgcctctct caactgcact          1140
tacagtgacc gaggttccca gtccttcttc tggtacagac aatattctgg gaaaagccct         1200
gagttgataa tgtccatata ctccaatggt gacaaagaag atggaaggtt tacagcacag         1260
ctcaataaag ccagccagta tgtttctctg ctcatcagag actcccagcc cagtgattca        1320
gccacctacc tctgtgccgc cctgaggcct ggtggctaca ataagctgat ttttggagca         1380
gggaccaggc tggctgtaca cccaaacatc agaatccag agcccgccgt gtatcagctg          1440
aaggacccaa gatcccagga ttctaccctg tgcctgttca cagactttga ttctcagatc         1500
aatgtgccca gacaatgga gagcggcacc ttcatcacag acaagtgcgt gctggatatg          1560
aaggctatgg actccaagtc taacggcgcc atcgcctgga caatcagac ctccttcaca          1620 tgccaggata tctttaagga acaaacgcc acataccctt ctagcgacgt gccatgtgat          1680
gccaccctga cagagaagag cttcgagaca gacatgaacc tgaattttca gaatctgctg         1740
gtcatcgtgc tgcggatcct gctgctgaag gtggctgggt ttaatctgct gatgacactg         1800
cgactgtgga gtagctgatg a                                                   1821
```

<210> SEQ ID NO 50
<211> LENGTH: 605
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30
```

```
Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
        50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Lys Asp Tyr Arg Gly Gly Glu Lys Leu Phe Phe Gly Ser Gly
            115                 120                 125

Thr Gln Leu Ser Val Leu Glu Asp Leu Arg Asn Val Thr Pro Pro Lys
        130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
        210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
                260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
        290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Met
            325                 330                 335

Lys Ser Leu Arg Val Leu Leu Val Ile Leu Trp Leu Gln Leu Ser Trp
            340                 345                 350

Val Trp Ser Gln Gln Lys Glu Val Glu Gln Asn Ser Gly Pro Leu Ser
        355                 360                 365

Val Pro Glu Gly Ala Ile Ala Ser Leu Asn Cys Thr Tyr Ser Asp Arg
        370                 375                 380

Gly Ser Gln Ser Phe Phe Trp Tyr Arg Gln Tyr Ser Gly Lys Ser Pro
385                 390                 395                 400

Glu Leu Ile Met Ser Ile Tyr Ser Asn Gly Asp Lys Glu Asp Gly Arg
                405                 410                 415

Phe Thr Ala Gln Leu Asn Lys Ala Ser Gln Tyr Val Ser Leu Leu Ile
            420                 425                 430

Arg Asp Ser Gln Pro Ser Asp Ser Ala Thr Tyr Leu Cys Ala Ala Leu
            435                 440                 445

Arg Pro Gly Gly Tyr Asn Lys Leu Ile Phe Gly Ala Gly Thr Arg Leu
```

-continued

```
        450              455              460
Ala Val His Pro Asn Ile Gln Asn Pro Glu Pro Ala Val Tyr Gln Leu
465              470              475              480

Lys Asp Pro Arg Ser Gln Asp Ser Thr Leu Cys Leu Phe Thr Asp Phe
            485              490              495

Asp Ser Gln Ile Asn Val Pro Lys Thr Met Glu Ser Gly Thr Phe Ile
            500              505              510

Thr Asp Lys Cys Val Leu Asp Met Lys Ala Met Asp Ser Lys Ser Asn
        515              520              525

Gly Ala Ile Ala Trp Ser Asn Gln Thr Ser Phe Thr Cys Gln Asp Ile
        530              535              540

Phe Lys Glu Thr Asn Ala Thr Tyr Pro Ser Ser Asp Val Pro Cys Asp
545              550              555              560

Ala Thr Leu Thr Glu Lys Ser Phe Glu Thr Asp Met Asn Leu Asn Phe
            565              570              575

Gln Asn Leu Leu Val Ile Val Leu Arg Ile Leu Leu Leu Lys Val Ala
            580              585              590

Gly Phe Asn Leu Leu Met Thr Leu Arg Leu Trp Ser Ser
            595              600              605
```

<210> SEQ ID NO 51
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
atggacacct ggctggtgtg ctgggccatc ttctctctgc tgaaggcagg actgaccgag     60
ccagaggtga cccagacacc ttcccaccag gtgacacaga tgggccagga agtgatcctg    120
agatgcgtgc caatcagcaa ccacctgtac ttttattggt accgccagat cctgggccag    180
aaggtggagt tcctggtgtc cttttataac aatgagatca gcgagaagtc cgagatcttc    240
gacgatcagt tttctgtgga gcggcccgat ggcagcaatt tcaccctgaa gatcagatcc    300
acaaagctgg aggattctgc catgtatttt tgcgcaagct ccaaggacta caggggagga    360
gagaagctgt tctttggaag cggaacccag ctgtccgtgc tggaggacct cgcaacgtg     420 acaccccta aggtgtctct gttcgagcca agcaaggccg agatcgccaa taagcagaag     480
gccaccctgg tgtgcctggc aaggggcttc tttcccgatc acgtggagct gtcctggtgg    540
gtgaacggca aggaggtgca ctctggcgtg tgcaccgacc ctcaggccta taaggagtct    600
aattatagct actgtctgtc tagccggctg agagtgagcg ccacattttg cacaacccc     660 cggaatcact tcagatgcca ggtgcagttt cacggcctgt ccgaggagga taagtggcct    720
gagggctctc caaagcccgt gacccagaac atcagcgccg aggcatgggg aagggcagac    780
tgtggaatca cctctgccag ctaccagcag ggcgtgctgt ccgccacaat cctgtatgag    840
atcctgctgg gcaaggccac cctgtacgcc gtgctggtgt ctacactggt ggtcatggct    900
atggtgaagc ggaagaacag cagggcaaag cggagcggat ctggagccac aaatttctcc    960
ctgctgaagc aggccggcga tgtggaggag aatcctggcc aatgatgaa gagcctgaga   1020 gtgctgctgg tcatcctgtg gctgcagctg tcctgggtgt ggtctcagca gaaggaggtg   1080
gagcagaaca cgcgaccact gtccgtgcca gaggagccca tcgccagcct gaattgcacc   1140
tactccgaca ggggcagcca gtccttcttt tggtatcgcc agtactccgg caagtctcct   1200
```

```
gagctgatca tgagcatcta ttccaacggc gacaaggagg atggccggtt cacagcccag      1260
ctgaataagg cctctcagta cgtgagcctg ctgatcagag attcccagcc atctgatagc      1320
gccacctacc tgtgcgccgc cctgaggcca ggaggctaca acaagctgat ctttggagca      1380
ggaacaagac tggcagtgca ccctaacatc cagaatcccg agcctgccgt gtatcagctg      1440
aaggacccac ggtctcagga tagcaccctg tgcctgttca cagactttga tagccagatc      1500
aatgtgccca agacaatgga gtccggcacc ttcatcacag acaagtgcgt gctggatatg      1560
aaggctatgg actccaagtc taacggcgcc atcgcctggt ccaatcagac ctctttcaca      1620
tgccaggata tctttaagga gaccaacgcc acataccctt cctctgacgt gccatgtgat      1680
gccaccctga cagagaagag cttcgagacc gacatgaacc tgaattttca gaacctgctg      1740
gtcatcgtgc tgaggatcct gctgctgaag gtggccggct ttaatctgct gatgacactg      1800
cgcctgtgga gctcctgatg a                                                1821
```

```
<210> SEQ ID NO 52
<211> LENGTH: 1845
<212> TYPE: DNA
<213> ORGANISM: Homo sapiens

<400> SEQUENCE: 52
atggatacct ggctcgtatg ctgggcaatt tttagtctct tgaaagcagg actcacagaa        60
cctgaagtca cccagactcc cagccatcag gtcacacaga tgggacagga agtgatcttg       120
cgctgtgtcc ccatctctaa tcacttatac ttctattggt acagacaaat cttggggcag       180
aaagtcgagt ttctggtttc cttttataat aatgaaatct cagagaagtc tgaaatattc       240
gatgatcaat ctcagttgga aaggcctgat ggatcaaatt tcactctgaa gatccggtcc       300
acaaagctgg aggactcagc catgtacttc tgtgccagca gtaaagacta ccggggaggt       360
gaaaaactgt tttttggcag tggaacccag ctctctgtct tggaggacct gaacaaggtg       420
ttcccacccg aggtcgctgt gtttgagcca tcagaagcag agatctccca cacccaaaag       480
gccacactgg tgtgcctggc cacaggcttc ttccccgacc acgtggagct gagctggtgg       540
gtgaatggga aggaggtgca cagtggggtc agcacggacc cgcagcccct caaggagcag       600
cccgccctca atgactccag atactgcctg agcagccgcc tgagggtctc ggccaccttc       660
tggcagaacc cccgcaacca cttccgctgt caagtccagt tctacgggct ctcggagaat       720
gacgagtgga cccaggatag ggccaaaccc gtcacccaga tcgtcagcgc cgaggcctgg       780
ggtagagcag actgtggctt tacctcggtg tcctaccagc aaggggtcct gtctgccacc       840
atcctctatg agatcctgct agggaaggcc accctgtatg ctgtgctggt cagcgccctt       900
gtgttgatgg ccatggtcaa gagaaaggat tcagggcaa agcggagcgg aagcggagcc       960
acaaatttct ctctgctgaa gcaggcaggc gatgtggagg agaaccctgg accaatgatg      1020
aaatccttga gagttttact agtgatcctg tggcttcagt tgagctgggt ttggagccaa      1080
cagaaggagg tggagcagaa ttctggaccc ctcagtgttc cagagggagc cattgcctct      1140
ctcaactgca cttacagtga ccgaggttcc cagtccttct ctggtacag acaatattct       1200 gggaaaagcc ctgagttgat aatgtccata tactccaatg gtgacaaaga agatggaagg      1260
tttacagcac agctcaataa agccagccag tatgtttctc tgctcatcag agactcccag      1320
cccagtgatt cagccaccta cctctgtgcc gccctgaggc ctggtggcta caataagctg      1380 attttttggag cagggaccag gctggctgta cacccaaata tccagaaccc tgaccctgcc      1440
```

-continued

```
gtgtaccagc tgagagactc taaatccagt gacaagtctg tctgcctatt caccgatttt    1500
gattctcaaa caaatgtgtc acaaagtaag gattctgatg tgtatatcac agacaaaact    1560
gtgctagaca tgaggtctat ggacttcaag agcaacagtg ctgtggcctg gagcaacaaa    1620
tctgactttg catgtgcaaa cgccttcaac aacagcatta ttccagaaga caccttcttc    1680
cccagcccag aaagttcctg tgatgtcaag ctggtcgaga aaagctttga aacagatacg    1740
aacctaaact ttcaaaacct gtcagtgatt gggttccgaa tcctcctcct gaaagtggcc    1800
gggtttaatc tgctcatgac gctgcggctg tggtccagct gatga                    1845
```

<210> SEQ ID NO 53
<211> LENGTH: 613
<212> TYPE: PRT
<213> ORGANISM: Homo sapiens

<400> SEQUENCE: 53

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
        50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Lys Asp Tyr Arg Gly Gly Glu Lys Leu Phe Phe Gly Ser Gly
            115                 120                 125

Thr Gln Leu Ser Val Leu Glu Asp Leu Asn Lys Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
        290                 295                 300
```

```
Met Val Lys Arg Lys Asp Phe Arg Ala Lys Arg Ser Gly Ser Gly Ala
305             310                 315                 320

Thr Asn Phe Ser Leu Leu Lys Gln Ala Gly Asp Val Glu Glu Asn Pro
                325                 330                 335

Gly Pro Met Met Lys Ser Leu Arg Val Leu Leu Val Ile Leu Trp Leu
            340                 345                 350

Gln Leu Ser Trp Val Trp Ser Gln Gln Lys Glu Val Glu Gln Asn Ser
        355                 360                 365

Gly Pro Leu Ser Val Pro Glu Gly Ala Ile Ala Ser Leu Asn Cys Thr
    370                 375                 380

Tyr Ser Asp Arg Gly Ser Gln Ser Phe Phe Trp Tyr Arg Gln Tyr Ser
385                 390                 395                 400

Gly Lys Ser Pro Glu Leu Ile Met Ser Ile Tyr Ser Asn Gly Asp Lys
                405                 410                 415

Glu Asp Gly Arg Phe Thr Ala Gln Leu Asn Lys Ala Ser Gln Tyr Val
            420                 425                 430

Ser Leu Leu Ile Arg Asp Ser Gln Pro Ser Asp Ser Ala Thr Tyr Leu
        435                 440                 445

Cys Ala Ala Leu Arg Pro Gly Gly Tyr Asn Lys Leu Ile Phe Gly Ala
    450                 455                 460

Gly Thr Arg Leu Ala Val His Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
    530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
        595                 600                 605

Arg Leu Trp Ser Ser
    610
```

<210> SEQ ID NO 54
<211> LENGTH: 1845
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atggacacct ggctggtgtg ctgggccatc ttttccctgc tgaaggcagg actgaccgag      60
ccagaggtga cccagacacc ttctcaccag gtgacacaga tgggccagga agtgatcctg     120
agatgcgtgc caatcagcaa ccacctgtac ttctattggt accgccagat cctgggccag     180
aaggtggagt tcctggtgtc ctttttacaac aatgagatct ccgagaagtc tgagatcttc     240

-continued

```
gacgatcagt ttagcgtgga gcggcccgat ggctccaact ttaccctgaa gatcagaagc      300
acaaagctgg aggattccgc catgtatttc tgcgcaagct ccaaggacta caggggagga      360
gagaagctgt tctttggctc tggcacccag ctgagcgtgc tggaggacct gaataaggtg      420 ttccccctg aggtggccgt gtttgagcct tccgaggccg agatctctca cacccagaag       480
gccaccctgg tgtgcctggc aaccggcttc tttccagatc acgtggagct gagctggtgg      540
gtgaacggca aggaggtgca cagcggcgtg tccaccgacc cacagcccct gaaggagcag      600
cccgccctga atgatagcag atattgcctg tctagccggc tgagagtgtc cgccaccttt      660
tggcagaacc ctcggaatca cttcagatgt caggtgcagt tttacggcct gagcgagaat      720
gacgagtgga cccaggatag ggccaagccc gtgacacaga tcgtgtccgc cgaggcatgg      780
ggaagggcag actgcggctt cacatccgtg tcttatcagc agggcgtgct gagcgccacc      840
atcctgtatg agatcctgct gggcaaggcc acactgtacg ccgtgctggt gtccgccctg      900
gtgctgatgg ctatggtgaa gcggaaggac tttagggcaa agcgcagcgg atccggagca      960
accaacttct ctctgctgaa gcaggccggc gatgtggagg agaatcctgg cccaatgatg     1020
aagtccctga gagtgctgct ggtcatcctg tggctgcagc tgtcttgggt gtggagccag     1080
cagaaggagg tggagcagaa ctccggacct ctgtctgtgc cagagggagc catcgcctct     1140
ctgaattgta cctacagcga caggggctct cagagcttct tttggtatcg ccagtactct     1200
ggcaagagcc ctgagctgat catgtccatc tattctaacg cgacaaggga ggatggcagg     1260
tttacagccc agctgaataa ggccagccag tacgtgtccc tgctgatccg cgacagccag     1320
ccatccgatt ctgccaccta tctgtgcgcc gccctgaggc caggaggata caacaagctg     1380
atcttcggag caggaacaag actggcagtg cacccaaaca tccagaatcc cgaccctgcc     1440
gtgtatcagc tgagggactc caagtcctct gataagagcg tgtgcctgtt caccgacttt     1500
gattctcaga caaacgtgag ccagtccaag gacagcgacg tgtacatcac cgacaagaca     1560
gtgctggata tgcggagcat ggacttcaag tctaacagcg ccgtggcctg gagcaataag     1620
tccgatttcg cctgcgccaa tgcctttaac aattccatca tccctgagga taccttcttt     1680
ccatctcccg agagctcctg tgacgtgaag ctggtggaga gtctttcga gaccgataca     1740 aacctgaatt ttcagaacct gagcgtgatc ggcttccgga tcctgctgct gaaggtggcc     1800
ggcttcaatc tgctgatgac actgagactg tggtctagct gatga                    1845
```

<210> SEQ ID NO 55
<211> LENGTH: 1803
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 55

```
atgggccccc agctccttgg ctatgtggtc ctttgccttc taggagcagg ccccctggaa       60
gcccaagtga cccagaaccc aagatacctc atcacagtga ctggaaagaa gttaacagtg      120
acttgttctc agaatatgaa ccatgagtat atgtcctggt atcgacaaga cccagggctg      180
ggcttaaggc agatctacta ttcaatgaat gttgaggtga ctgataaggg agatgttcct      240
gaagggtaca agtctctcg aaaagagaag aggaatttcc ccctgatcct ggagtcgccc      300
agccccaacc agacctctct gtacttctgt gccagcaggg ggttagcaac taatgaaaaa      360
ctgttttttg gcagtggaac ccagctctct gtcttggagg acctgaggaa cgtgacccca      420
```

-continued

```
cctaaggtgt ccctgttcga gccttctaag gccgagatcg ccaataagca gaaggccacc    480
ctggtgtgcc tggcaagggg cttctttcca gatcacgtgg agctgagctg gtgggtgaac    540
ggcaaggagg tgcactccgg cgtgtgcacc gacccacagg cctacaagga gagcaattac    600
tcctattgtc tgagctcccg gctgagagtg tccgccacat tttggcacaa ccccaggaat    660
cacttccgct gccaggtgca gtttcacggc ctgagcgagg aggataagtg gcctgagggc    720
tcccctaagc cagtgaccca gaacatctct gccgaggcat ggggaagggc agactgtgga    780
atcaccagcg cctcctatca gcagggcgtg ctgagcgcca caatcctgta cgagatcctg    840
ctgggcaagg ccaccctgta tgccgtgctg gtgtccacac tggtggtcat ggctatggtg    900
aagcggaaga actctagggc aaagcggagc ggaagcggag ccacaaattt ctctctgctg    960
aagcaggcag gcgatgtgga ggagaaccct ggaccaatga catccattcg agctgtattt    1020
atattcctgt ggctgcagct ggacttggtg aatggagaga atgtggagca gcatccttca    1080
accctgagtg tccaggaggg agacagcgct gttatcaagt gtacttattc agacagtgcc    1140
tcaaactact tcccttggta taagcaagaa cttggaaaag acctcagct tattatagac    1200 attcgttcaa atgtgggcga aaagaaagac caacgaattg ctgttacatt gaacaagaca    1260
gccaaacatt tctccctgca catcacagag acccaacctg aagactcggc tgtctacttc    1320
tgtgcagcaa gtaaaggaaa cacacctctt gtctttggaa agggcacaag actttctgtg    1380
attgcaaaca tccagaatcc agagcccgcc gtgtatcagc tgaaggaccc aagatcccag    1440
gattctaccc tgtgcctgtt cacagacttt gattctcaga tcaatgtgcc caagacaatg    1500
gagagcggca ccttcatcac agacaagtgc gtgctggata tgaaggctat ggactccaag    1560
tctaacggcg ccatcgcctg agcaatcag acctccttca catgccagga tatctttaag    1620
gagacaaacg ccacataccc ttctagcgac gtgccatgtg atgccaccct gacagagaag    1680
agcttcgaga cagacatgaa cctgaatttt cagaatctgc tggtcatcgt gctgcggatc    1740
ctgctgctga aggtggctgg gtttaatctg ctgatgacac tgcgactgtg gagtagctga    1800
tga                                                                  1803
```

```
<210> SEQ ID NO 56
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110
```

```
Arg Gly Leu Ala Thr Asn Glu Lys Leu Phe Phe Gly Ser Gly Thr Gln
    115                 120                 125

Leu Ser Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Ala Tyr Lys Glu Ser Asn Tyr Ser Tyr Cys Leu Ser Ser Arg Leu
    195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
            275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Thr Ser Ile
                325                 330                 335

Arg Ala Val Phe Ile Phe Leu Trp Leu Gln Leu Asp Leu Val Asn Gly
                340                 345                 350

Glu Asn Val Glu Gln His Pro Ser Thr Leu Ser Val Gln Glu Gly Asp
            355                 360                 365

Ser Ala Val Ile Lys Cys Thr Tyr Ser Asp Ser Ala Ser Asn Tyr Phe
    370                 375                 380

Pro Trp Tyr Lys Gln Glu Leu Gly Lys Gly Pro Gln Leu Ile Ile Asp
385                 390                 395                 400

Ile Arg Ser Asn Val Gly Glu Lys Lys Asp Gln Arg Ile Ala Val Thr
                405                 410                 415

Leu Asn Lys Thr Ala Lys His Phe Ser Leu His Ile Thr Glu Thr Gln
                420                 425                 430

Pro Glu Asp Ser Ala Val Tyr Phe Cys Ala Ala Ser Lys Gly Asn Thr
            435                 440                 445

Pro Leu Val Phe Gly Lys Gly Thr Arg Leu Ser Val Ile Ala Asn Ile
    450                 455                 460

Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
                500                 505                 510

Asp Met Lys Ala Met Asp Ser Lys Ser Asn Gly Ala Ile Ala Trp Ser
            515                 520                 525
```

-continued

```
Asn Gln Thr Ser Phe Thr Cys Gln Asp Ile Phe Lys Glu Thr Asn Ala
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
                580                 585                 590

Thr Leu Arg Leu Trp Ser Ser
        595
```

```
<210> SEQ ID NO 57
<211> LENGTH: 1803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgggaccac agctgctggg atacgtggtg ctgtgcctgc tgggagcagg accactggag      60
gcacaggtga cccagaaccc tagatatctg atcaccgtga caggcaagaa gctgaccgtg     120
acatgtagcc agaacatgaa tcacgagtac atgtcctggt atcggcagga tcctggcctg     180
ggcctgagac agatctacta tagcatgaat gtggaggtga ccgacaaggg cgatgtgcct     240
gagggctaca aggtgtcccg gaaggagaag agaaacttcc cactgatcct ggagagccca     300
tcccccaatc agacctctct gtatttttgc gcaagcaggg gactggcaac caatgagaag     360
ctgttctttg ctccggcac acagctgtct gtgctggagg acctgagaaa cgtgaccccc     420
cctaaggtga gctgttcga gccctccaag gccgagatcg ccaataagca gaaggccacc     480
ctggtgtgcc tggcaagggg cttctttcct gatcacgtgg agctgtcttg gtgggtgaac     540
ggcaaggagg tgcacagcgg cgtgtgcacc gacccacagg cctacaagga gtctaattac     600
agctattgtc tgagctcccg gctgagagtg tccgccacat tttggcacaa cccaaggaat     660
cacttccgct gccaggtgca gtttcacggc ctgtctgagg aggataagtg gccagaggga     720
agccctaagc cagtgaccca gaacatctcc gccgaggcat ggggaagggc agactgtgga     780
atcacctctg ccagctatca gcagggcgtg ctgagcgcca caatcctgta cgagatcctg     840
ctgggcaagg ccaccctgta tgccgtgctg gtgagcacac tggtggtcat ggctatggtg     900
aagaggaaga actccagggc aaagcggagc ggatctggag ccaccaattt ctctctgctg     960
aagcaggcag gcgatgtgga ggagaatcca ggacctatga catccatccg cgccgtgttc    1020
atctttctgt ggctgcagct ggacctggtg aacggcgaga atgtggagca gcaccctcc     1080 accctgtctg tgcaggaggg cgatagcgcc gtgatcaagt gcacatacag cgactccgcc    1140
tctaactact cccctggta taagcaggag ctgggcaagg cccccagct gatcatcgat    1200 atcaggtcta acgtgggcga agaagaggac cagcgcatcg ccgtgaccct gaataagaca    1260
gccaagcact ttagcctgca catcaccgag acacagcccg aggattccgc cgtgtacttc    1320
tgtgccgcct ctaagggcaa caccccctctg tgtttggca anggcacaag gctgtccgtg    1380
atcgccaaca tccagaatcc agagcccgcc gtgtatcagc tgaaggaccc tcgcagccag    1440
gattccaccc tgtgcctgtt cacagacttt gattcccaga tcaatgtgcc aaagacaatg    1500
gagtctggcc ccttcatcac agacaagtgc gtgctggata tgaaggctat ggacagcaag    1560
tccaacggcg ccatcgcctg gtctaatcag accagcttca catgccagga tatctttaag    1620
```

-continued

```
gagaccaacg ccacatacc ttctagcgac gtgccatgtg atgccaccct gacagagaag    1680
agcttcgaga ccgacatgaa cctgaatttt cagaacctgc tggtcatcgt gctgcggatc    1740
ctgctgctga aggtggccgg ctttaatctg ctgatgacac tgagactgtg gtcctcttga    1800
tga                                                                  1803

<210> SEQ ID NO 58
<211> LENGTH: 1827
<212> TYPE: DNA
<213> ORGANISM: Homo sapiens

<400> SEQUENCE: 58 atgggcccccc agctccttgg ctatgtggtc ctttgccttc taggagcagg ccccctggaa     60
gcccaagtga cccagaaccc aagataccct atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca aagtctctcg aaaagagaag aggaatttcc ccctgatcct ggagtcgccc    300
agccccaacc agacctctct gtacttctgt gccagcaggg ggttagcaac taatgaaaaa    360 ctgtttttg gcagtggaac ccagctctct gtcttggagg acctgaacaa ggtgttccca    420
cccgaggtcg ctgtgtttga gccatcagaa gcagagatct cccacaccca aaaggccaca    480
ctggtgtgcc tggccacagg cttcttcccc gaccacgtgg agctgagctg gtgggtgaat    540
gggaaggagg tgcacagtgg ggtcagcacg gacccgcagc ccctcaagga gcagcccgcc    600
ctcaatgact ccagatactg cctgagcagc cgcctgaggg tctcggccac cttctggcag    660 aaccccccgca accacttccg ctgtcaagtc cagttctacg ggctctcgga gaatgacgag    720
tggacccagg ataggggccaa acccgtcacc cagatcgtca gcgccgaggc ctggggtaga    780
gcagactgtg gctttacctc ggtgtcctac cagcaagggg tcctgtctgc caccatcctc    840
tatgagatcc tgctagggaa ggccaccctg tatgctgtgc tggtcagcgc ccttgtgttg    900
atggccatgg tcaagagaaa ggatttcagg gcaaagcgga gcggaagcgg agccacaaat    960
ttctctctgc tgaagcaggc aggcgatgtg gaggagaacc ctggaccaat gacatccatt   1020
cgagctgtat ttatattcct gtggctgcag ctggacttgg tgaatggaga gaatgtggag   1080
cagcatcctt caaccctgag tgtccaggag ggagacagcc tgttatcaa gtgtacttat   1140 tcagacagtg cctcaaacta cttcccttgg tataagcaag aacttggaaa aggacctcag   1200
cttattatag acattcgttc aaatgtgggc gaaaagaaag accaacgaat tgctgttaca   1260
ttgaacaaga cagccaaaca tttctccctg cacatcacag agacccaacc tgaagactcg   1320
gctgtctact ctgtgcagc aagtaaagga aacacacctc ttgtctttgg aaagggcaca   1380
agactttctg tgattgcaaa tatccagaac cctgaccctg ccgtgtacca gctgagagac   1440
tctaaatcca gtgacaagtc tgtctgccta ttcaccgatt ttgattctca aacaaatgtg   1500
tcacaaagta aggattctga tgtgtatatc acagacaaaa ctgtgctaga catgaggtct   1560
atggacttca agagcaacag tgctgtggcc tggagcaaca atctgactt tgcatgtgca   1620 aacgccttca caacagcat tattccagaa gacaccttct ccccagccc agaaagttcc   1680 tgtgatgtca agctggtcga gaaaagcttt gaaacagata cgaacctaaa ctttcaaaac   1740
ctgtcagtga ttgggttccg aatcctcctc ctgaaagtgg ccgggtttaa tctgctcatg   1800
acgctgcggc tgtggtccag ctgatga                                       1827
```

-continued

<210> SEQ ID NO 59
<211> LENGTH: 607
<212> TYPE: PRT
<213> ORGANISM: Homo sapiens

<400> SEQUENCE: 59

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Arg Gly Leu Ala Thr Asn Glu Lys Leu Phe Phe Gly Ser Gly Thr Gln
        115                 120                 125

Leu Ser Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
            325                 330                 335

Met Thr Ser Ile Arg Ala Val Phe Ile Phe Leu Trp Leu Gln Leu Asp
            340                 345                 350

Leu Val Asn Gly Glu Asn Val Glu Gln His Pro Ser Thr Leu Ser Val
        355                 360                 365

Gln Glu Gly Asp Ser Ala Val Ile Lys Cys Thr Tyr Ser Asp Ser Ala
    370                 375                 380

-continued

```
Ser Asn Tyr Phe Pro Trp Tyr Lys Gln Glu Leu Gly Lys Gly Pro Gln
385             390              395              400

Leu Ile Ile Asp Ile Arg Ser Asn Val Gly Glu Lys Lys Asp Gln Arg
                405              410              415

Ile Ala Val Thr Leu Asn Lys Thr Ala Lys His Phe Ser Leu His Ile
            420              425              430

Thr Glu Thr Gln Pro Glu Asp Ser Ala Val Tyr Phe Cys Ala Ala Ser
        435              440              445

Lys Gly Asn Thr Pro Leu Val Phe Gly Lys Gly Thr Arg Leu Ser Val
    450              455              460

Ile Ala Asn Ile Gln Asn Pro Asp Pro Ala Val Tyr Gln Leu Arg Asp
465              470              475              480

Ser Lys Ser Ser Asp Lys Ser Val Cys Leu Phe Thr Asp Phe Asp Ser
            485              490              495

Gln Thr Asn Val Ser Gln Ser Lys Asp Ser Asp Val Tyr Ile Thr Asp
            500              505              510

Lys Thr Val Leu Asp Met Arg Ser Met Asp Phe Lys Ser Asn Ser Ala
        515              520              525

Val Ala Trp Ser Asn Lys Ser Asp Phe Ala Cys Ala Asn Ala Phe Asn
    530              535              540

Asn Ser Ile Ile Pro Glu Asp Thr Phe Phe Pro Ser Pro Glu Ser Ser
545              550              555              560

Cys Asp Val Lys Leu Val Glu Lys Ser Phe Glu Thr Asp Thr Asn Leu
            565              570              575

Asn Phe Gln Asn Leu Ser Val Ile Gly Phe Arg Ile Leu Leu Leu Lys
            580              585              590

Val Ala Gly Phe Asn Leu Leu Met Thr Leu Arg Leu Trp Ser Ser
        595              600              605
```

```
<210> SEQ ID NO 60
<211> LENGTH: 1827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atgggaccac agctgctggg atacgtggtg ctgtgcctgc tgggagcagg accactggag       60
gcacaggtga cccagaaccc tcggtatctg atcaccgtga caggcaagaa gctgaccgtg      120
acatgttccc agaacatgaa tcacgagtac atgtcttggt ataggcagga ccctggactg      180
ggactgagac agatctacta ttccatgaat gtggaggtga ccgacaaggg cgatgtgcct      240
gagggctaca aggtgtctcg aaggagaag agaaactttc cactgatcct ggagtctcca      300
agccccaatc agacatccct gtatttctgc gcctctagag gcctggccac caacgagaag      360
ctgttctttg gcagcggcac acagctgtcc gtgctggagg acctgaataa ggtgttcccc      420
cctgaggtgg ccgtgtttga gccatctgag gccgagatca gccacaccca gaaggccacc      480
ctggtgtgcc tggcaaccgg cttcttcccc gatcacgtgg agctgtcctg gtgggtgaac      540
ggcaaggagg tgcacagcgg cgtgtccaca gaccctcagc cactgaagga gcagcctgcc      600
ctgaatgatt ccaggtactg cctgagctcc cggctgagag tgtctgccac cttttggcag      660
aacccaagga tcacttccg ctgtcaggtg cagtttatg cctgagcga gaacgacgag      720 tggacccagg atcgggccaa gccagtgaca cagatcgtgt ccgccgaggc atggggaaga      780
```

```
gcagactgcg gcttcacatc cgtgtcttat cagcagggcg tgctgtctgc caccatcctg    840
tacgagatcc tgctgggcaa ggccacactg tatgccgtgc tggtgagcgc cctggtgctg    900
atggctatgg tgaagaggaa ggactttagg gcaaagcgca gcggatccgg agcaaccaac    960
ttctctctgc tgaagcaggc aggcgatgtg gaggagaatc caggacctat gacaagcatc   1020
cgcgccgtgt tcatctttct gtggctgcag ctggatctgg tgaacggcga gaatgtggag   1080
cagcacccct ctaccctgag cgtgcaggag ggcgatagcg ccgtgatcaa gtgtacatac   1140
tctgacagcg cctccaacta ctttccctgg tataagcagg agctgggcaa gggcccccag   1200
ctgatcatcg atatcaggtc caacgtgggc gagaagaagg accagcgcat cgccgtgacc   1260
ctgaataaga cagccaagca cttcagcctg cacatcaccg agacacagcc cgaggactct   1320
gccgtgtact tttgcgccgc cagcaagggc aataccccctc tggtgttcgg caagggcaca   1380
cggctgtccg tgatcgccaa catccagaat ccagatcccg ccgtgtatca gctgagagac   1440
agcaagtcta gcgataagag cgtgtgcctg ttcaccgact ttgatagcca gacaaacgtg   1500
tctcagagca aggactccga cgtgtacatc accgacaaga cagtgctgga tatgcggagc   1560
atggacttta gtccaactc tgccgtggcc tggtccaata agtctgactt cgcctgcgcc   1620
aatgccttta acaattctat catccccgag gataccttct ttcctagccc agagtcctct   1680
tgtgacgtga agctggtgga gaagagcttc gagaccgata caaacctgaa ttttcagaac   1740
ctgtccgtga tcggcttcag gatcctgctg ctgaaggtgg ccggcttcaa tctgctgatg   1800
accctgcgcc tgtggagctc ctgatga                                       1827
```

```
<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Arg Pro Asp Ile Asp Asn Met Asp Glu Tyr Val His Asn Thr Thr
1               5                   10                  15

Ala Arg Ala Phe Ala Val Val Ala Ser
            20                  25

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Pro Asp Ile Asp Asn Met Asp Glu Tyr Val His Asn Thr Thr Ala
1               5                   10                  15

Arg Ala Phe Ala Val Val Ala Ser
            20

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 63

```
Pro Asp Ile Asp Asn Met Asp Glu Tyr Val His Asn Thr Thr Ala Arg
1               5                   10                  15

Ala Phe Ala Val Val Ala Ser
            20
```

```
<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 64

```
Asp Ile Asp Asn Met Asp Glu Tyr Val His Asn Thr Thr Ala Arg Ala
1               5                   10                  15

Phe Ala Val Val Ala Ser
            20
```

```
<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 65

```
Ile Asp Asn Met Asp Glu Tyr Val His Asn Thr Thr Ala Arg Ala Phe
1               5                   10                  15

Ala Val Val Ala Ser
            20
```

```
<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 66

```
Asp Asn Met Asp Glu Tyr Val His Asn Thr Thr Ala Arg Ala Phe Ala
1               5                   10                  15

Val Val Ala Ser
            20
```

```
<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 67

```
Asn Met Asp Glu Tyr Val His Asn Thr Thr Ala Arg Ala Phe Ala Val
1               5                   10                  15

Val Ala Ser
```

```
<210> SEQ ID NO 68
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Asp Glu Tyr Val His Asn Thr Thr Ala Arg Ala Phe Ala Val Val
1               5                   10                  15

Ala Ser

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Glu Tyr Val His Asn Thr Thr Ala Arg Ala Phe Ala Val Val Ala
1               5                   10                  15

Ser

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Tyr Val His Asn Thr Thr Ala Arg Ala Phe Ala Val Val Ala Ser
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Arg Pro Asp Ile Asp Asn Met Asp Glu Tyr Val His Asn Thr Thr
1               5                   10                  15

Ala

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Arg Pro Asp Ile Asp Asn Met Asp Glu Tyr Val His Asn Thr Thr
1               5                   10                  15

Ala Arg

<210> SEQ ID NO 73
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 73

Met Arg Pro Asp Ile Asp Asn Met Asp Glu Tyr Val His Asn Thr Thr
1               5                   10                  15

Ala Arg Ala

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met Arg Pro Asp Ile Asp Asn Met Asp Glu Tyr Val His Asn Thr Thr
1               5                   10                  15

Ala Arg Ala Phe
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Arg Pro Asp Ile Asp Asn Met Asp Glu Tyr Val His Asn Thr Thr
1               5                   10                  15

Ala Arg Ala Phe Ala
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Arg Pro Asp Ile Asp Asn Met Asp Glu Tyr Val His Asn Thr Thr
1               5                   10                  15

Ala Arg Ala Phe Ala Val
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Arg Pro Asp Ile Asp Asn Met Asp Glu Tyr Val His Asn Thr Thr
1               5                   10                  15

Ala Arg Ala Phe Ala Val Val
            20
```

<210> SEQ ID NO 78
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Arg Pro Asp Ile Asp Asn Met Asp Glu Tyr Val His Asn Thr Thr
1               5                   10                  15

Ala Arg Ala Phe Ala Val Val Ala
            20

<210> SEQ ID NO 79
<211> LENGTH: 25
<212> TYPE: PRT
<213> ORGANISM: Homo sapiens

<400> SEQUENCE: 79

Met Arg Pro Asp Ile Asp Asn Met Asp Glu Tyr Val Arg Asn Thr Thr
1               5                   10                  15

Ala Arg Ala Phe Ala Val Val Ala Ser
            20                  25

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 81
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Gly Glu Gly Arg Gly Ser Leu Leu Thr Cys Gly Asp Val Glu
1               5                   10                  15

-continued

```
Glu Asn Pro Gly Pro
          20

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ser Gly Gln Cys Thr Asn Tyr Ala Leu Leu Lys Leu Ala Gly Asp
1               5                   10                  15

Val Glu Ser Asn Pro Gly Pro
          20

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ser Gly Val Lys Gln Thr Leu Asn Phe Asp Leu Leu Lys Leu Ala
1               5                   10                  15

Gly Asp Val Glu Ser Asn Pro Gly Pro
          20                  25

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid

<400> SEQUENCE: 85

Arg Xaa Arg Arg
1

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (3)..(3)
<223> OTHER INFORMATION: Any naturally occurring amino acid
<220> FEATURE:
<221> NAME/KEY: MOD_RES
<222> LOCATION: (4)..(4)
<223> OTHER INFORMATION: Lys or Arg

<400> SEQUENCE: 86
```

-continued

```
Xaa Arg Xaa Xaa Arg
1               5

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any naturally occurring amino acid

<400> SEQUENCE: 87

Arg Xaa Xaa Arg
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Gln Lys Arg
1

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Arg Pro Asp Ile Asp Asn Met Asp Glu Tyr Val Gly Asn Thr Thr
1               5                   10                  15

Ala Arg Ala Phe Ala Val Val Ala Ser
            20                  25

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Arg Pro Asp Ile Asp Asn Met Asp Glu Tyr Val Leu Asn Thr Thr
1               5                   10                  15

Ala Arg Ala Phe Ala Val Val Ala Ser
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

-continued

```
Met Arg Pro Asp Ile Asp Asn Met Asp Glu Tyr Val Cys Asn Thr Thr
1               5                   10                  15

Ala Arg Ala Phe Ala Val Val Ala Ser
            20                  25

<210> SEQ ID NO 92
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atggatacct ggctcgtatg ctgggcaatt tttagtctct tgaaagcagg actcacagaa       60
cctgaagtca cccagactcc cagccatcag gtcacacaga tgggacagga agtgatcttg      120
cgctgtgtcc ccatctctaa tcacttatac ttctattggt acagacaaat cttggggcag      180
aaagtcgagt ttctggtttc cttttataat aatgaaatct cagagaagtc tgaaatattc      240
gatgatcaat tctcagttga aaggcctgat ggatcaaatt tcactctgaa gatccggtcc      300
acaaagctgg aggactcagc catgtacttc tgtgccagca gtaaagacta ccggggaggt      360
gaaaaactgt tttttggcag tggaacccag ctctctgtct tggaggacct gagaaacgtg      420 acaccccta aggtgagcct gttcgagccc tccaaggccg agatcgccaa taagcagaag       480
gccaccctgg tgtgcctggc aaggggcttc tttcctgatc acgtggagct gtcttggtgg      540
gtgaacggca aggaggtgca cagcggcgtg tgcaccgacc cacaggccta taggagagc       600 aattattcct actgtctgtc tagccggctg agagtgagcg ccacattttg cacaaccct       660 cggaatcact tcagatgcca ggtgcagttt cacggcctgt ctgaggagga taagtggcca      720
gagggcagcc caaagccagt gacccagaac atctccgccg aggcatgggg aagagcagac      780
tgtggcatca ccagcgcctc ctaccagcag ggcgtgctgt ccgccacaat cctgtatgag      840
atcctgctgg gcaaggccac cctgtacgcc gtgctggtga gcacactggt ggtcatggct      900
atggtgaaga ggaagaactc c                                                921

<210> SEQ ID NO 93
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgatgaaat ccttgagagt tttactagtg atcctgtggc ttcagttgag ctgggtttgg       60
agccaacaga aggaggtgga gcagaattct ggacccctca gtgttccaga gggagccatt      120
gcctctctca actgcactta cagtgaccga ggttcccagt ccttcttctg gtacagacaa      180
tattctggga aaagccctga gttgataatg tccatatact ccaatggtga caaagaagat      240
ggaaggttta cagcacagct caataaagcc agccagtatg tttctctgct catcagagac      300
tcccagccca gtgattcagc cacctacctc tgtgccgccc tgaggcctgg tggctacaat      360
aagctgattt ttggagcagg gaccaggctg gctgtacacc caaacatcca gaatccagag      420
cccgccgtgt atcagctgaa ggacccaaga tcccaggatt ctaccctgtg cctgttcaca      480
gactttgatt ctcagatcaa tgtgcccaag acaatggaga gcggcacctt catcacagac      540
```

-continued

```
aagtgcgtgc tggatatgaa ggctatggac tccaagtcta acggcgccat cgcctggagc     600
aatcagacct ccttcacatg ccaggatatc tttaaggaga caaacgccac atacccttct     660
agcgacgtgc catgtgatgc caccctgaca gagaagagct tcgagacaga catgaacctg     720
aattttcaga atctgctggt catcgtgctg cggatcctgc tgctgaaggt ggctgggttt     780
aatctgctga tgacactgcg actgtggagt agctgatga                          819
```

```
<210> SEQ ID NO 94
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
```

```
atggacacct ggctggtgtg ctgggccatc ttctctctgc tgaaggcagg actgaccgag      60
ccagaggtga cccagacacc ttcccaccag gtgacacaga tgggccagga agtgatcctg     120
agatgcgtgc caatcagcaa ccacctgtac ttttattggt accgccagat cctgggccag     180
aaggtggagt cctggtgtc cttttataac aatgagatca gcgagaagtc cgagatcttc     240
gacgatcagt tttctgtgga gcggcccgat ggcagcaatt tcaccctgaa gatcagatcc     300
acaaagctgg aggattctgc catgtatttt tgcgcaagct ccaaggacta caggggagga     360
gagaagctgt tctttggaag cggaacccag ctgtccgtgc tggaggacct gcgcaacgtg     420
acacccccta aggtgtctct gttcgagcca agcaaggccg agatcgccaa taagcagaag     480
gccaccctgg tgtgcctggc aaggggcttc tttcccgatc acgtggagct gtcctggtgg     540
gtgaacggca aggaggtgca ctctggcgtg tgcaccgacc ctcaggccta taaggagtct     600
aattatagct actgtctgtc tagccggctg agagtgagcg ccacattttg gcacaacccc     660
cggaatcact tcagatgcca ggtgcagttt cacggcctgt ccgaggagga taagtggcct     720
gagggctctc caaagcccgt gacccagaac atcacgcgcg aggcatgggg aagggcagac     780
tgtggaatca cctctgccag ctaccagcag ggcgtgctgt ccgccacaat cctgtatgag     840
atcctgctgg gcaaggccac cctgtacgcc gtgctggtgt ctacactggt ggtcatggct     900
atggtgaagc ggaagaacag c                                              921
```

```
<210> SEQ ID NO 95
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
```

```
atgatgaaga gcctgagagt gctgctggtc atcctgtggc tgcagctgtc ctgggtgtgg      60
tctcagcaga aggaggtgga gcagaacagc ggaccactgt ccgtgccaga gggagccatc     120
gccagcctga attgcaccta ctccgacagg ggcagccagt ccttcttttg gtatcgccag     180
tactccggca gtctcctga gctgatcatg agcatctatt ccaacggcga caaggaggat     240
ggccggttca cagcccagct gaataaggcc tctcagtacg tgagcctgct gatcagagat     300
tcccagccat ctgatagcgc cacctacctg tgcgccgccc tgaggccagg aggctacaac     360
aagctgatct ttggagcagg aacaagactg gcagtgcacc taacatcca gaatcccgag     420 cctgccgtgt atcagctgaa ggacccacgg tctcaggata gcaccctgtg cctgttcaca     480
```

-continued

```
gactttgata gccagatcaa tgtgcccaag acaatggagt ccggcacctt catcacagac      540
aagtgcgtgc tggatatgaa ggctatggac tccaagtcta acggcgccat cgcctggtcc      600
aatcagacct ctttcacatg ccaggatatc tttaaggaga ccaacgccac atacccttcc      660
tctgacgtgc catgtgatgc caccctgaca gagaagagct cgagaccga catgaacctg       720 aattttcaga acctgctggt catcgtgctg aggatcctgc tgctgaaggt ggccggcttt      780
aatctgctga tgacactgcg cctgtggagc tcctgatga                             819
```

```
<210> SEQ ID NO 96
<211> LENGTH: 933
<212> TYPE: DNA
<213> ORGANISM: Homo sapiens

<400> SEQUENCE: 96
atggatacct ggctcgtatg ctgggcaatt tttagtctct tgaaagcagg actcacagaa      60
cctgaagtca cccagactcc cagccatcag gtcacacaga tgggacagga agtgatcttg      120
cgctgtgtcc ccatctctaa tcacttatac ttctattggt acagacaaat cttggggcag      180
aaagtcgagt ttctggtttc ctttttataat aatgaaatct cagagaagtc tgaaatattc     240
gatgatcaat tctcagttga aaggcctgat ggatcaaatt tcactctgaa gatccggtcc      300
acaaagctgg aggactcagc catgtacttc tgtgccagca gtaaagacta ccggggaggt      360
gaaaaactgt tttttggcag tggaacccag ctctctgtct tggaggacct gaacaaggtg      420
ttcccacccg aggtcgctgt gtttgagcca tcagaagcag agatctccca cacccaaaag      480
gccacactgg tgtgcctggc cacaggcttc ttccccgacc acgtggagct gagctggtgg      540
gtgaatggga aggaggtgca cagtggggtc agcacggacc cgcagcccct caaggagcag      600
cccgccctca tgactccag atactgcctg agcagccgcc tgagggtctc ggccaccttc       660
tggcagaacc ccgcaacca cttccgctgt caagtccagt tctacgggct ctcggagaat       720
gacgagtgga cccaggatag gccaaaccc gtcacccaga tcgtcagcgc cgaggcctgg       780
ggtagagcag actgtggctt tacctcggtg tcctaccagc aagggtcct gtctgccacc       840 atcctctatg agatcctgct agggaaggcc accctgtatg ctgtgctggt cagcgccctt      900
gtgttgatgg ccatggtcaa gagaaaggat ttc                                   933
```

```
<210> SEQ ID NO 97
<211> LENGTH: 831
<212> TYPE: DNA
<213> ORGANISM: Homo sapiens

<400> SEQUENCE: 97
atgatgaaat ccttgagagt tttactagtg atcctgtggc ttcagttgag ctgggtttgg      60
agccaacaga aggaggtgga gcagaattct ggacccctca gtgttccaga gggagccatt      120
gcctctctca actgcactta cagtgaccga ggttcccagt ccttcttctg gtacagacaa      180
tattctggga aaagccctga gttgataatg tccatatact ccaatggtga caaagaagat      240 ggaaggtta cagcacagct caataaagcc agccagtatg tttctctgct catcagagac      300 tcccagcca gtgattcagc cacctacctc tgtgccgcc tgaggcctgg tggctacaat        360
aagctgattt ttggagcagg gaccaggctg ctgtacacc caaatatcca gaaccctgac       420
cctgccgtgt accagctgag agactctaaa tccagtgaca gtctgtctg cctattcacc       480 gattttgatt ctcaaacaaa tgtgtcacaa agtaaggatt ctgatgtgta tatcacagac      540
```

```
aaaactgtgc tagacatgag gtctatggac ttcaagagca acagtgctgt ggcctggagc      600
aacaaatctg actttgcatg tgcaaacgcc ttcaacaaca gcattattcc agaagacacc      660
ttcttcccca gcccagaaag ttcctgtgat gtcaagctgg tcgagaaaag ctttgaaaca      720
gatacgaacc taaactttca aaacctgtca gtgattgggt tccgaatcct cctcctgaaa      780
gtggccgggt ttaatctgct catgacgctg cggctgtggt ccagctgatg a               831
```

<210> SEQ ID NO 98
<211> LENGTH: 933
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
atggacacct ggctggtgtg ctgggccatc ttttccctgc tgaaggcagg actgaccgag       60
ccagaggtga cccagacacc ttctcaccag gtgacacaga tgggccagga agtgatcctg      120
agatgcgtgc caatcagcaa ccacctgtac ttctattggt accgccagat cctgggccag      180
aaggtggagt cctggtgtc cttttacaac aatgagatct ccgagaagtc tgagatcttc      240
gacgatcagt ttagcgtgga gcggcccgat ggctccaact ttaccctgaa gatcagaagc      300
acaaagctgg aggattccgc catgtatttc tgcgcaagct ccaaggacta caggggagga      360
gagaagctgt tctttggctc tggcacccag ctgagcgtgc tggaggacct gaataaggtg      420 ttccccctg aggtggccgt gtttgagcct tccgaggccg agatctctca cacccagaag      480 gccacctgg tgtgcctggc aaccggcttc tttccagatc acgtggagct gagctggtgg      540
gtgaacggca aggaggtgca cagcggcgtg tccaccgacc cacagccct gaaggagcag      600 cccgccctga atgatagcag atattgcctg tctagccggc tgagagtgtc cgccaccttt      660
tggcagaacc ctcggaatca cttcagatgt caggtgcagt tttacggcct gagcgagaat      720
gacgagtgga cccaggatag ggccaagccc gtgacacaga tcgtgtccgc cgaggcatgg      780
ggaagggcag actgcggctt cacatccgtg tcttatcagc agggcgtgct gagcgccacc      840
atcctgtatg agatcctgct gggcaaggcc acactgtacg ccgtgctggt gtccgccctg      900
gtgctgatgg ctatggtgaa gcggaaggac ttt                                   933
```

<210> SEQ ID NO 99
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atgatgaagt ccctgagagt gctgctggtc atcctgtggc tgcagctgtc ttgggtgtgg       60
agccagcaga aggaggtgga gcagaactcc ggacctctgt ctgtgccaga gggagccatc      120
gcctctctga attgtaccta cagcgacagg ggctctcaga gcttcttttg gtatcgccag      180
tactctggca agagccctga gctgatcatg tccatctatt ctaacggcga caaggaggat      240
ggcaggttta cagcccagct gaataaggcc agccagtacg tgtccctgct gatccgcgac      300
agccagccat ccgattctgc cacctatctg tgcgccgccc tgaggccagg aggatacaac      360
aagctgatct cggagcagg aacaagactg gcagtgcacc caaacatcca gaatcccgac      420
cctgccgtgt atcagctgag ggactccaag tcctctgata gagagcgtgtg cctgttcacc      480
```

-continued

```
gactttgatt ctcagacaaa cgtgagccag tccaaggaca gcgacgtgta catcaccgac          540
aagacagtgc tggatatgcg gagcatggac ttcaagtcta acagcgccgt ggcctggagc          600
aataagtccg atttcgcctg cgccaatgcc tttaacaatt ccatcatccc tgaggatacc          660
ttctttccat ctcccgagag ctcctgtgac gtgaagctgg tggagaagtc tttcgagacc          720
gatacaaacc tgaattttca gaacctgagc gtgatcggct ccggatcct gctgctgaag           780 gtggccggct tcaatctgct gatgacactg agactgtggt ctagctgatg a                   831
```

<210> SEQ ID NO 100
<211> LENGTH: 915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
atgggccccc agctccttgg ctatgtggtc ctttgccttc taggagcagg cccccctggaa         60 gcccaagtga cccagaaccc aagatacctc atcacagtga ctggaaagaa gttaacagtg          120
acttgttctc agaatatgaa ccatgagtat atgtcctggt atcgacaaga cccagggctg          180
ggcttaaggc agatctacta ttcaatgaat gttgaggtga ctgataaggg agatgttcct          240
gaagggtaca aagtctctcg aaaagagaag aggaatttcc ccctgatcct ggagtcgccc          300
agccccaacc agacctctct gtacttctgt gccagcaggg ggttagcaac taatgaaaaa          360 ctgtttttg gcagtggaac ccagctctct gtcttggagg acctgaggaa cgtgaccccca         420 cctaaggtgt ccctgttcga gccttctaag gccgagatcg ccaataagca gaaggccacc          480
ctggtgtgcc tggcaagggg cttctttcca gatcacgtgg agctgagctg gtgggtgaac          540
ggcaaggagg tgcactccgg cgtgtgcacc gacccacagg cctacaagga gagcaattac          600
tcctattgtc tgagctcccg gctgagagtg tccgccacat tttggcacaa ccccaggaat          660
cacttccgct gccaggtgca gtttcacggc ctgagcgagg aggataagtg gcctgagggc          720
tcccctaagc cagtgaccca gaacatctct gccgaggcat ggggaagggc agactgtgga          780
atcaccagcg cctcctatca gcagggcgtg ctgagcgcca caatcctgta cgagatcctg          840
ctgggcaagg ccaccctgta tgccgtgctg gtgtccacac tggtggtcat ggctatggtg          900
aagcggaaga actct                                                           915
```

<210> SEQ ID NO 101
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
atgacatcca ttcgagctgt atttatattc ctgtggctgc agctggactt ggtgaatgga          60
gagaatgtgg agcagcatcc ttcaaccctg agtgtccagg agggagacag cgctgttatc          120
aagtgtactt attcagacag tgcctcaaac tacttccctt ggtataagca agaacttgga          180
aaaggacctc agcttattat agacattcgt tcaaatgtgg gcgaaaagaa agaccaacga          240
attgctgtta cattgaacaa gacagccaaa catttctccc tgcacatcac agagacccaa          300
cctgaagact cggctgtcta cttctgtgca gcaagtaaag gaaacacacc tcttgtcttt         360
```

-continued

```
ggaaagggca caagactttc tgtgattgca aacatccaga atccagagcc cgccgtgtat       420
cagctgaagg acccaagatc ccaggattct accctgtgcc tgttcacaga ctttgattct       480
cagatcaatg tgcccaagac aatggagagc ggcaccttca tcacagacaa gtgcgtgctg       540
gatatgaagg ctatggactc caagtctaac ggcgccatcg cctggagcaa tcagacctcc       600
ttcacatgcc aggatatctt taaggagaca aacgccacat acccttctag cgacgtgcca       660
tgtgatgcca ccctgacaga gaagagcttc gagacagaca tgaacctgaa ttttcagaat       720
ctgctggtca tcgtgctgcg gatcctgctg ctgaaggtgg ctgggtttaa tctgctgatg       780
acactgcgac tgtggagtag ctgatga                                           807
```

```
<210> SEQ ID NO 102
<211> LENGTH: 915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
```

```
atgggaccac agctgctggg atacgtggtg ctgtgcctgc tgggagcagg accactggag        60
gcacaggtga cccagaaccc tagatatctg atcaccgtga caggcaagaa gctgaccgtg       120
acatgtagcc agaacatgaa tcacgagtac atgtcctggt atcggcagga tcctggcctg       180
ggcctgagac agatctacta tagcatgaat gtggaggtga ccgacaaggg cgatgtgcct       240
gagggctaca aggtgtcccg gaaggagaag agaaacttcc cactgatcct ggagagccca       300
tcccccaatc agacctctct gtattttgc gcaagcaggg gactggcaac caatgagaag        360
ctgttctttg gctccggcac acagctgtct gtgctggagg acctgagaaa cgtgaccccc       420
cctaaggtga gcctgttcga gccctccaag gccgagatcg ccaataagca gaaggccacc       480
ctggtgtgcc tggcaagggg cttctttcct gatcacgtgg agctgtcttg gtgggtgaac       540
ggcaaggagg tgcacagcgg cgtgtgcacc gacccacagg cctacaagga gtctaattac       600
agctattgtc tgagctcccg gctgagagtg tccgccacat tttggcacaa cccaaggaat       660
cacttccgct gccaggtgca gtttcacggc ctgtctgagg aggataagtg gccagaggga       720
agccctaagc cagtgaccca gaacatctcc gccgaggcat ggggaagggc agactgtgga       780
atcacctctg ccagctatca gcaggcgtg ctgagcgcca caatcctgta cgagatcctg        840
ctgggcaagg ccaccctgta tgccgtgctg gtgagcacac tggtggtcat ggctatggtg       900
aagaggaaga actcc                                                        915
```

```
<210> SEQ ID NO 103
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
```

```
atgacatcca tccgcgccgt gttcatcttt ctgtggctgc agctggacct ggtgaacggc        60
gagaatgtgg agcagcaccc ctccaccctg tctgtgcagg agggcgatag cgccgtgatc       120
aagtgcacat acagcgactc cgcctctaac tacttcccct ggtataagca ggagctgggc       180
aagggccccc agctgatcat cgatatcagg tctaacgtgg gcgagaagaa ggaccagcgc       240
atcgccgtga ccctgaataa gacagccaag cactttagcc tgcacatcac cgagacacag       300
```

-continued

```
cccgaggatt ccgccgtgta cttctgtgcc gcctctaagg gcaacacccc tctggtgttt        360
ggcaagggca caaggctgtc cgtgatcgcc aacatccaga atccagagcc cgccgtgtat        420
cagctgaagg accctcgcag ccaggattcc accctgtgcc tgttcacaga ctttgattcc        480
cagatcaatg tgccaaagac aatggagtct ggcaccttca tcacagacaa gtgcgtgctg        540
gatatgaagg ctatggacag caagtccaac ggcgccatcg cctggtctaa tcagaccagc        600
ttcacatgcc aggatatctt taaggagacc aacgccacat acccttctag cgacgtgcca        660
tgtgatgcca ccctgacaga gaagagcttc gagaccgaca tgaacctgaa ttttcagaac        720
ctgctggtca tcgtgctgcg gatcctgctg ctgaaggtgg ccggctttaa tctgctgatg        780
acactgagac tgtggtcctc ttgatga                                           807

<210> SEQ ID NO 104
<211> LENGTH: 927
<212> TYPE: DNA
<213> ORGANISM: Homo sapiens

<400> SEQUENCE: 104 atgggcccccc agctccttgg ctatgtggtc ctttgccttc taggagcagg cccccctggaa        60 gcccaagtga cccagaaccc aagatacctc atcacagtga ctggaaagaa gttaacagtg        120
acttgttctc agaatatgaa ccatgagtat atgtcctggt atcgacaaga cccagggctg        180
ggcttaaggc agatctacta ttcaatgaat gttgaggtga ctgataaggg agatgttcct        240
gaagggtaca aagtctctcg aaaagagaag aggaatttcc ccctgatcct ggagtcgccc        300
agccccaacc agacctctct gtacttctgt gccagcaggg ggttagcaac taatgaaaaa        360
ctgttttttg gcagtggaac ccagctctct gtcttggagg acctgaacaa ggtgttccca        420
cccgaggtcg ctgtgtttga gccatcagaa gcagagatct cccacaccca aaaggccaca        480
ctggtgtgcc tggccacagg cttcttcccc gaccacgtgg agctgagctg gtgggtgaat        540
gggaaggagg tgcacagtgg ggtcagcacg gacccgcagc ccctcaagga gcagcccgcc        600
ctcaatgact ccagatactg cctgagcagc cgcctgaggg tctcggccac cttctggcag        660
aacccccgca accacttccg ctgtcaagtc cagttctacg ggctctcgga gaatgacgag        720
tggacccagg ataggggccaa acccgtcacc cagatcgtca gcgccgaggc ctggggtaga        780
gcagactgtg gctttacctc ggtgtcctac cagcaagggg tcctgtctgc caccatcctc        840
tatgagatcc tgctagggaa ggccacctg tatgctgtgc tggtcagcgc ccttgtgttg        900
atggccatgg tcaagagaaa ggatttc                                           927

<210> SEQ ID NO 105
<211> LENGTH: 819
<212> TYPE: DNA
<213> ORGANISM: Homo sapiens

<400> SEQUENCE: 105
atgacatcca ttcgagctgt atttatattc ctgtggctgc agctggactt ggtgaatgga        60
gagaatgtgg agcagcatcc ttcaaccctg agtgtccagg agggagacag cgctgttatc        120
aagtgtactt attcagacag tgcctcaaac tacttccctt ggtataagca agaacttgga        180
aaaggacctc agcttattat agacattcgt tcaaatgtgg cgaaaagaa agaccaacga        240 attgctgtta cattgaacaa gacagccaaa catttctccc tgcacatcac agagacccaa        300
cctgaagact cggctgtcta cttctgtgca gcaagtaaag gaaacacacc tcttgtctttt        360
```

-continued

```
ggaaagggca caagactttc tgtgattgca aatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa aactgtgcta    540
gacatgaggt ctatggactt caagagcaac agtgctgtgg cctggagcaa caaatctgac    600
tttgcatgtg caaacgcctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agctgatga                          819
```

<210> SEQ ID NO 106
<211> LENGTH: 927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
atgggaccac agctgctggg atacgtggtg ctgtgcctgc tgggagcagg accactggag     60
gcacaggtga cccagaaccc tcggtatctg atcaccgtga caggcaagaa gctgaccgtg    120
acatgttccc agaacatgaa tcacgagtac atgtcttggt ataggcagga ccctggactg    180
ggactgagac agatctacta ttccatgaat gtggaggtga ccgacaaggg cgatgtgcct    240
gagggctaca aggtgtctcg gaaggagaag agaaactttc cactgatcct ggagtctcca    300
agccccaatc agacatccct gtatttctgc gcctctagag gcctggccac caacgagaag    360
ctgttctttg gcagcggcac acagctgtcc gtgctggagg acctgaataa ggtgttcccc    420
cctgaggtgg ccgtgtttga gccatctgag gccgagatca gccacaccca gaaggccacc    480
ctggtgtgcc tggcaaccgg cttctttccc gatcacgtgg agctgtcctg gtgggtgaac    540
ggcaaggagg tgcacagcgg cgtgtccaca gaccctcagc cactgaagga gcagcctgcc    600
ctgaatgatt ccaggtactg cctgagctcc cggctgagag tgtctgccac cttttggcag    660
aacccaagga tcacttccg ctgtcaggtg cagtttttatg cctgagcga gaacgacgag    720 tggacccagg atcgggccaa gccagtgaca cagatcgtgt ccgccgaggc atggggaaga    780
gcagactgcg gcttcacatc cgtgtcttat cagcagggcg tgctgtctgc caccatcctg    840
tacgagatcc tgctgggcaa ggccacactg tatgccgtgc tggtgagcgc cctggtgctg    900
atggctatgg tgaagaggaa ggacttt                                       927
```

<210> SEQ ID NO 107
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
atgacaagca tccgcgccgt gttcatcttt ctgtggctgc agctggatct ggtgaacggc     60
gagaatgtgg agcagcaccc ttctaccctg agcgtgcagg agggcgatag cgccgtgatc    120
aagtgtacat actctgacag cgcctccaac tactttccct ggtataagca ggagctgggc    180
aagggccccc agctgatcat cgatatcagg tccaacgtgg gcgagaagaa ggaccagcgc    240
atcgccgtga ccctgaataa gacagccaag cacttcagcc tgcacatcac cgagacacag    300
```

-continued

```
cccgaggact ctgccgtgta cttttgcgcc gccagcaagg gcaataccccc tctggtgttc    360 ggcaagggca cacggctgtc cgtgatcgcc aacatccaga atccagatcc cgccgtgtat    420
cagctgagag acagcaagtc tagcgataag agcgtgtgcc tgttcaccga ctttgatagc    480
cagacaaacg tgtctcagag caaggactcc gacgtgtaca tcaccgacaa gacagtgctg    540
gatatgcgga gcatggactt taagtccaac tctgccgtgg cctggtccaa taagtctgac    600
ttcgcctgcg ccaatgcctt taacaattct atcatccccg aggatacctt ctttcctagc    660
ccagagtcct cttgtgacgt gaagctggtg gagaagagct cgagaccga tacaaacctg    720 aattttcaga acctgtccgt gatcggcttc aggatcctgc tgctgaaggt ggccggcttc    780
aatctgctga tgaccctgcg cctgtggagc tcctgatga                            819
```

```
<210> SEQ ID NO 108
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally occurring amino acid

<400> SEQUENCE: 108

Arg Xaa Lys Arg
1
```

T CELL RECEPTORS TARGETING MUTATIONS IN RNA SPLICING FACTORS

CLAIM OF PRIORITY

This application is a National Stage application under 35 U.S.C. § 371 of International Application No. PCT/US2020/062164, having an International Filing Date of Nov. 25, 2020, which This application claims priority to U.S. Provisional Application No. 62/940,725, filed on Nov. 26, 2019, the entire contents of which is hereby incorporated by reference.

SEQUENCE LISTING

This document contains a sequence listing that has been submitted electronically as an ASCII text file. The ASCII text file, created on Jan. 15, 2021 is 118 kilobytes in size. The material in the ASCII text file is hereby incorporated by reference in its entirety.

BACKGROUND

1. Technical Field

This document relates to isolated immune cells that include an exogenous T cell receptor (TCR) having affinity for a splicing factor 3B subunit 1A (SF3B1) peptide as well as methods and materials for making such immune cells. For example, this document provides isolated immune cells that included an exogenous TCR having affinity for a mutant SF3B1 peptide, methods and materials for making such immune cells, and methods and materials for using such immune cells to treat mammals (e.g., a human having cancer).

2. Background Information

RNA splicing is a fundamental process in eukaryotes, which is carried out by the splicing machinery (spliceosome). Splicing factor 3b subunit 1 (SF3B1) is a component of the U2 small nuclear ribonucleoproteins complex, which is involved in RNA alternative splicing. Mutant SF3B1 results in abnormal splicing of several genes, primarily due to misrecognition of 3' splice sites. Many of the resulting aberrant mRNAs undergo nonsense-mediated mRNA decay (NMD), leading to reduced gene expression. See, for example, Giuseppe Liberante, et al., Sci. Rep., 9:2678 (2019). Missense mutations in SF3B1 are associated with the development and progression of multiple malignant diseases, including myelodysplastic syndromes, breast cancer, and chronic lymphocytic leukemia (CLL).

SUMMARY

This document is based, at least in part, on the discoveries of T cell receptors (TCRs) having affinity for a SF3B1 (Splicing Factor 3B Subunit 1A) peptide, e.g., a mutant SF3B1 peptide. As described herein, TCRs provided herein bind to a mutant SF3B1 peptide (within the context of an MHC molecule such as DRB3) have an alpha chain and a beta chain. In some embodiments, the alpha chain includes (i) the amino acid sequences set forth in SEQ ID NO:10, SEQ ID NO:11, and SEQ ID NO:12, or (ii) the amino acid sequences set forth in SEQ ID NO:10 and SEQ ID NO:11 with no more than one amino acid modification, and the amino acid sequence set forth in SEQ ID NO:12 with no more than two amino acid modifications, and the beta chain includes (i) the amino acid sequences set forth in SEQ ID NO: 1, SEQ ID NO:2, and SEQ ID NO:3, or (ii) the amino acid sequences set forth in SEQ ID NO:1 and SEQ ID NO:2 with no more than one amino acid modification, and the amino acid sequence set forth in SEQ ID NO:3 with no more than two amino acid modifications. The amino acid modifications can be an amino acid substitution, an amino acid deletion, or an amino acid addition. In some embodiments, the alpha chain includes (i) the amino acid sequences set forth in SEQ ID NO:32, SEQ ID NO:33, and SEQ ID NO:34, or (ii) the amino acid sequences set forth in SEQ ID NO:32 and SEQ ID NO:33 with no more than one amino acid modification and the amino acid sequence set forth in SEQ ID NO:34 with no more than two amino acid modifications, and the beta chain includes (i) the amino acid sequences set forth in SEQ ID NO: 23, SEQ ID NO:24, and SEQ ID NO:25, or (ii) the amino acid sequences set forth in SEQ ID NO:23 and SEQ ID NO:24 with no more than one amino acid modification, and the amino acid sequence set forth in SEQ ID NO:25 with no more than two amino acid modifications. The amino acid modifications can be an amino acid substitution, an amino acid deletion, or an amino acid addition.

Immune cells (e.g., T cells) modified to include an exogenous TCR having affinity for a SF3B1 peptide (e.g., a mutant SF3B1 peptide) as described herein can be used to treat a mammal having cancer. Mutations in SF3B1 are commonly found, for example, in uveal melanoma, chronic lymphocytic leukemia, myelodysplastic syndromes, and breast cancer.

In one aspect, this document features an isolated immune cell (e.g., a T cell) comprising an exogenous TCR having affinity for a splicing factor 3B subunit TA (SF3B1) peptide. The exogenous TCR includes an alpha chain and a beta chain, where the alpha chain includes (i) the amino acid sequences set forth in SEQ ID NO:10, SEQ ID NO:11, and SEQ ID NO:12, or (ii) the amino acid sequences set forth in SEQ ID NO:10 and SEQ ID NO: 11 with no more than one amino acid modification and the amino acid sequence set forth in SEQ ID NO:12 with no more than two amino acid modifications, wherein the amino acid modifications are selected from the group consisting of amino acid substitutions, amino acid deletions, and amino acid additions, and the beta chain includes (i) the amino acid sequences set forth in SEQ ID NO: 1, SEQ ID NO:2, and SEQ ID NO:3, or (ii) the amino acid sequences set forth in SEQ ID NO:1 and SEQ ID NO:2 with no more than one amino acid modification and the amino acid sequence set forth in SEQ ID NO:3 with no more than two amino acid modifications, wherein the amino acid modifications are selected from the group consisting of amino acid substitutions, amino acid deletions, and amino acid additions.

In some cases, the alpha chain comprises an amino sequence having at least 80 percent identity, at least 90 percent identity, or at least 95 percent identity to the amino acid sequence set forth in SEQ ID NO:18 or SEQ ID NO:22. In some cases, the alpha chain includes the amino acid sequence set forth in SEQ ID NO: 10. In some cases, the alpha chain includes the amino acid sequence set forth in SEQ ID NO: 11. In some cases, the alpha chain includes the amino acid sequence set forth in SEQ ID NO: 12. In some cases, the alpha chain includes the amino acid sequence set forth in SEQ ID NO: 10, SEQ ID NO: 11, and SEQ ID NO:12.

In some cases, the beta chain comprises an amino acid sequence having at least 80 percent identity, at least 90 percent identity, or at least 95 percent identity to the amino acid sequence set forth in SEQ ID NO:9 or SEQ ID NO:20. In some cases, the beta chain includes the amino acid sequence set forth in SEQ ID NO: 1. In some cases, the beta chain includes the amino acid sequence set forth in SEQ ID NO:2. In some cases, the beta chain includes the amino acid sequence set forth in SEQ ID NO:3. In some cases, the beta chain comprises the amino acid sequence set forth in SEQ ID NO:1, SEQ ID NO: 2 and SEQ ID NO:3.

This document also features an isolated immune cell (e.g., a T cell) that includes an exogenous TCR having affinity for a SF3B1 peptide (e.g., a SF3B1 peptide comprising a histidine at the position corresponding to 625 in the human SF3B1 protein). The exogenous TCR includes an alpha chain and a beta chain, where the alpha chain includes (i) the amino acid sequences set forth in SEQ ID NO: 32, SEQ ID NO:33, and SEQ ID NO:34, or (ii) the amino acid sequences set forth in SEQ ID NO:32 and SEQ ID NO:33 with no more than one amino acid modification, and the amino acid sequence set forth in SEQ ID NO:34 with no more than two amino acid modifications, wherein the amino acid modifications are selected from the group consisting of amino acid substitutions, amino acid deletions, and amino acid additions; and the beta chain includes (i) the amino acid sequences set forth in SEQ ID NO:23, SEQ ID NO:24, and SEQ ID NO:25, or (ii) the amino acid sequences set forth in SEQ ID NO:23 and SEQ ID NO:24 with no more than one amino acid modification and the amino acid sequence set forth in SEQ ID NO:25 with no more than two amino acid modifications, wherein the amino acid modifications are selected from the group consisting of amino acid substitutions, amino acid deletions, and amino acid additions.

In some cases, the alpha chain includes an amino sequence having at least 80 percent identity, at least 90 percent identity, or at least 95 percent identity to the amino acid sequence set forth in SEQ ID NO:40 or SEQ ID NO:44. In some cases, the alpha chain includes the amino acid sequence set forth in SEQ ID NO:32. In some cases, the alpha chain includes the amino acid sequence set forth in SEQ ID NO:33. In some cases, the alpha chain includes the amino acid sequence set forth in SEQ ID NO:34. In some cases, the alpha chain includes the amino acid sequence set forth in SEQ ID NO:32, SEQ ID NO:33, and SEQ ID NO:34.

In some cases, the beta chain includes an amino acid sequence having at least 80 percent identity, at least 90 percent identity, or at least 95 percent identity to the amino acid sequence set forth in SEQ ID NO:31 or SEQ ID NO:42. In some cases, the beta chain includes the amino acid sequence set forth in SEQ ID NO:23. In some cases, the beta chain includes the amino acid sequence set forth in SEQ ID NO:24. In some cases, the beta chain includes the amino acid sequence set forth in SEQ ID NO: 25. In some cases, the beta chain includes the amino acid sequence set forth in SEQ ID NO:23, SEQ ID NO: 24 and SEQ ID NO:25.

In any of the embodiments, the immune cell can be a T cell. Expression of the endogenous TCR alpha and beta chain coding sequences can be downregulated in the T cell.

This document also features a nucleic acid molecule that includes a nucleic acid sequence encoding an alpha chain of a TCR having affinity for a SF3B1 peptide and a nucleic acid sequence encoding a beta chain of the TCR. In some cases, the alpha chain includes (i) the amino acid sequences set forth in SEQ ID NO: 10, SEQ ID NO:11, and SEQ ID NO:12, or (ii) the amino acid sequences set forth in SEQ ID NO: 10 and SEQ ID NO:11 with no more than one amino acid modification and the amino acid sequence set forth in SEQ ID NO:12 with no more than two amino acid modifications, wherein the amino acid modifications are selected from the group consisting of amino acid substitutions, amino acid deletions, and amino acid additions, and the beta chain includes (i) the amino acid sequences set forth in SEQ ID NO:1, SEQ ID NO:2, and SEQ ID NO:3, or (ii) the amino acid sequences set forth in SEQ ID NO:1 and SEQ ID NO:2 with no more than one amino acid modification and the amino acid sequence set forth in SEQ ID NO:3 with no more than two amino acid modifications, wherein the amino acid modifications are selected from the group consisting of amino acid substitutions, amino acid deletions, and amino acid additions. In some cases, the alpha chain includes (i) the amino acid sequences set forth in SEQ ID NO:32, SEQ ID NO:33, and SEQ ID NO: 34, or (ii) the amino acid sequences set forth in SEQ ID NO:32 and SEQ ID NO:33 with no more than one amino acid modification and the amino acid sequence set forth in SEQ ID NO: 34 with no more than two amino acid modifications, wherein the amino acid modifications are selected from the group consisting of amino acid substitutions, amino acid deletions, and amino acid additions; and the beta chain includes (i) the amino acid sequences set forth in SEQ ID NO:23, SEQ ID NO:24, and SEQ ID NO:25, or (ii) the amino acid sequences set forth in SEQ ID NO:23 and SEQ ID NO:24 with no more than one amino acid modification and the amino acid sequence set forth in SEQ ID NO:25 with no more than two amino acid modifications, wherein the amino acid modifications are selected from the group consisting of amino acid substitutions, amino acid deletions, and amino acid additions.

In some cases, the alpha chain comprises an amino sequence having at least 80 percent identity, at least 90 percent identity, or at least 95 percent identity to the amino acid sequence set forth in SEQ ID NO:18 or SEQ ID NO:22. In some cases, the alpha chain includes the amino acid sequence set forth in SEQ ID NO: 10. In some cases, the alpha chain includes the amino acid sequence set forth in SEQ ID NO: 11. In some cases, the alpha chain includes the amino acid sequence set forth in SEQ ID NO: 12. In some cases, the alpha chain includes the amino acid sequence set forth in SEQ ID NO: 10, SEQ ID NO: 11, and SEQ ID NO:12. In some cases, the beta chain comprises an amino acid sequence having at least 80 percent identity, at least 90 percent identity, or at least 95 percent identity to the amino acid sequence set forth in SEQ ID NO:9 or SEQ ID NO:20. In some cases, the beta chain includes the amino acid sequence set forth in SEQ ID NO: 1. In some cases, the beta chain includes the amino acid sequence set forth in SEQ ID NO:2. In some cases, the beta chain includes the amino acid sequence set forth in SEQ ID NO:3. In some cases, the beta chain comprises the amino acid sequence set forth in SEQ ID NO:1, SEQ ID NO: 2 and SEQ ID NO:3.

In some cases, the alpha chain includes an amino sequence having at least 80 percent identity, at least 90 percent identity, or at least 95 percent identity to the amino acid sequence set forth in SEQ ID NO:40 or SEQ ID NO:44. In some cases, the alpha chain includes the amino acid sequence set forth in SEQ ID NO:32. In some cases, the alpha chain includes the amino acid sequence set forth in SEQ ID NO:33. In some cases, the alpha chain includes the amino acid sequence set forth in SEQ ID NO:34. In some cases, the alpha chain includes the amino acid sequence set forth in SEQ ID NO:32, SEQ ID NO:33, and SEQ ID NO:34. In some cases, the beta chain includes an amino acid sequence having at least 80 percent identity, at least 90 percent identity, or at least 95 percent identity to the amino acid sequence set forth in SEQ ID NO:31 or SEQ ID NO:42.

In some cases, the beta chain includes the amino acid sequence set forth in SEQ ID NO:23. In some cases, the beta chain includes the amino acid sequence set forth in SEQ ID NO:24. In some cases, the beta chain includes the amino acid sequence set forth in SEQ ID NO:25. In some cases, the beta chain includes the amino acid sequence set forth in SEQ ID NO:23, SEQ ID NO:24 and SEQ ID NO:25.

In any of the embodiments, the nucleic acid can include a promotor 5' of the nucleic acid sequence encoding the alpha chain and/or can include a promoter 5' of the nucleic acid sequence encoding the beta chain. The promoter can be a viral 5' long terminal repeat or a viral 3' long terminal repeat.

In any of the embodiments, the nucleic acid can be a vector, e.g., a viral vector such as a retroviral vector or a lentiviral vector.

In any of the embodiments, the nucleic acid further can include a nucleic acid sequence encoding a linker. In some cases, the linker can be 3' of the nucleic acid sequence encoding the alpha chain and 5' of the nucleic acid sequence encoding the beta chain. In some cases, the linker can be 3' of the nucleic acid sequence encoding the beta chain and 5' of the nucleic acid sequence encoding the alpha chain. In some cases, the linker is a self-cleaving peptide (e.g., a self-cleaving peptide of a foot-and-mouth disease virus (FMDV), an equine rhinitis A virus (ERAVO, a *Thosea asigna* virus (TaV), or a porcine tescho virus-1 (PTV-1)). In some cases, the self-cleaving peptide is a P2A peptide. In some cases, the linker includes a furin cleavage site.

This document also features a method of making an immune cell (e.g., a T cell) that includes an exogenous TCR having affinity for a SF3B1 peptide. The method includes introducing, into the immune cell, a nucleic acid molecule that includes a nucleic acid sequence encoding an alpha chain of a TCR having affinity for a SF3B1 peptide and a nucleic acid sequence encoding a beta chain of the TCR, wherein the exogenous TCR is expressed from the nucleic acid in the immune cell.

In another aspect, this document features an isolated immune cell that includes a nucleic acid molecule and includes an exogenous TCR having affinity for a SF3B1 peptide. The nucleic acid molecule includes a nucleic acid sequence encoding an alpha chain of a TCR having affinity for a SF3B1 peptide and a nucleic acid sequence encoding a beta chain of the TCR.

This document also features a population of cells that include at least one isolated immune cell, where the isolated immune cell includes a nucleic acid molecule and includes an exogenous TCR having affinity for a SF3B1 peptide. This document also features a pharmaceutical composition that includes the population of cells and a pharmaceutically acceptable carrier. A method for treating a mammal (e.g., a human) in need thereof also is provided that includes administering to the mammal an effective amount of the pharmaceutical composition. The mammal can have cancer (e.g., a cancer selected from the group consisting of melanoma, chronic lymphocytic leukemia, a myelodysplastic syndrome, and breast cancer). The immune cells can be autologous to the mammal.

In another aspect, this document features a method for providing a mammal (e.g., a human) with immune cells that include an exogenous TCR having affinity for a SF3B1 peptide. The method includes administering, to the mammal, the population of cells. The mammal can have cancer (e.g., a cancer selected from the group consisting of melanoma, chronic lymphocytic leukemia, a myelodysplastic syndrome, and breast cancer). The immune cells can be autologous to the mammal.

A method for providing a mammal (e.g., a human) with cells comprising a TCR having affinity for a SF3B1 peptide also is provided. The method includes delivering, to the mammal, a nucleic acid molecule that includes a nucleic acid sequence encoding an alpha chain of a TCR having affinity for a SF3B1 peptide and a nucleic acid sequence encoding a beta chain of the TCR, wherein the nucleic acid is expressed in cells of the mammal. The mammal can have cancer (e.g., a cancer selected from the group consisting of melanoma, chronic lymphocytic leukemia, a myelodysplastic syndrome, and breast cancer). The immune cells can be autologous to the mammal.

In another aspect, this document features a method for treating a mammal (e.g., a human) having cancer. The method includes administering, to the mammal, a population of cells that include at least one isolated immune cell, where the isolated immune cell includes a nucleic acid molecule and includes an exogenous TCR having affinity for a SF3B1 peptide or administering a nucleic acid molecule that includes a nucleic acid sequence encoding an alpha chain of a TCR having affinity for a SF3B1 peptide and a nucleic acid sequence encoding a beta chain of the TCR. The immune cells can be autologous to the mammal.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A contains an alignment of the mutant SF3B1 peptide (SEQ ID NO:61) containing a histidine at the position corresponding to 625 in the human SF3B1 protein and a wild-type SF3B1 peptide (SEQ ID NO:79) containing an arginine at the position corresponding to 625 in the human SF3B1 protein.

FIG. 1B contains the nucleotide sequence encoding the TRBV2-01+TRAV12-02 chimeric TCR (SEQ ID NO:49) and the amino acid sequence of the TRBV2-01+TRAV12-02 chimeric TCR (SEQ ID NO:50).

FIG. 2 contains an exemplary codon optimized nucleotide sequence encoding the TRBV2-01+TRAV12-02 chimeric TCR (SEQ ID NO:51) and the amino acid sequence of the TRBV2-01+TRAV12-02 chimeric TCR (SEQ ID NO:50).

FIG. 3 contains the nucleotide sequence encoding the human TRBV2-01+TRAV12-02 TCR (SEQ ID NO:52) and the amino acid sequence of the human TRBV2-01+TRAV12-02 TCR (SEQ ID NO:53).

FIG. 4 contains an exemplary codon optimized nucleotide sequence encoding a human TRBV2-01+TRAV12-02 TCR (SEQ ID NO:54) and the amino acid sequence of the human TRBV2-01+TRAV12-02 TCR (SEQ ID NO:53).

FIG. 5 contains the nucleotide sequence encoding a TRBV27-01+TRAV13-01 chimeric TCR (SEQ ID NO:55) and the amino acid sequence of the TRBV27-01+TRAV13-01 chimeric TCR (SEQ ID NO:56).

FIG. 6 contains an exemplary codon optimized nucleotide sequence encoding the TRBV27-01+TRAV13-01 chimeric TCR (SEQ ID NO:57) and the amino acid sequence of the TRBV27-01+TRAV13-01 chimeric TCR (SEQ ID NO:56).

FIG. 7 contains the nucleotide sequence encoding a human TRBV27-01+TRAV13-01 TCR (SEQ ID NO:58) and the amino acid sequence of the human TRBV27-01+TRAV13-01 TCR (SEQ ID NO:59).

FIG. 8 contains an exemplary codon optimized nucleotide sequence encoding the human TRBV27-01+TRAV13-01 (SEQ ID NO:60) TCR and the amino acid sequence of the human TRBV27-01+TRAV13-01 TCR (SEQ ID NO:59).

FIG. 10 contains the amino acid sequences set forth in Table 2.

FIG. 11A contains the nucleotide sequence encoding the beta chain of TRBV2-01+TRAV12-02 chimeric TCR (SEQ ID NO:92), with human beta variable region in larger font, CDR1, CDR2, CDR3 underlined, and mouse beta constant in italics.

FIG. 11B contains the nucleotide sequence encoding the alpha chain of TRBV2-01+TRAV12-02 chimeric TCR (SEQ ID NO:93), with human alpha variable region in larger font, CDR1, CDR2, CDR3 underlined, and mouse alpha constant in italics.

FIG. 12A contains the codon optimized nucleotide sequence encoding the beta chain of TRBV2-01+TRAV12-02 chimeric TCR (SEQ ID NO:94), with human beta variable region in larger font, CDR1, CDR2, CDR3 underlined, and mouse beta constant in italics.

FIG. 12B contains the codon optimized nucleotide sequence encoding the alpha chain of TRBV2-01+TRAV12-02 chimeric TCR (SEQ ID NO:95), with human alpha variable region in larger font, CDR1, CDR2, CDR3 underlined, and mouse alpha constant in italics.

FIG. 13A contains the nucleotide sequence encoding the beta chain of TRBV2-01+TRAV12-02 human TCR (SEQ ID NO:96), with human beta variable region in larger font, CDR1, CDR2, CDR3 underlined, and human beta constant in italics.

FIG. 13B contains the nucleotide sequence encoding the alpha chain of TRBV2-01+TRAV12-02 human TCR (SEQ ID NO:97), with human alpha variable region in larger font, CDR1, CDR2, CDR3 underlined, and human alpha constant in italics.

FIG. 14A contains the codon optimized nucleotide sequence encoding the beta chain of TRBV2-01+TRAV12-02 human TCR (SEQ ID NO:98), with human beta variable region in larger font, CDR1, CDR2, CDR3 underlined, and human beta constant in italics.

FIG. 14B contains the codon optimized nucleotide sequence encoding the alpha chain of TRBV2-01+TRAV12-02 human TCR (SEQ ID NO:99), with human alpha variable region in larger font, CDR1, CDR2, CDR3 underlined, and human alpha constant in italics.

FIG. 15A contains the nucleotide sequence encoding the beta chain of TRBV27-01+TRAV13-01 Chimeric TCR (SEQ ID NO: 100), with human beta variable region in larger font, CDR1, CDR2, CDR3 underlined, and mouse beta constant (codon optimized) in italics.

FIG. 15B contains the nucleotide sequence encoding the alpha chain of TRBV27-01+TRAV13-01 Chimeric TCR (SEQ ID NO: 101), with the human variable region in larger font, CDR1, CDR2, CDR3 underlined, and mouse alpha constant (codon optimized) in italics.

FIG. 16A contains the codon optimized nucleotide sequence encoding the beta chain of TRBV27-01+TRAV13-01 Chimeric TCR (SEQ ID NO:102), with human variable region in larger font, CDR1, CDR2, CDR3 underlined, and mouse beta constant in italics.

FIG. 16B contains the codon optimized nucleotide sequence encoding the alpha chain of TRBV27-01+TRAV13-01 Chimeric TCR (SEQ ID NO:103), with human variable region in larger font, CDR1, CDR2, CDR3 underlined, and mouse alpha constant in italics.

FIG. 17A contains the nucleotide sequence encoding the beta chain of TRBV27-01+TRAV13-01 human TCR (SEQ ID NO: 104), with human variable region in larger font, CDR1, CDR2, CDR3 underlined, and human beta constant in italics.

FIG. 17B contains the nucleotide sequence encoding the alpha chain of TRBV27-01+TRAV13-01 human TCR (SEQ ID NO: 105), with human variable region in larger font, CDR1, CDR2, CDR3 underlined, and human alpha constant in italics.

FIG. 18A contains the codon-optimized nucleotide sequence encoding the beta chain of TRBV27-01+TRAV13-01 human TCR (SEQ ID NO:106), with human variable region in larger font, CDR1, CDR2, CDR3 underlined, and human beta constant in italics.

FIG. 18B contains the codon-optimized nucleotide sequence encoding the alpha chain of TRBV27-01+TRAV13-01 human TCR (SEQ ID NO:107), with the human variable region in larger font, CDR1, CDR2, CDR3 underlined, and human alpha constant in italics.

DETAILED DESCRIPTION

Figure 9:
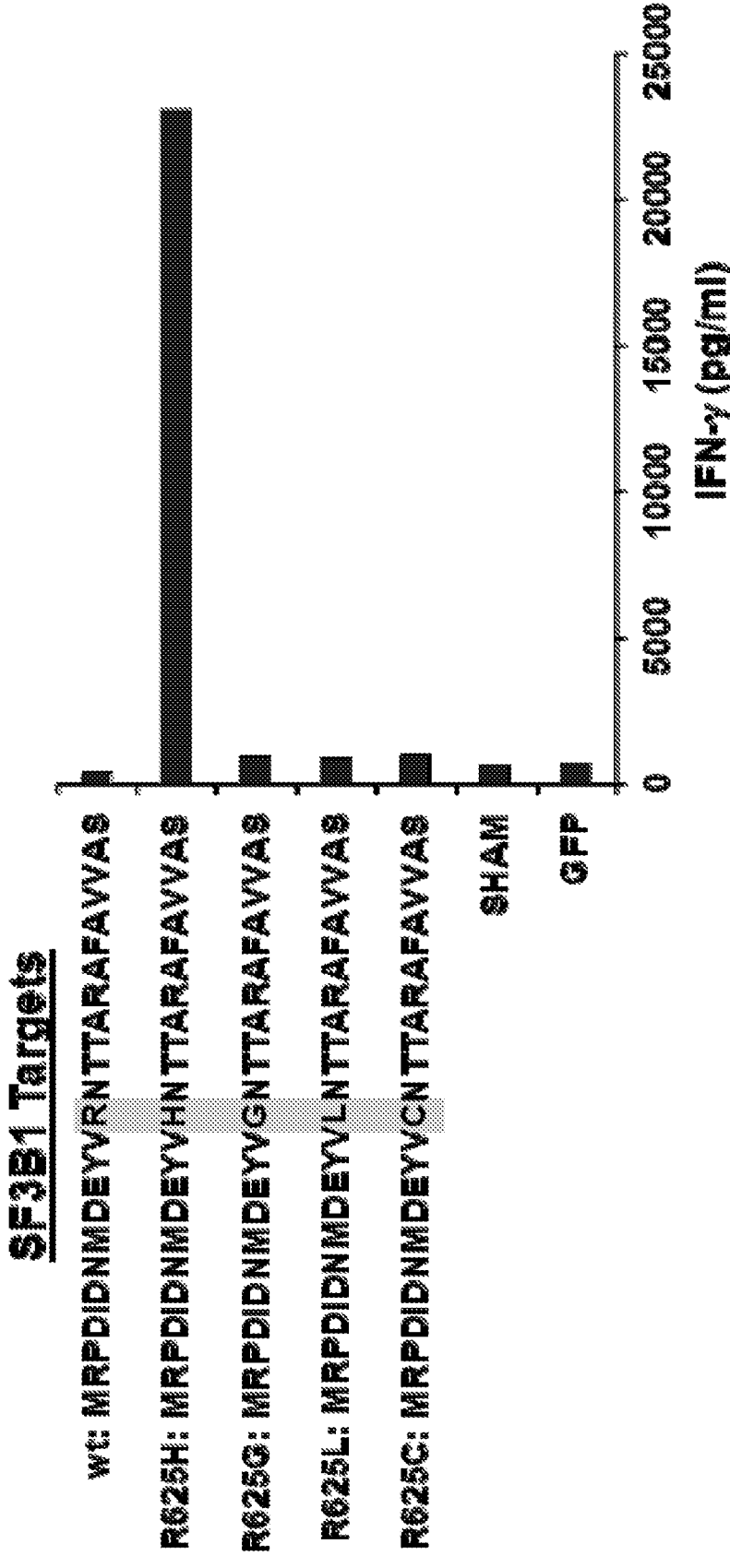
FIG. 9 contains a graph of interferon gamma (IFNγ) (pg/mL) in the supernatant after TCR-transduced T cells were co-cultured overnight with dendritic cells expressing wildtype (wt) SF3B1 (SEQ ID NO:79) or mutated forms of SF3B1 (R625H (SEQ ID NO:61), R625G (SEQ ID NO:89), R625L (SEQ ID NO:90), or R625C (SEQ ID NO:91)).

This document provides TCRs having affinity for a SF3B1 peptide, e.g., a mutant SF3B1 peptide (within the context of an MHC molecule presenting that SF3B1 peptide). The amino acid sequence of human SF3B1 is set forth in UniProtKB Accession No. 075533-1. See also Gene ID 23451 for the human SF3B1 gene. Mutations in SF3B1 are commonly found, for example, in uveal melanoma, chronic lymphocytic leukemia, myelodysplastic syndromes, and breast cancer. In some cases, the TCRs provided herein can have specific affinity for a mutant SF3B1 peptide (e.g., a mutant SF3B1 peptide comprising a histidine at the position corresponding to 625 in the human SF3B1 protein) within the context of an MHC molecule (e.g., DRB3) presenting that SF3B1 peptide. For example, the TCRs provided herein, and cells expressing such TCRs (e.g., immune cells), can have reactivity against a mutant SF3B1 peptide comprising a histidine at the position corresponding to 625 in the human SF3B1 protein without having reactivity to the wild-type of SF3B1 (e.g., having an arginine at the position corresponding to 625 in the human SF3B1 protein) or other mutants at the position corresponding to 625 in the human SF3B1 protein (e.g., having a glycine, cysteine, or leucine at the position corresponding to 625 in the human SF3B1 protein). See FIG. 1A for an alignment of a mutant SF3B1 peptide (SEQ ID NO:61) comprising a histidine at the position corresponding to 625 in the human SF3B1 protein and a wild-type SF3B1 peptide (SEQ ID NO:79) having an arginine at the position corresponding to 625 in the human SF3B1 protein.

A mutant SF3B1 peptide can be from 8 to 30 amino acids in length. Examples of mutant SF3B1 peptides that can be recognized by a TCR provided herein are set forth in Table 1.

TABLE 1

Exemplary mutant SF3B1 peptides

| Sequence | SEQ ID NO: |
|---|---|
| MRPDIDNMDEYVHNTTARAFAVVAS | 61 |
| RPDIDNMDEYVHNTTARAFAVVAS | 62 |
| PDIDNMDEYVHNTTARAFAVVAS | 63 |
| DIDNMDEYVHNTTARAFAVVAS | 64 |
| IDNMDEYVHNTTARAFAVVAS | 65 |
| DNMDEYVHNTTARAFAVVAS | 66 |
| NMDEYVHNTTARAFAVVAS | 67 |
| MDEYVHNTTARAFAVVAS | 68 |
| DEYVHNTTARAFAVVAS | 69 |
| EYVHNTTARAFAVVAS | 70 |
| MRPDIDNMDEYVHNTTA | 71 |
| MRPDIDNMDEYVHNTTAR | 72 |
| MRPDIDNMDEYVHNTTARA | 73 |
| MRPDIDNMDEYVHNTTARAF | 74 |
| MRPDIDNMDEYVHNTTARAFA | 75 |
| MRPDIDNMDEYVHNTTARAFAV | 76 |
| MRPDIDNMDEYVHNTTARAFAVV | 77 |
| MRPDIDNMDEYVHNTTARAFAVVA | 78 |

For example, immune cells that include an exogenous TCR provided herein can be used to treat mammals (e.g., humans having cancer) who harbor the same or similar SF3B1 mutations. For example, immune cells that include an exogenous TCR provided herein can be used to treat melanoma (e.g., uveal melanoma) and/or other cancers such as chronic lymphocytic leukemia, a myelodysplastic syndrome, or breast cancer.

A TCR is a heterodimeric cell surface protein and is involved in mediating signal transduction. The extracellular portion of a native heterodimeric TCR includes two polypeptide chains, each of which has a membrane-proximal constant domain, and a membrane-distal variable domain. The variable domains contain highly polymorphic loops analogous to the complementarity determining regions (CDRs) of antibodies.

In general, the TCRs provided herein include an alpha chain polypeptide and a beta chain polypeptide, where the alpha chain and the beta chain each include three CDRs and a constant region. In some cases, the alpha chain polypeptide can include a CDR1 having the amino acid sequence set forth in SEQ ID NO:10 (or a variant with one, two, or three amino acid modifications), a CDR2 having the amino acid sequence set forth in SEQ ID NO:11 (or a variant with one, two, or three amino acid modifications), and a CDR3 having the amino acid sequence set forth in SEQ ID NO: 12 (or a variant with one, two, or three amino acid modifications), and the beta chain polypeptide can include a CDR1 having the amino acid sequence set forth in SEQ ID NO:1 (or a variant with one, two, or three amino acid modifications), a CDR2 having the amino acid sequence set forth in SEQ ID NO:2 (or a variant with one, two, or three amino acid modifications), and a CDR3 having the amino acid sequence set forth in SEQ ID NO:3 (or a variant with one, two, or three amino acid modifications). In some cases, the alpha chain polypeptide can include a CDR1 having the amino acid sequence set forth in SEQ ID NO:32 (or a variant with one, two, or three amino acid modifications), a CDR2 having the amino acid sequence set forth in SEQ ID NO:33 (or a variant with one, two, or three amino acid modifications), and a CDR3 having the amino acid sequence set forth in SEQ ID NO:34 (or a variant with one, two, or three amino acid modifications), and the beta chain polypeptide can include a CDR1 having the amino acid sequence set forth in SEQ ID NO:23 (or a variant with one, two, or three amino acid modifications), a CDR2 having the amino acid sequence set forth in SEQ ID NO:24 (or a variant with one, two, or three amino acid modifications), and a CDR3 having the amino acid sequence set forth in SEQ ID NO:25 (or a variant with one, two, or three amino acid modifications).

Examples of amino acid modifications with respect to the amino acid sequence set forth in SEQ ID NOs:1, 2, 3, 10, 11, 12, 23, 24, 25, 32, 33, and 34 include, without limitation, amino acid substitutions, amino acid deletions, and amino acid additions. In some cases, a variant of SEQ ID NOs:3, 12, 25, or 34 can include no more than one amino acid modification. Amino acid modifications can be made, for example, to improve the binding and/or contact with the SF3B1 peptide.

In some cases, an amino acid substitution that can be engineered into a TCR containing the sequence set forth in SEQ ID NO:1, 2, 3, 10, 11, 12, 23, 24, 25, 32, 33, or 34 can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution that can be engineered into a TCR containing the sequence set forth in SEQ ID NO:1, 2, 3, 10, 11, 12, 23, 24, 25, 32, 33, or 34 can be a non-conservative amino acid substitution. Non-conservative amino acid substitutions can be made by substituting one amino acid residue for another amino acid residue having a dis-similar side chain. Examples of non-conservative substitutions that can be used as described herein include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating amino acid sequence variants can include site-specific mutagenesis or random mutagenesis (e.g., by PCR) of the nucleic acid encoding the alpha and/or beta chain polypeptide. See, for example, Zoller, Curr. Opin. Biotechnol. 3: 348-354 (1992). Both naturally occurring and non-naturally occurring amino acids (e.g., artificially-de-rivatized amino acids) can be used to generate amino acid sequence variants of the alpha and/or beta chain polypep-tides provided herein.

In some cases, the constant region of an alpha chain polypeptide of a TCR provided herein can have an amino acid sequence having at least 80% identity to the amino acid sequence set forth in SEQ ID NO:17 or SEQ ID NO:21 For example, the constant region of an alpha chain polypeptide of a TCR provided herein can have an amino acid sequence having at least 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:17 or SEQ ID NO:21.

In some cases, the variable region of an alpha chain polypeptide of a TCR provided herein can have an amino acid sequence having at least 80% identity to the amino acid sequence set forth in SEQ ID NO:45 provided that the alpha chain includes the appropriate combination of CDRs (or variants of the CDRs) described herein. For example, the variable region of an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:45, provided that it includes (a) SEQ ID NO:10 (or SEQ ID NO:10 with no more than three, two, or one amino acid modifications), (b) SEQ ID NO:11 (or SEQ ID NO:11 with no more than three, two, or one amino acid modifications), and (c) SEQ ID NO: 12 (or SEQ ID NO:12 with no more than three, two, or one amino acid modifications).

In some cases, the variable region of an alpha chain polypeptide of a TCR provided herein can include the amino acid sequence set forth in SEQ ID NO:45 (or a variant of SEQ ID NO:45 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:45 can be conservative amino acid substi-tutions or non-conservative amino acid substitutions as discussed above for SEQ ID NOs:1, 2, 3, 10, 11, 12, 23, 24, 25, 32, 33, and 34. In some cases, a variant of SEQ ID NO:45 can include no more than one, two, three, four, or five amino acid modifications.

In some cases, an alpha chain polypeptide of a TCR provided herein can have an amino acid sequence having at least 80% identity to the amino acid sequence set forth in SEQ ID NO:18 or SEQ ID NO:22, provided that the alpha chain includes the appropriate combination of CDRs (or variants of the CDRs) described herein. For example, an alpha chain of a TCR provided herein can have an amino acid sequence having at least 80%, 82%, 83%, 84%, 85%, 86%, 87%, 88%, 89%, 90%9, 91%, 92%, 93%, 94%, 95%, 96%, 97%, 98%, 99%, or 100% identity to the amino acid sequence set forth in SEQ ID NO: 18, provided that it includes (a) SEQ ID NO:10 (or SEQ ID NO:10 with no more than three, two, or one amino acid modifications), (b) SEQ ID NO:11 (or SEQ ID NO:11 with no more than three, two, or one amino acid modifications), and (c) SEQ ID NO: 12 (or SEQ ID NO: 12 with no more than three, two, or one amino acid modifications). In another example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:22, provided that it includes (a) SEQ ID NO:10 (or SEQ ID NO:10 with no more than three, two, or one amino acid modifications), (b) SEQ ID NO:11 (or SEQ ID NO: 11 with no more than three, two, or one amino acid modifications), and (c) SEQ ID NO: 12 (or SEQ ID NO: 12 with no more than three, two, or one amino acid modifications).

In some cases, an alpha chain polypeptide of a TCR provided herein can include the amino acid sequence set forth in SEQ ID NO:18 (or a variant of SEQ ID NO:18 with one, two, three, four, five, six, seven, eight, nine, or 10 amino acid modifications, provided that the alpha chain includes the appropriate combination of CDRs (or variants of the CDRs) described herein) or SEQ ID NO:22 (or a variant of SEQ ID NO:22 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substi-tutions for SEQ ID NO:18 or SEQ ID NO:22 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:18 or SEQ ID NO:22 can include no more than one, two, three, four, or five amino acid modifications.

In some cases, the constant region of a beta chain poly-peptide of a TCR provided herein can have an amino acid sequence having at least 80% identity to the amino acid sequence set forth in SEQ ID NO:8 or SEQ ID NO:19. For example, the constant region of a beta chain polypeptide of a TCR provided herein can have an amino acid sequence having at least 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:8 or SEQ ID NO:19.

In some cases, the variable region of a beta chain poly-peptide of a TCR provided herein can have an amino acid sequence having at least 80% identity to the amino acid sequence set forth in SEQ ID NO:47, provided that the beta chain includes the appropriate combination of CDRs (or variants of the CDRs) described herein. For example, the variable region of a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:47, provided that it includes (a) SEQ ID NO:1 (or SEQ ID NO:1 with no more than three, two, or one amino acid modifica-tions), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications).

In some cases, the variable region of a beta chain poly-peptide of a TCR provided herein can include the amino acid sequence set forth in SEQ ID NO:47 (or a variant of SEQ ID NO:47 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:47 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:47 can include no more than one, two, three, four, or five amino acid modifications.

In some cases, a beta chain polypeptide of a TCR provided herein can have an amino acid sequence having at least 80% identity to the amino acid sequence set forth in SEQ ID NO:9 or SEQ ID NO:20, provided that the beta chain includes the appropriate combination of CDRs (or variants of the CDRs) described herein. For example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:9, provided that it includes (a) SEQ ID NO:1 (or SEQ ID NO:1 with no more than three, two, or one amino acid modifications), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications). In another example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:20, provided that it includes (a) SEQ ID NO:1 (or SEQ ID NO:1 with no more than three, two, or one amino acid modifications), (b) SEQ ID NO:2 (or SEQ ID NO:2 with no more than three, two, or one amino acid modifications), and (c) SEQ ID NO:3 (or SEQ ID NO:3 with no more than three, two, or one amino acid modifications).

In some cases, a beta chain polypeptide of a TCR provided herein can have an amino acid sequence having at least 80% identity to the amino acid sequence set forth the amino acid sequence set forth in SEQ ID NO:9 (or a variant of SEQ ID NO:9 with one, two, three, four, five, six, seven, eight, nine, or 10 amino acid modifications, provided that the beta chain includes the appropriate combination of CDRs (or variants of the CDRs) described herein) or SEQ ID NO:20 (or a variant of SEQ ID NO:20 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:9 or SEQ ID NO:20 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:9 or SEQ ID NO:20 can include no more than one, two, three, four, or five amino acid modifications.

In some cases, the constant region of an alpha chain polypeptide of a TCR provided herein can have an amino acid sequence having at least 80% identity to the amino acid sequence set forth in SEQ ID NO:39 or SEQ ID NO:43. For example, the constant region of an alpha chain polypeptide of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:39 or SEQ ID NO:43.

In some cases, the variable region of an alpha chain polypeptide of a TCR provided herein can have an amino acid sequence having at least 80% identity to the amino acid sequence set forth in SEQ ID NO:46, provided that the alpha chain includes the appropriate combination of CDRs (or variants of the CDRs) described herein. For example, the variable region of an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:46, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO:34 (or SEQ ID NO:34 with no more than three, two, or one amino acid modifications).

In some cases, the variable region of an alpha chain polypeptide of a TCR provided herein can include the amino acid sequence set forth in SEQ ID NO:46 (or a variant of SEQ ID NO:46 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:46 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:46 can include no more than one, two, three, four, or five amino acid modifications.

In some cases, an alpha chain polypeptide of a TCR provided herein can have an amino acid sequence having at least 80% identity to the amino acid sequence set forth in SEQ ID NO:40 or SEQ ID NO:44, provided that the alpha chain includes the appropriate combination of CDRs (or variants of the CDRs) described herein. For example, an alpha chain of a TCR provided herein can have an amino acid sequence having at least 80%, 82%, 83%, 84%, 85%, 86%, 87%, 88%, 89%, 90%9, 91%, 92%, 93%, 94%, 95%, 96%, 97%, 98%, 99%, or 100% identity to the amino acid sequence set forth in SEQ ID NO:40, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO:34 (or SEQ ID NO:34 with no more than three, two, or one amino acid modifications). In another example, an alpha chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:44, provided that it includes (a) SEQ ID NO:32 (or SEQ ID NO:32 with no more than three, two, or one amino acid modifications), (b) SEQ ID NO:33 (or SEQ ID NO:33 with no more than three, two, or one amino acid modifications), and (c) SEQ ID NO: 34 (or SEQ ID NO:34 with no more than three, two, or one amino acid modifications).

In some cases, an alpha chain polypeptide of a TCR provided herein can include the amino acid sequence set forth in SEQ ID NO:40 (or a variant of SEQ ID NO:40 with one, two, three, four, five, six, seven, eight, nine, or 10 amino acid modifications, provided that the alpha chain includes the appropriate combination of CDRs (or variants of the CDRs) described herein) or SEQ ID NO:44 (or a variant of SEQ ID NO:44 with one, two, three, four, five, six, seven, eight, nine, or 10 amino acid modifications, provided that the alpha chain includes the appropriate combination of CDRs (or variants of the CDRs) described herein). Amino acid modifications can be amino acid substitutions, amino acid deletions, or amino acid additions. Amino acid substitutions for SEQ ID NO:40 or SEQ ID NO:44 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:40 or SEQ ID NO:44 can include no more than one, two, three, four, or five amino acid modifications.

In some cases, the constant region of a beta chain polypeptide of a TCR provided herein can have an amino acid sequence having at least 80% identity to the amino acid sequence set forth in SEQ ID NO:30 or SEQ ID NO:41. For example, the constant region of a beta chain polypeptide of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:30 or SEQ ID NO:41.

In some cases, the variable region of a beta chain polypeptide of a TCR provided herein can have an amino acid sequence having at least 80% identity to the amino acid sequence set forth in SEQ ID NO:48, provided that the beta chain includes the appropriate combination of CDRs (or variants of the CDRs) described herein. For example, the variable region of a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:48, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications).

In some cases, the variable region of a beta chain polypeptide of a TCR provided herein can include the amino acid sequence set forth in SEQ ID NO:48 (or a variant of SEQ ID NO:48 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:48 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:48 can include no more than one, two, three, four, or five amino acid modifications.

In some cases, a beta chain polypeptide of a TCR provided herein can have an amino acid sequence having at least 80% identity to the amino acid sequence set forth in SEQ ID NO:31 or SEQ ID NO:42, provided that the beta chain includes the appropriate combination of CDRs (or variants of the CDRs) described herein. For example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:31, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications). In another example, a beta chain of a TCR provided herein can have an amino acid sequence having at least 80%, 82%, 83%, 84%, 85%, 86%, 87%, 88%, 89%, 90%, 91%, 92%, 93%, 94%, 95%, 96%, 97%, 98%, 99%, or 100% identity to the amino acid sequence set forth in SEQ ID NO:42, provided that it includes (a) SEQ ID NO:23 (or SEQ ID NO:23 with no more than three, two, or one amino acid modifications), (b) SEQ ID NO:24 (or SEQ ID NO:24 with no more than three, two, or one amino acid modifications), and (c) SEQ ID NO:25 (or SEQ ID NO:25 with no more than three, two, or one amino acid modifications).

In some cases, a beta chain polypeptide of a TCR provided herein can have an amino acid sequence having at least 80% identity to the amino acid sequence set forth the amino acid sequence set forth in SEQ ID NO:31 (or a variant of SEQ ID NO:31 with one, two, three, four, five, six, seven, eight, nine, or 10 amino acid modifications, provided that the beta chain includes the appropriate combination of CDRs (or variants of the CDRs) described herein) or SEQ ID NO:42 (or a variant of SEQ ID NO:42 with one, two, three, four, five, six, seven, eight, nine, or 10 amino acid modifications, provided that the beta chain includes the appropriate combination of CDRs (or variants of the CDRs) described herein). Amino acid modifications can be amino acid substitutions, amino acid deletions, or amino acid additions. Amino acid substitutions for SEQ ID NO:31 or SEQ ID NO:42 can be conservative amino acid substitutions or non-conservative amino acid substitutions as discussed above for SEQ ID NOs:1, 2, 3, 10, 11, 12, 23, 24, 25, 32, 33, and 34. In some cases, a variant of SEQ ID NO:31 or SEQ ID NO:42 can include no more than one, two, three, four, or five amino acid modifications.

In some cases, a TCR provided herein can include no more than four (e.g., four, three, two, or one) amino acid modifications (e.g., amino acid substitutions, amino acid deletions, or amino acid additions) in one, two, three, or all four of the framework regions (the regions between the CDRs). For example, a TCR provided herein that has affinity for a SF3B1 peptide can include no more than four (e.g., four, three, two, or one) amino acid modifications in one, two, three, or all four of the alpha chain framework regions set forth in SEQ ID NOs:13, 14, 15, and 16 and/or the beta chain framework regions set forth in SEQ ID NOs:4, 5, 6, and 7. For example, a TCR provided herein that has affinity for a SF3B1 peptide can include no more than four (e.g., four, three, two, or one) amino acid modifications in one, two, three, or all four of the alpha chain framework regions set forth in SEQ ID NOs:35, 36, 37, and 38 and/or the beta chain framework regions set forth in SEQ ID NOs:26, 27, 28, and 29. In some cases, a TCR provided herein can include no more than four (e.g., four, three, two, or one) amino acid modifications (e.g., amino acid substitutions, amino acid deletions, or amino acid additions) in one, two, three, or all four of the framework regions set forth in SEQ ID NOs:4, 5, 6, 7, 13, 14, 15, and 16 and (i) one, two, or three amino acid modifications in one, two, or all three CDRs of the alpha chain variable region having the amino acid sequences set forth in SEQ ID NOs:10, 11, and 12 and/or (ii) one, two, or three amino acid modifications in one, two, or all three CDRs of the beta chain variable region having the amino acid sequences set forth in SEQ ID NOs:1, 2, and 3. In some cases, a TCR provided herein can include no more than four (e.g., four, three, two, or one) amino acid modifications (e.g., amino acid substitutions, amino acid deletions, or amino acid additions) in one, two, three, or all four of the framework regions set forth in SEQ ID NOs:26, 27, 28, 29, 35, 36, 37, and 38 and (i) one, two, or three amino acid modifications in one, two, or all three CDRs of the alpha chain variable region having the amino acid sequences set forth in SEQ ID NOs:32, 33, and 34 and/or (ii) one, two, or three amino acid modifications in one, two, or all three CDRs of the beta chain variable region having the amino acid sequences set forth in SEQ ID NOs:23, 24, and 25.

In some cases, a TCR provided herein can have the sequences as set forth in Table 2 (see FIG. 10 for the sequences).

In some cases, the linker can be a self-cleaving peptide (e.g., a 2A peptide) such that during translation of the transcripts, the growing polypeptide can be cleaved at the 2A peptide with translation continuing through to the next chain. When designing a vector to express the alpha and beta chains as a multicistronic unit, the nucleic acid encoding the alpha and beta chains and the self-cleaving peptide (e.g., a 2A peptide) can be designed such that they are in translational frame with each other. Examples of 2A peptides that can be used as described herein include, without limitation, a 2A peptide of foot-and-mouth disease virus (FMDV), a 2A peptide of equine rhinitis A virus (ERAVO), a 2A peptide of *Thosea asigna* virus (TaV), or a 2A peptide of porcine teschovirus-1 (PTV-1). 2A peptides derived from FMDV, ERAV, PTV-1, and TaV are referred to herein as "F2A,"

TABLE 2

Exemplary TCRs.

| TCR | SEQ ID NO of beta chain CDRs | SEQ ID NO of beta chain Framework regions | SEQ ID of constant region in beta chain | SEQ ID NO of variable region | SEQ ID NO of beta chain | SEQ ID NOs of alpha chain CDRs | SEQ ID NO of alpha chain Framework regions | SEQ ID of Constant region in alpha chain | SEQ ID NO of variable region | SEQ ID NO of alpha chain |
|---|---|---|---|---|---|---|---|---|---|---|
| TRBV2-01 + TRAV12-02 Chimeric TCR | 1, 2, 3 | 4, 5, 6, 7 | 8 | 47 | 9 | 10, 11, 12 | 13, 14, 15, 16 | 17 | 45 | 18 |
| TRBV2-01 + TRAV12-02 Human TCR | 1, 2, 3 | 4, 5, 6, 7 | 19 | 47 | 20 | 10, 11, 12 | 13, 14, 15, 16 | 21 | 45 | 22 |
| TRBV27-01 + TRAV13-01 Chimeric TCR | 23, 24, 25 | 26, 27, 28, 29 | 30 | 48 | 31 | 32, 33, 34 | 35, 36, 37, 38 | 39 | 46 | 40 |
| TRBV27-01 + TRAV13-01 Human TCR | 23, 24, 25 | 26, 27, 28, 29 | 41 | 48 | 42 | 32, 33, 34 | 35, 36, 37, 38 | 43 | 46 | 44 |

This document also provides isolated nucleic acids that encode an alpha and/or beta chain polypeptide of a TCR provided herein. See, for example, FIG. 1B, FIG. 3, FIG. 5, FIG. 9, FIG. 11A, FIG. 11B, FIG. 13A, FIG. 13B, FIG. 15A, FIG. 15B, FIG. 17A, or FIG. 17B. In some cases, the nucleic acid sequence can be codon optimized for expression in a host cell (e.g., a human host cell). See, for example, FIG. 2, FIG. 4, FIG. 6, FIG. 8, FIG. 12A, FIG. 12B, FIG. 14A, FIG. 14B, FIG. 16A, FIG. 16B, FIG. 18A, or FIG. 18B. In addition, this document provides vectors containing one or more of such nucleic acids. The nucleic acids provided herein can be single stranded and double stranded nucleic acids of any appropriate type (e.g., DNA, RNA, or DNA/ RNA hybrids). The nucleic acids provided herein can be used therapeutically or can be used in methods for producing a TCR.

In some cases, a nucleic acid provided herein includes a nucleic acid sequence that encodes an alpha chain of a TCR and a nucleic acid sequence that encodes a beta chain of a TCR. The nucleic acid also can include a nucleic acid sequence encoding a linker. The nucleic acid sequence encoding the linker can be between the nucleic acid encoding an alpha chain and the nucleic acid encoding the beta chain to allow the alpha and beta chains to be encoded by the same contiguous nucleic acid sequence. For example, the nucleic acid sequence encoding the linker can be 3' of the nucleic acid sequence encoding the alpha chain and 5' of the nucleic acid sequence encoding the beta chain or it can be 3' of the nucleic acid sequence encoding the beta chain and 5' of the nucleic acid sequence encoding the alpha chain.

"E2A," "P2A," and "T2A," respectively. Table 3 provides exemplary amino acid sequences of 2A peptides.

TABLE 3

Exemplary 2A peptides that can be used as described herein.

| Type | Peptide Sequence | SEQ ID NO: |
|---|---|---|
| P2A | GSGATNFSLLKQAGDVEENPGP or RAKRSGSGATNFSLLKQAGDVEENPGP | 80 / 81 |
| T2A | GSGEGRGSLLTCGDVEENPGP | 82 |
| E2A | GSGQCTNYALLKLAGDVESNPGP | 83 |
| F2A | GSGVKQTLNFDLLKLAGDVESNPGP | 84 |

In some cases, an Internal Ribosome Entry Site (IRES) can be used in place of (or in addition to) a self-cleaving peptide. Examples of IRES sequences that can be used as described herein include, without limitation, an Encephalomyocrditis virus (EMCV) IRES (e.g., IRES2), a Hepatitis C virus (HCV) IRES, a Picoma virus IRES, and a Pestivirus IRES.

In some cases, a linker can include a furin cleavage site. Furin is a ubiquitously expressed protease that resides in the trans-golgi and processes protein precursors before their secretion. Furin cleaves at the COOH terminus of its consensus recognition sequence. Examples of furin consensus recognition sequences (or "furin cleavage sites") that can be used as described herein include, without limitation, Arg-X-Lys-Arg (SEQ ID NO:84) or Arg-X-Arg-Arg (SEQ ID NO:85), (Lys/Arg)-Arg-X-(Lys/Arg)-Arg (SEQ ID NO:86) and Arg-X-X-Arg (SEQ ID NO:87), such as an Arg-Gln-Lys-Arg (SEQ ID NO:88), where X is any naturally occurring amino acid.

A vector that includes one or more nucleic acids that encode an alpha chain and/or beta chain of a TCR provided herein can be a nucleic acid vector (e.g., naked DNA or plasmid vector) or a viral vector. Examples of viral vectors that can be designed to include one or more nucleic acids encoding an alpha chain and/or beta chain of a TCR provided herein include, without limitation, retroviral vectors, parvovirus-based vectors (e.g., adenoviral-based vectors and adeno-associated virus (AAV)-based vectors), lentiviral vectors (e.g., herpes simplex (HSV)-based vectors), or poxviral vectors (e.g., vaccinia virus-based vectors and fowlpox virus-based vectors), and hybrid or chimeric viral vectors. For example, a viral vector having an adenoviral backbone with lentiviral components such as those described elsewhere (Zheng et al., Nat. Biotech., 18(2):176-80 (2000); WO 98/22143; WO 98/46778; and WO 00/17376) or viral vectors having an adenoviral backbone with AAV components such as those described elsewhere (Fisher et al., Hum. Gene Ther., 7:2079-2087 (1996)) can be designed to include one or more nucleic acids encoding an alpha chain and/or beta chain of a TCR provided herein. Any appropriate nucleic acid or viral vector construction methods can be used to make a nucleic acid vector that includes one or more nucleic acids encoding an alpha chain and/or beta chain of a TCR provided herein (see, e.g., Green and Sambrook, Molecular Cloning: A Laboratory Manual, 4th edition, Cold Spring Harbor Laboratory, NY (2012); and Ausubel et al., Current Protocols in Molecular Biology, Green Publishing Associates and John Wiley & Sons, New York, N.Y. (1987-2008)).

A vector provided herein (e.g., a nucleic acid or viral vector provided herein) can include any appropriate promoter and/or other regulatory sequences (e.g., transcription and translation initiation and termination codons) operably linked the nucleic acid encoding a polypeptide (e.g., an alpha chain and/or beta chain of a TCR provided herein). In some cases, a promoter used to drive expression of an alpha chain and/or beta chain of a TCR provided herein can be a constitutive or regulatable promotor. Examples of regulatable promoters that can be used as described herein include, without limitation, inducible promotors, repressible promotors, and tissue-specific promoters. Examples of viral promotors that can be used as described herein include, without limitation, adenoviral promotors, vaccinia virus promotors, and AAV promoters. In some embodiments, the promoter can be a viral 5' long terminal repeat (LTR) or 3' LTR.

In some cases, a vector includes a separate promoter to drive expression of each chain instead of using a linker between the chains. In these cases, one promoter sequence can drive expression of an alpha chain, and a separate promoter sequence can drive expression of a beta chain. These two promoter sequences can be the same or different.

This document also provides cells (e.g., host cells or isolated cells) that include a nucleic acid provided herein (e.g., a nucleic acid encoding an alpha chain and/or beta chain of a TCR provided herein, or a nucleic acid vector or viral vector provided herein). Such cells (e.g., host cells or isolated cells) that can be designed to include one or more nucleic acids provided herein can be prokaryotic cells or eukaryotic cells. Examples of prokaryotic cells that can include a nucleic acid provided herein (e.g., a nucleic acid encoding an alpha chain and/or beta chain of a TCR provided herein, or a nucleic acid vector or viral vector provided herein) include, without limitation, E. coli (e.g., Tb-1, TG-1, DH5α, XL-Blue MRF (Stratagene), SA2821, or Y1090 cells), Bacillus subtilis, Salmonella typhimurium, Serratia marcescens, or Pseudomonas (e.g., P. aerugenosa) cells.

Examples of eukaryotic cells that can include a nucleic acid provided herein (e.g., a nucleic acid encoding an alpha chain and/or beta chain of a TCR provided herein, or a nucleic acid vector or viral vector provided herein) include, without limitation, insect cells (e.g., Sf9 or Ea4 cells), yeast cells (e.g., S. cerevisiae cells), and mammalian cells (e.g., mouse, rat, hamster, monkey, or human cells). For example, VERO cells, HeLa cells, 3T3 cells, Chinese hamster ovary (CHO) cells, W138 BHK cells, COS-7 cells, and MDCK cells can be designed to include a nucleic acid provided herein (e.g., a nucleic acid encoding an alpha chain and/or beta chain of a TCR provided herein, or a nucleic acid vector or viral vector provided herein).

In some cases, a eukaryotic cell that includes a nucleic acid provided herein (e.g., a nucleic acid encoding an alpha chain and/or beta chain of a TCR provided herein, or a nucleic acid vector or viral vector provided herein) is an immune cell such as a T cell. Such cells can include an exogenous TCR, expressed from the nucleic acid provided herein, on their surface that has reactivity against the mutated form of SF3B1 without having reactivity to the non-mutated form of SF3B1. A T cell can be any type of T cell and can be of any developmental stage, including CD4+ and/or CD8+ T cells. For example, the T cells can be helper T cells, e.g., Th1 and Th2 cells, CD8+ T cells (e.g., cytotoxic T cells), tumor infiltrating cells (TILs), memory T cells, naive T cells, cytotoxic T lymphocytes (CTLs), regulatory T cells, activated T cells, memory T cells, or natural killer cells. The T cell can be a cultured T cell, e.g., a primary T cell or a T cell from a cultured T cell line, e.g., Jurkat or Sup-T1. In some cases, the T cell can be isolated from a mammal such as a human. Mammalian T cells can be obtained, for example, from blood, bone marrow, lymph node, the thymus, or other tissues or fluids. T cells also can be enriched or purified.

In some cases, the T cell can be isolated from the mammal to be treated, i.e., the cells are autologous to the mammal (e.g., human), and modified to include a nucleic acid provided herein (e.g., a nucleic acid encoding an alpha chain and/or beta chain of a TCR provided herein, or a nucleic acid vector or viral vector provided herein) and comprise an exogenous TCR on the surface of the cell that is expressed from the nucleic acid. For example, for autologous cells, the immune cells can be obtained from the mammal's blood, cord blood, or bone marrow. In some cases, the T cells are heterologous to the mammal, i.e., the cells are not from the mammal to be treated.

In some cases, an immune cell such as a T cell (e.g., a human T cell) that includes a nucleic acid provided herein (e.g., a nucleic acid encoding an alpha chain and/or beta chain of a TCR provided herein, or a nucleic acid vector or viral vector provided herein) and comprises an exogenous TCR expressed from the nucleic acid, can lack expression of an endogenous alpha chain of a TCR and/or lack expression of an endogenous beta chain of a TCR. Any appropriate method can be used to generate T cells that lack expression of one or both chains of an endogenous TCR. For example, gene editing techniques such as those that involve using Clustered Regularly Interspaced Short Palindromic Repeats (CRISPR) technology or Transcription Activator-Like Effector Nuclease (TALEN) technology can be used to interfere with the expression of one or both chains of an endogenous TCR.

In some cases, an immune cell such as a natural killer (NK) cell that includes a nucleic acid provided herein (e.g., a nucleic acid encoding an alpha chain and/or beta chain of a TCR provided herein, or a nucleic acid vector or viral vector provided herein) and comprises an exogenous TCR expressed from the nucleic acid, can be engineered to express one or more of the CD3 chains of the TCR complex (e.g., the CD3ε, CD3γ, CD3ζ, and optionally CD3δ). In such cases, the exogenous TCR can be expressed on the surface of the immune cell (e.g., a NK cell) in combination with the exogenously provided one or more CD3 chains of a CD3 complex.

In some cases, an immune cell such as a T cell (e.g., a human T cell) that includes a nucleic acid provided herein (e.g., a nucleic acid encoding an alpha chain and/or beta chain of a TCR provided herein, or a nucleic acid vector or viral vector provided herein) and comprises an exogenous TCR expressed from the nucleic acid, expresses an endogenous TCR. In such cases, a portion of the TCRs present on the surface of such T cells can be endogenous TCRs, a portion of the TCRs present on the surface of such T cells can be exogenously provided TCRs (e.g., TCRs containing the alpha and beta chain polypeptides described herein), and a portion of the TCRs present on the surface of such T cells can have one endogenous provided TCR chain and one exogenously provided TCR chain.

In some cases, the constant regions of the alpha and beta chains encoded by a nucleic acid provided herein can be engineered to include sequences that encode one or more cysteine residues to increase the pairing of the alpha and beta chains with each other when expressed within a cell. Examples of such cysteine residues include, without limitation, those described elsewhere (see, e.g., Kuball et al., *Blood,* 109:2331-2338 (2007)).

Any appropriate method can be used to introduce one or more nucleic acids provided herein (e.g., a vector containing a nucleic acid encoding the alpha chain and/or beta chain polypeptides of a TCR provided herein) into a cell (e.g., a host cell or an isolated cell). For example, calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, electroporation, or combinations thereof can be used to introduce a nucleic acid provided herein into a cell (e.g., a host cell or an isolated cell) (see, e.g., Green and Sambrook, Molecular Cloning: A Laboratory Manual, 4th edition, Cold Spring Harbor Laboratory, NY (2012); Davis et al., Basic Methods in Molecular Biology (1986); and Neumann et al., *EMBO J.,* 1:841 (1982)).

The immune cells (e.g., T cells) can be activated and expanded, before or after introduction of the nucleic acid. T-cell activation reagents are commercially available, including CTS™ Dynabeads™ CD3/28, MACS GMP ExpAct Treg beads (Miltenyi Biotec), MACS GMP Trans-Act CD3/28 beads (Miltenyi Biotec), and Expamer technology (Juno Therapeutics). See, for example, Wang and Riviere, *Molecular Therapy Oncolytics,* 3:16015 (2016). T cells can be expanded, for example, using a GE WAVE bioreactor system that includes a Cellbag Bioreactor and a rocking base, and which allows the cells to expand to more than $10^7$ cells/mL. In some cases, T cells can be expanded using Gas Permeable Rapid Expansion (G-Rex®) (Wilson Wolf Manufacturing), which includes a cell culture flask with a gas-permeable membrane at the base that allows cells to grow to a high density. T cells also can be expanded using a CliniMACS Prodigy system (Miltenyi Biotec), which uses a magnetic cell separation system, and a cell cultivation device. See, for example, Wang and Riviere, *Molecular Therapy Oncolytics,* 3:16015 (2016).

In some cases, the immune cells (e.g., T cells) that include, for example, a vector containing a nucleic acid encoding the alpha chain and/or beta chain polypeptides of a TCR provided herein, can be cryopreserved for use at a later time. For example, the cells can be cryopreserved with dimethylsulfoxide (DMSO) and human serum albumin (HSA). In some cases, the cells can be cryopreserved with a balanced crystalloid solution (e.g., Plasma-Lyte 148), DMSO, and HSA.

In some cases, a nucleic acid provided herein, a vector provided herein, or an immune cell provided herein can be formulated as a pharmaceutical composition for administration to a mammal (e.g., a human) to treat a disorder, disease, or condition. For example, immune cells that comprise an exogenous TCR provided herein can be formulated and used for cell therapy, e.g., adoptive cell therapy. In some cases, a nucleic acid, a vector, or an immune cell provided herein can be formulated for administration to a mammal (e.g., a human to treat cancer). In some cases, a pharmaceutical composition provided herein can include a pharmaceutically acceptable carrier such as a buffer, a salt, a surfactant, a sugar, a tonicity modifier, or combinations thereof. See, for example, Gervasi, et al., *Eur. J. Pharmaceutics and Biopharmaceutics,* Volume 131, pages 8-24 (2018). Examples of pharmaceutically acceptable carriers that can be used to make a pharmaceutical composition provided herein include, without limitation, water, lactic acid, citric acid, sodium chloride, sodium citrate, sodium succinate, sodium phosphate, a surfactant (e.g., polysorbate 20, polysorbate 80, or poloxamer 188), dextran 40, or a sugar (e.g., sorbitol, mannitol, sucrose, dextrose, or trehalose), or combinations thereof. For example, a pharmaceutical composition designed to include immune cells comprising an exogenous TCR provided herein (or nucleic acid or vector encoding an alpha and/or beta chain of a TCR) can be formulated to include a buffer (e.g., an acetate, citrate, histidine, succinate, phosphate, hydroxymethylaminomethane (Tris), or Plasma-lyte buffer).

In some cases, when a pharmaceutical composition is formulated to include immune cells, the formulation contains a sufficient number of cells to deliver about $1\times10^5$ to about $1\times10^{10}$ cells/kg body weight to the mammal. For example, the formulation contains a sufficient number of cells to deliver $1\times10^5$ to about $1\times10^9$ cells/kg body weight, $1\times10^5$ to about $1\times10^8$ cells/kg body weight, $2\times10^5$ to about $2\times10^6$ cells/kg body weight, or $1\times10^6$ to about $1\times10^7$ cells/kg body weight to the mammal.

In some cases, when a pharmaceutical composition is formulated to include one or more nucleic acids (e.g., vectors such as viral vectors) encoding an alpha and/or beta chain of a TCR provided herein, any appropriate concentration of the nucleic acid can be used. For example, a pharmaceutical composition provided herein can be formulated to be a liquid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a nucleic acid (e.g., a vector such as a viral vector) encoding an alpha and/or beta chain of a TCR per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a nucleic acid (e.g., a vector such as a viral vector) encoding a an alpha and/or beta chain of a TCR.

A pharmaceutical composition provided herein can be in any appropriate form. For example, a pharmaceutical composition provided herein can designed to be a liquid, a semi-solid, or a solid. In some cases, a pharmaceutical composition provided herein can be a liquid solution (e.g., an injectable and/or infusible solution), a dispersion, a suspension, a tablet, a pill, a powder, a microemulsion, a liposome, or a suppository. In some cases, a pharmaceutical composition provided herein can be lyophilized. In some cases, a pharmaceutical composition provided herein (e.g., a pharmaceutical composition that includes one or more nucleic acids provided herein) can be formulated with a carrier or coating designed to protect against rapid release. For example, a pharmaceutical composition provided herein can be formulated as a controlled release formulation or as a regulated release formulation as described elsewhere (U.S. Patent Application Publication Nos. 2019/0241667; 2019/0233522; and 2019/0233498).

This document also provides methods for administering a composition (e.g., a pharmaceutical composition provided herein) containing immune cells that include an exogenous TCR provided herein (or nucleic acid or vector encoding an alpha and/or beta chain of such a TCR) to a mammal (e.g., a human). For example, a composition (e.g., a pharmaceutical composition provided herein) containing immune cells that include an exogenous TCR provided herein (or nucleic acid or vector encoding an alpha and/or beta chain of such a TCR) can be administered to a mammal (e.g., a human) in need thereof to treat a disorder, disease, or condition. Any appropriate method can be used to administer a composition (e.g., a pharmaceutical composition provided herein) to a mammal (e.g., a human). For example, a composition (e.g., a pharmaceutical composition provided herein) containing immune cells that include an exogenous TCR provided herein (or nucleic acid or vector encoding an alpha and/or beta chain of such a TCR) can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a pharmaceutical composition provided herein) containing immune cells that include an exogenous TCR provided herein (or nucleic acid or vector encoding an alpha and/or beta chain of such a TCR) can be adjusted for the mammal being treated.

Effective doses of a composition containing immune cells that include an exogenous TCR provided herein (or nucleic acid or vector encoding an alpha and/or beta chain of such a TCR) can vary depending on the severity of the disorder, the route of administration, the age and general health condition of the subject, excipient usage, the possibility of co-usage with other therapeutic treatments such as use of other agents, and the judgment of the treating physician.

In some cases, an effective amount of a composition containing immune cells comprising an exogenous TCR provided herein (or nucleic acid or vector encoding an alpha and/or beta chain of such a TCR) can be an amount that reduces the activity of the target antigen within a mammal without producing significant toxicity to the mammal. For example, an effective amount of immune cells that comprise an exogenous TCR provided herein can be from about $1\times10^5$ to about $1\times10^{10}$ cells/kg body weight. For example, the cells can be administered to the mammal at a range of $1\times10^5$ to about $1\times10^9$ cells/kg body weight, $1\times10^5$ to about $1\times10^8$ cells/kg body weight, $2\times10^5$ to about $2\times10^6$ cells/kg body weight, $1\times10^6$ to about $1\times10^7$ cells/kg body weight.

The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of immune cells that include an exogenous TCR provided herein (or nucleic acid or vector an alpha and/or beta chain of such a TCR) can be any amount that maintains a fairly steady state of reduced target antigen activity within a mammal without producing significant toxicity to the mammal. For example, the frequency of administration of immune cells provided herein can be from about twice daily to about once a week. In some cases, the frequency of administration of immune cells provided herein can be daily. The frequency of administration of immune cells provided herein can remain constant or can be variable during the duration of treatment. A course of treatment with a composition containing immune cells provided herein can include rest periods. For example, a composition containing immune cells provided herein can be administered daily over a two-week period followed by a one-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing immune cells that include an exogenous TCR provided herein (or nucleic acid or vector encoding the alpha and/or beta chains of such a TCR) can be any appropriate duration that reduces the activity of the target antigen within a mammal without producing significant toxicity to the mammal. In some cases, the effective duration can vary from several weeks to several years (e.g., 5, 10, 15, or more years). Multiple factors can influence the actual effective duration used for a particular treatment. For example, an effective duration can vary with the frequency of administration, effective amount, use of multiple treatment agents, route of administration, and severity of the condition being treated.

In some cases, a composition containing immune cells that include an exogenous TCR provided herein (or nucleic acid or vector encoding the alpha and/or beta chains of such a TCR) can be administered as part of a combination treatment, such as simultaneously with or sequentially with, in any order, another therapeutic agent, such as a cytokine (e.g., IL-2), antibody (e.g., tocilizumab, which blocks IL-6 activity), an immune checkpoint inhibitor (e.g., one or more of an anti-PD-1 antibody, an anti-PDL-1 antibody, or an anti-CTLA-4 antibody), or a chemotherapeutic agent.

The invention will be further described in the following examples, which do not limit the scope of the invention described in the claims.

EXAMPLES

To confirm the specificity and activity of nucleic acid encoding TCRs against SF3B1, the nucleic acids were introduced into donor T cells. These TCR-transduced T cells were co-cultured with dendritic cells expressing wildtype SF3B1 or mutated forms of SF3B1 (R625H, R625G, R625L, or R625C). After overnight incubation, the supernatant was assessed for production of interferon-gamma. It was found that the introduced nucleic acids encoding TCRs conferred SF3B1 R625H mutation reactivity without reactivity against the wildtype form of SF3B1 or against other mutant forms of SF3B1 (R625G, R625L, or R625C). See, FIG. 9.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated human immune cell comprising an exogenous T cell receptor (TCR) having affinity for a human splicing factor 3B subunit 1A (SF3B1) peptide comprising a histidine at position 625 in the context of DRB3, said exogenous TCR comprising an alpha chain and a beta chain,
    said alpha chain comprising the amino acid sequences set forth in SEQ ID NO:10, SEQ ID NO:11, and SEQ ID NO:12, and
    said beta chain comprising the amino acid sequences set forth in SEQ ID NO:1, SEQ ID NO:2, and SEQ ID NO:3.

2. The immune cell of claim 1, wherein said alpha chain comprises an amino sequence having at least 80 percent identity to the amino acid sequence set forth in SEQ ID NO:18 or SEQ ID NO:22.

3. The immune cell of claim 1, wherein said beta chain comprises an amino acid sequence having at least 80 percent identity to the amino acid sequence set forth in SEQ ID NO:9 or SEQ ID NO:20.

4. The immune cell of claim 1, wherein said immune cell is a T cell.

5. The immune cell of claim 4, wherein expression of the endogenous TCR alpha and beta chain coding sequences are downregulated in said T cell.

6. A nucleic acid molecule comprising (i) a nucleic acid sequence encoding an alpha chain of a TCR having affinity for a human SF3B1 peptide comprising a histidine at position 625 in the context of DRB3 and (ii) a nucleic acid sequence encoding a beta chain of said TCR,
    said alpha chain comprising the amino acid sequences set forth in SEQ ID NO:10, SEQ ID NO:11, and SEQ ID NO:12, and said beta chain comprising the amino acid sequences set forth in SEQ ID NO:1, SEQ ID NO:2, and SEQ ID NO:3.

7. The nucleic acid of claim 6, wherein said nucleic acid comprises a promoter 5' of said nucleic acid sequence encoding said alpha chain, and comprises a promoter 5' of said nucleic acid sequence encoding said beta chain.

8. The nucleic acid of claim 7, wherein each of said promoters is a viral 5' long terminal repeat or a viral 3' long terminal repeat.

9. The nucleic acid of claim 6, wherein said nucleic acid is a vector.

10. The nucleic acid of claim 9, wherein said vector is a viral vector.

11. The nucleic acid of claim 10, wherein said vector is a retroviral vector or a lentiviral vector.

12. The nucleic acid of claim 6, said nucleic acid further comprising a nucleic acid sequence encoding a linker, wherein said linker is between the nucleic acid sequence encoding the alpha chain and the nucleic acid sequence encoding the beta chain.

13. The nucleic acid of claim 12, wherein said linker is a self-cleaving peptide.

14. The nucleic acid of claim 13, wherein said self-cleaving peptide is a self-cleaving peptide of a foot-and-mouth disease virus (FMDV), an equine rhinitis A virus (ERAVO, a Thosea asigna virus (TaV), or a porcine tescho virus-1 (PTV-1).

15. The nucleic acid of claim 13, wherein said self-cleaving peptide is a P2A peptide.

16. The nucleic acid of claim 12, wherein said linker includes a furin cleavage site.

17. A method of making an immune cell comprising an exogenous TCR having affinity for a human SF3B1 peptide comprising a histidine at position 625 in the context of DRB3, said method comprising introducing, into said immune cell, nucleic acid of claim 6, wherein said exogenous TCR is expressed from said nucleic acid in said immune cell.

18. An isolated immune cell comprising the nucleic acid of claim 6, said immune cell comprising an exogenous TCR having affinity for a human SF3B1 peptide comprising a histidine at position 625 in the context of DRB3.

19. A population of cells comprising at least one isolated immune cell of claim 18.

20. A pharmaceutical composition comprising the population of cells of claim 19 and a pharmaceutically acceptable carrier.

21. A method for treating a mammal in need thereof, wherein said mammal is a human having melanoma and presenting a human SF3B1 peptide comprising a histidine at position 625 in the context of DRB3, wherein said method comprises administering to the mammal an effective amount of said pharmaceutical composition of claim 20.

22. The method of claim 21, wherein said immune cells are autologous to said mammal.

\*  \*  \*  \*  \*

122